(12) United States Patent
Ahmad et al.

(10) Patent No.: US 6,887,870 B1
(45) Date of Patent: May 3, 2005

(54) HETEROCYCLIC SODIUM/PROTON EXCHANGE INHIBITORS AND METHOD

(75) Inventors: Saleem Ahmad, Wall, NJ (US); Shung C. Wu, Princeton, NJ (US); Steven V. O'Neil, Newtown, PA (US); Khehyong Ngu, Pennington, NJ (US); Karnail S. Atwal, Newtown, PA (US); David S. Weinstein, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 50 days.

(21) Appl. No.: 09/669,298

(22) Filed: Sep. 25, 2000

Related U.S. Application Data
(60) Provisional application No. 60/158,755, filed on Oct. 12, 1999.

(51) Int. Cl.[7] .................. A61K 31/4427; C07D 401/04
(52) U.S. Cl. .................... 514/235.8; 514/241; 514/242; 514/250; 514/253.09; 514/253.1; 514/256; 514/259.41; 514/260.1; 514/300; 514/320; 514/321; 514/322; 514/323; 514/326; 544/122; 544/182; 544/212; 544/278; 544/281; 544/322; 544/328; 544/331; 544/349; 544/360; 546/121; 546/198; 546/199; 546/201; 546/208; 546/209; 546/210; 546/212; 546/214
(58) Field of Search .................. 544/122, 182, 544/212, 278, 281, 322, 328, 331, 349, 360, 238, 317; 546/121, 198, 199, 201, 208, 209, 210, 212, 214, 193, 194, 211; 514/235.8, 241, 242, 250, 253.09, 253.1, 256, 259.41, 260.1, 300, 320, 321, 322, 323, 326, 318, 252.03, 274, 258

(56) References Cited

U.S. PATENT DOCUMENTS

| 4,707,487 A | * | 11/1987 | Arrang et al. | ............... 514/326 |
| 5,280,030 A | * | 1/1994 | Jegham et al. | ............... 514/322 |
| 5,434,169 A | * | 7/1995 | Jegham et al. | ............... 514/322 |
| 5,663,350 A | * | 9/1997 | Durant et al. | ............... 546/185 |

FOREIGN PATENT DOCUMENTS

| EP | 1136489 A1 | * 9/2001 | ......... C07D/401/14 |
| FR | 2765221 | 12/1998 | |
| HU | 193292 B | 9/1987 | |
| WO | WO 9726258 A1 | * 7/1997 | ......... C07D/417/04 |
| WO | WO99/00379 | 1/1999 | |
| WO | WO99/01435 | 1/1999 | |
| WO | WO 99/31089 | * 6/1999 | |

OTHER PUBLICATIONS

CAs printout of EP 1136489.*
CAS printout of Liras et al. Chem. Abs. 133:222737 (US 6444679).*
CAS printout for Farina et al. Chem. Abs. 125:96333, 1996.*
CAS printout for Nakazato et al. Chem. Abs. 129:275927.*
CAS printout for Stokbboekx et al. Chem. Abs. 127:176434.*
CAS printout for Ganellin et al.*
CAS printout for Even et al.*
CAS printout for Schunack et al.*
CAS printout for Corbel.*
CAS printout for Lange et al.*

* cited by examiner

*Primary Examiner*—Richard L. Raymond
(74) *Attorney, Agent, or Firm*—Burton Rodney

(57) ABSTRACT

Heterocyclic are provided which are sodium/proton exchange (NHE) inhibitors which have the structure

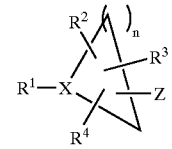

wherein n is 1 to 5; X is N or C—$R^5$ wherein $R^5$ is H, halo, alkenyl, alkynyl, alkoxy, alkyl, aryl or heteroaryl; Z is a heteroaryl gorup, $R^1$, $R^2$, $R^3$ and $R^4$ are as defined herein, and where X is N. $R^1$ is preferably aryl or heteroaryl, and are useful as antianginal and cardioprotective agents. In addition, a method is provided for preventing or treating angina pectoris, cardiac dysfunction, myocardial necrosis, and arrhythmia employing the above heterocyclic derivatives.

28 Claims, No Drawings

HETEROCYCLIC SODIUM/PROTON EXCHANGE INHIBITORS AND METHOD

This application claims priority from provisional application No. 60/158,755 filed Oct. 12, 1999.

FIELD OF THE INVENTION

The present invention relates to heterocyclic compounds which are sodium/proton exchange (NHE) inhibitors and are useful as antianginal agents and cardioprotective agents.

BRIEF DESCRIPTION OF THE INVENTION

In accordance with the present invention, novel heterocyclic derivatives are provided which are sodium/proton exchange (NHE) inhibitors and have the structure I

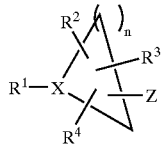

including pharmaceutically acceptable salts thereof and all stereoisomers thereof, and prodrugs thereof, wherein n is an integer from 1 to 5;

X is N or C—$R^5$ wherein $R^5$ is H, halo, alkenyl, alkynyl, alkoxy, alkyl, aryl or heteroaryl;

Z is a heteroaryl and preferably is a heteroaryl group containing 1 to 4 hetero atoms, at least one of which is a nitrogen atom, the heteroaryl group being attached to the rest of the molecule by way of an available nitrogen or carbon atom;

$R^1$ is H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, amino, alkylamino, dialkylamino, alkenylamino, alkynylamino, arylalkylamino, aryl, arylalkyl, arylamino, aryloxy, cycloheteroalkyl, cycloheteroalkylalkyl, heteroaryl, heteroarylamino, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl such as $CF_3$ and $CF_3CH_2$, polyhaloalkyloxy such as $CF_3O$ and $CF_3CH_2O$, aminothio, aminosulfinyl, aminosulfonyl, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, acyl, carboxy, aminocarbonyl, alkylcarbonyl, alkoxycarbonyl, alkylcarbonyloxy, alkylcarbonylamino, arylcarbonyl, arylcarbonyloxy, arylcarbonylamino, heteroarylcarbonyl, heteroarylcarbonyloxy, heteroarylcarbonylamino, cyano, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, 1,1-(alkoxyl or aryloxy)$_2$alkyl (where the two aryl or alkyl substituents can be independently defined, or linked to one another to form a ring, such as 1,3-dioxane or 1,3-dioxolane), S(O)$_2R^6R^7$, —NR$^6$ (C=NR$^7$)alkyl, NR$^6$(C=NR$^7$)alkenyl, —NR$^6$(C=NR$^7$)alkynyl,

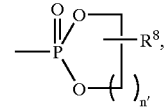

NR$^6$(C=NR$^7$)heteroaryl, —NR$^8$(C=NCN)-amino, pyridine-N-oxide,

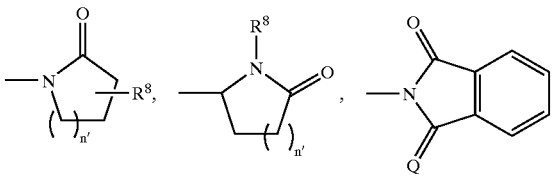

(where Q is O or H$_2$ and n' is 0, 1, 2 or 3) or

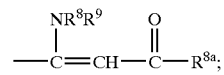

tetrazolyl, pyrazolyl, pyridyl, thiazolyl, pyrimidinyl, imidazole, oxazole or triazole; —PO($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy);

$R^6$, $R^7$, $R^8$, $R^{8a}$ and $R^9$ are independently hydrogen, alkyl, haloalkyl, aryl, heteroaryl, arylalkyl, cycloalkyl, (cycloalkyl)alkyl or cycloheteroalkyl.

The $R^1$ group may have from one to five substituents, which can independently be any of the $R^1$ groups set out above, and any of the preferred $R^1$ substituents set out below, which substituents may be the same or different from each other and may be the same of different from the base $R^1$ group.

$R^1$ may be substituted with one or more of the following preferred substituents: alkyl, alkylamino-carbonyl, arylaminocarbonyl, heteroarylaminocarbonyl, alkylcarbonylamino, heteroaryl, halo, aryl, cycloalkylcarbonylamino, arylcarbonylamino, heteroarylcarbonylamino, alkoxycarbonylamino, guanidinyl, nitro, cycloheteroalkyl, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

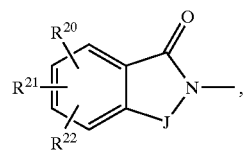

where

J is: CHR$^{23}$,

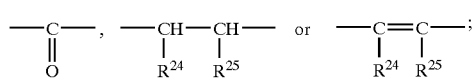

R$^{23}$, R$^{24}$ and R$^{25}$ are independently hydrogen, alkyl, alkenyl, alkynyl, aryl, arylalkyl, heteroaryl, heteroarylalkyl, cycloalkyl, or cycloalkylalkyl;

R$^{20}$, R$^{21}$, R$^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to R$^1$, or attached via an alkylene chain at an open position.

R$^2$, R$^3$ and R$^4$ are the same or different and are independently any of the groups set out for R$^1$ (and may be the same or different from R$^1$) and may optionally include one to five substituents which include independently any of the substituents set out for R$^1$, which may be the same or different.

The R$^2$, R$^3$ and/or R$^4$ groups can be attached to any of the carbons and/or to X which form the ring shown in formula I and, if desired, two of R$^2$, R$^3$ and/or R$^4$ may be attached to a single carbon atom.

The R$^1$, R$^2$, R$^3$ and/or R$^4$ may be joined together with the N atom and/or carbons to which they are attached to form a non-aromatic carbocyclic ring (namely, a cycloalkyl or cycloalkenyl ring), a cycloheteroalkyl ring or a heteroaryl ring, which contains 5 to 10 ring members, preferably 5 to 7 ring members. In addition, one of R$^2$, R$^3$ and R$^4$ can make a fused non-aromatic carbocyclic ring, namely a cycloalkyl ring or cycloalkenyl ring, with R$^1$ via linkage at the position adjacent to the linkage of X and R$^1$.

In the compounds of formula I where X is N, n is 4 (i.e., piperidine ring), and Z is imidazol-4-yl or 5-alkylimidazol-4-yl attached at the 4-position of the ring, then R$^1$ is other than phenyl or substituted phenyl.

The group A

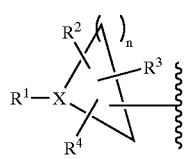

A preferably includes, but is not limited to, the following structures

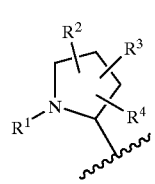 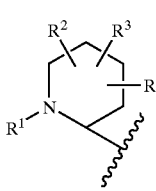 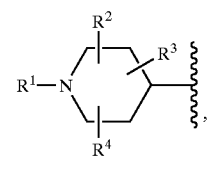

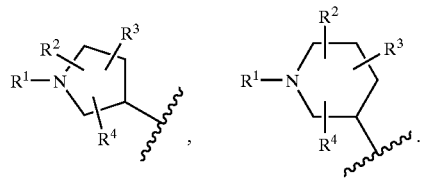

Also preferred is

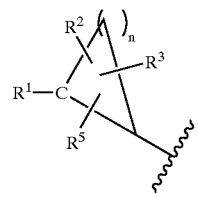

which preferably includes

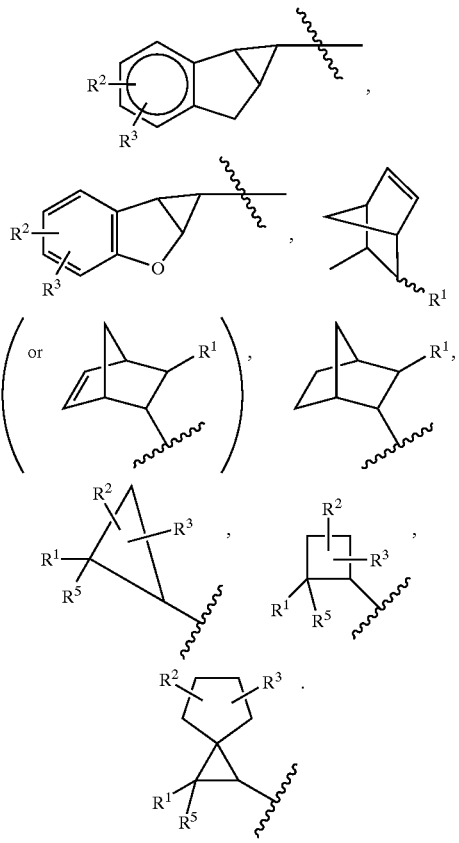

Thus, the compounds of formula I of the invention can have the following structural formulae:

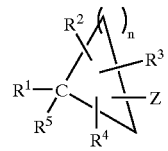

IA

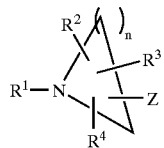

It is preferred that at least one of $R^1$, $R^2$, $R^3$ and $R^4$ is aryl or heteroaryl. It is also preferred that in IB (where X is N)$R^1$ is aryl or heteroaryl.

Preferred are compounds of formula I of the invention wherein n is 1, 2, 3 or 4, more preferably 1 or 4; preferably X is CH or N; Z is preferably imidazole, aminoimidazole, alkylimidazole, alkylthioimidazole, alkylthio(amino)imidazole, amino(alkyl)imidazole, (alkanoylamino)imidazole, oxazole, thiazole, benzimidazole, aminothiazole, aminooxazole, aminooxadiazole, dialkylimidazole, alkyl(alkanoylamino)imidazole, alkyl(amino)imidazole, arylaminocarbonylamino(alkyl)imidazole, alkoxycarbonylamino(alkyl)imidazole, alkylcarbonylamino(alkyl)imidazole, aminotriazole, or diaminopyrimidine, Z is more preferably imidazole, aminoimidazole, alkylimidazole, dialkylimidazole, alkylthioimidazole, alkylthio(amino)imidazole, amino(alkyl)imidazole and (acetylamino)imidazole; preferably $R^2$ and $R^3$ are independently H, lower alkyl, lower alkoxy, heteroaryl, or aryl; more preferably $R^2$ and $R^3$ are independently H, lower alkyl, aryl, and heteroaryl; and $R^4$ and $R^5$ are each H; and $R^1$ is aryl or heteroaryl such as phenyl, halophenyl, alkoxy(halo)phenyl, dihalophenyl, arylheteroaryl, alkylphenyl, nitrophenyl, dialkoxyphenyl, alkoxyphenyl, trifluoromethylphenyl, biphenyl, alkylthiophenyl, halo(nitro)phenyl, trialkoxyphenyl, halo(dialkoxy)phenyl, alkylcarbonylaminophenyl, phenylalkyl such as benzyl, 2,3-dihydrobenzofuran

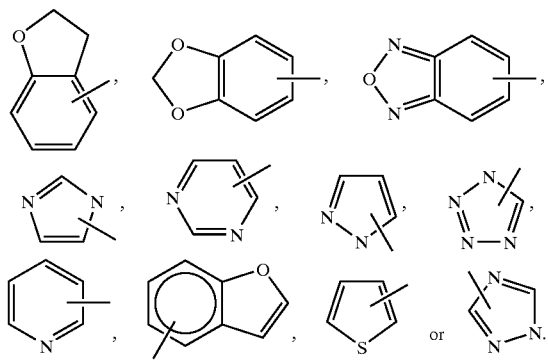

Preferred examples of $R^1$ groups include phenyl, substituted phenyl such as 4-bromophenyl, 4-chlorophenyl, 3-bromophenyl, 3,5-dimethoxyphenyl, 4-methylphenyl, 2,4-dichlorophenyl, 3-nitrophenyl, 2-chlorophenyl, 3-chlorophenyl, 2,5-dimethylphenyl, 2-methylphenyl, 3-methylphenyl, 4-methylphenyl, 2,3-dimethoxyphenyl, 4-trifluoromethylphenyl, 3-trifluoromethoxyphenyl, 4-biphenyl, 2-bromo-4,5-dimethoxyphenyl, 4-methylthiophenyl, 3,4,5-trimethoxyphenyl, 4-fluorophenyl, 2-chloro-3,4-dimethoxyphenyl, 4-nitrophenyl, benzyl, 3-methoxyphenyl, 4-methoxyphenyl, 2-methoxyphenyl, 3-bromo-4-fluorophenyl, 2-fluoro-5-methoxyphenyl, 3-chloro-4-nitrophenyl, 2-fluoro-4-bromophenyl, 3-ethoxyphenyl, 3-trifluoromethylphenyl, 3,5-difluorophenyl, 3,5-dichlorophenyl, 3,5-bistrifluoromethylphenyl, 4-fluorophenyl, 3-trifluoromethylphenyl, 3-(N-pyrrolyl)phenyl, 3-(N-pyrrolidinyl)phenyl, 3-(N-pyrazolinyl)phenyl, 3-(N-imidazolyl)phenyl, phenyltetrazole, 1-(2,4-dihalo-5-alkoxyphenyltetrazol-5-yl, alkylphenyltetrazole, halophenyltetrazole, 1-(2-alkoxy-5-halophenyltetrazol-5-yl, 1-(3-alkyl-4-halophenyl)tetrazol-5-yl, alkoxyphenyltetrazole, alkyl(halo)phenyltetrazole, alkoxy(halo)phenyltetrazole, alkoxy(alkyl)(halo)phenyltetrazole, phenyl-alkyl-pyrazole, alkoxyphenyl-alkyl-pyrazole, halophenyl-alkyl-pyrazole, alkyl(halo)phenyl-alkyl-pyrazole, alkylphenyl-alkyl-pyrazole, alkoxy(halo)phenyl-alkyl-pyrazole, alkoxy(alkyl)phenyl-alkyl-pyrazole, dihalophenyl-alkyl-pyrazole, dialkylphenyl-alkyl-pyrazole, alkoxyphenyl-alkyl-pyrazole, halophenyl-haloalkyl-pyrazole, alkoxyphenyl(alkyl)(halo)pyrazole, phenylpyrimidine, phenyl(halo)pyrimidine, diphenylpyrimidine, halophenyl(halo)pyrimidine, dihalopyrimidine, diphenyl(halo)pyrimidine, halo(phenyl)pyrimidine, dialkyl(halo)pyrimidine, dihalophenylpyrimidine, alkylphenylpyrimidine, alkoxyphenylpyrimidine, alkylphenyl(alkoxy)pyrimidine, dialkylphenyl(alkoxy)pyrimidine, alkyl(halo)phenyl(alkoxy)pyrimidine, alkoxy(halo)phenyl(alkoxy)pyrimidine, dihalophenyl(dialkylamino)pyrimidine, heteroaryl(dihalophenyl)pyrimidine, halophenylpyrimidine, alkoxy(phenyl)pyrimidine, haloalkoxyphenylpyrimidine, phenoxy(phenyl)pyrimidine, heteroaryl(phenyl)pyrimidine, dialkoxyphenylpyrimidine, dialkylphenylpyrimidine, cycloheteroalkyl(phenyl)pyrimidine, alkoxy(halo)phenylpyrimidine, cycloheteroalkyl(dihalophenyl)pyrimidine, halophenyl(alkoxy)pyrimidine, alkyl(halo)phenylpyrimidine, nitrophenylpyrimidine, dihalophenyl(alkoxy)pyrimidine, carboxyphenylpyrimidine, alkylcarbonylphenylpyrimidine, naphthylpyrimidine, alkylthiophenylpyrimidine, phenylpyridine, halophenylpyridine, alkyl(halo)phenylpyridine, dihalophenylpyridine, haloalkoxyphenylpyridine, alkyl(halophenyl)triazole, alkyl(halo)phenyl-(alkyl)-triazole, alkylimidazopyridine

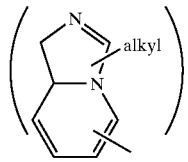

phenylimidazopyridine, halophenylimidazopyridine, dihalophenylimidazopyridine, alkoxyphenylimidazopyridine.

Preferred specific examples or $R^1$ groups include 3-chlorophenyl, 3,5-dichlorophenyl, 3-chloro-4-fluorophenyl, 2,3-dihydrobenzofuran-4-yl, 2-fluoro-5-methoxyphenyl, 3-phenyl-4-fluorophenyl, 3-methoxy-6-fluorophenyl, 2-methoxy-5-chlorophenyl, 3-chloro-5-methoxyphenyl, 3-ethyl-4-fluorophenyl, 1-phenyltetrazol-5-yl, 3-(2-fluorophenylcarbonylamino)pyridin-2-yl, 1-(2,4-dichloro-5-methoxyphenyl)tetrazol-5-yl, 1-(3-chlorophenyl)tetrazol-5-yl, 1-(3-chloro-4-methyl)tetrazol-5-yl, 1-(3-methylphenyl)tetrazol-5-yl, 1-(2-chlorophenyl)tetrazol-5-yl, 1-(2-methoxy-5-chloro)tetrazol-5-yl, 2-(propylcarbonylamino)phenyl, 1-(3-methyl-4-chlorophenyl)tetrazol-5-yl, 1-(2-methoxy-5-chlorophenyl)tetrazol-5-yl, 1-(3-methoxyphenyl)tetrazol-5-yl, 1-(2-methoxy-5-chlorophenyl)tetrazol-5-yl, 1-(3-chlorophenyl)-3-ethylpyrazol-5-yl, 1-(3-fluorophenyl)-3-methylpyrazol-5- yl, 1-(3-methoxyphenyl)-3-methylpyrazol-5-yl, 1-(3,5-dichlorophenyl)-3-methylpyrazol-5-yl, 1-(3-chlorophenyl)-3-ethylpyrazol-5-yl, 1-(3-chloro-4-methylphenyl)-3-methylpyrazol-5-yl, 1-(2,4-dimethylphenyl)-3-methylpyrazol-5-yl, 1-(3-chloro-4-fluorophenyl)-3-methylpyrazol-5-yl, 1-(3-trifluoromethylphenyl)-3-methylpyrazol-5-yl, 1-(3-chlorophenyl)-3-trifluoromethylpyrazol-5-yl, 1-(3-methylphenyl)3-methylpyrazol-5-yl, 1-(3-chlorophenyl)-3-ethylpyrazol-5-yl, 5-(3-chloro-4-fluorophenyl)pyrimidin-4-yl, 5-(2-chlorophenyl)pyrimidin-4-yl, 5-(3-methylphenyl)pyrimidin-4-yl, 5-(3-trifluoromethylphenyl)pyrimidin-4-yl, 5-(2,4-dichlorophenyl)pyrimidin-4-yl, 5-(2,S-dimethylphenyl)pyrimidin-4-yl, 5-(3,4-dichlorophenyl)pyrimidin-4-yl, 5-(2,3-dimethylphenyl)pyrimidin-4-yl, 5-(2-methoxy-5-chlorophenyl)pyrimidin-4-yl, 5-(2-methoxy-5-fluorophenyl)pyrimidin-4-yl, 5-(3-methyl-4-fluorophenyl)pyrimidin-4-yl, 3-(3-methyl-4-fluorophenyl)pyridin-2-yl, 3-(3-chloro-4-fluorophenyl)pyridin-2-yl, 3-(3-trifluoromethoxyphenyl)pyridin-2-yl, 5-(3-chloro-4-fluorophenyl)-2-methoxy-pyrimidin-4-yl, 5-(3-chloro-4-fluorophenyl)-2-dimethylamino-pyrimidin-4-yl, 5-(3-chloro-4-fluorophenyl)-2-morpholinyl-pyrimidin-4-yl, 1-(3-chlorophenyl)-3-methyltriazol-5-yl, 1-(3-chloro-4-methylphenyl)-3-methyltriazol-5-yl, 5-(2,5-dichlorophenyl)pyrimidin-4-yl, 5-(3-chlorophenyl)pyrimidin-4-yl, 5-(3-trifluoromethoxyphenyl)pyrimidin-4-yl, 5-(2-chlorophenyl)-2-methoxypyrimidin-4-yl, 5-(3-chlorophenyl)-2-methoxypyrimidin-4-yl, 5-(3-trifluoromethylphenyl)-2-methoxypyrimidin-4-yl, 5-(2,4-dichlorophenyl)-2-methoxypyrimidin-4-yl, 5-(3-ti methylphenyl)-2-methoxypyrimidin-4-yl, 5-(2,5-dimethylphenyl)-2-methoxypyrimidin-4-yl, 5-(3-methyl-4-fluorophenyl)-2-methoxypyrimidin-4-yl.

Preferred specific examples of Z groups include 2-amino-5-methyl-imidazol-4-yl, 2,5-dimethylimidazol-4-yl, 2-amino-S-ethyl-imidazol-4-yl, 2-amino-5-isopropyl-imidazol-4-yl, 2-aminocarbonylamino-5-methyl-imidazol-4-yl, 5-methyl-imidazol-4-yl, imidazol-4-yl, or 4-methylimidazol-5-yl.

In addition, in accordance with the present invention, a method for preventing, inhibiting or treating angina (stable or unstable), cardiac dysfunction, myocardial necrosis, and arrhythmia is provided, wherein a compound of formula I is administered in a therapeutically effective amount which inhibits sodium/proton exchanger

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various additional branched chain isomers thereof, and the like as well as such groups including 1 to 4 substituents which may be any of the $R^1$ or the $R^1$ substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to one aromatic ring as described for aryl, which include cyclopropyl, cyclobutyl, cyclopentyl, cyclohexyl, cycloheptyl,

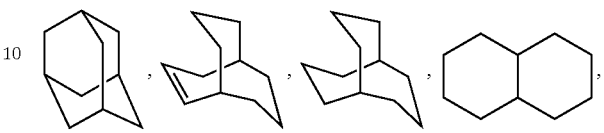

any of which groups may be optionally substituted with 1 to 4 substituents which may be any of the $R^1$ groups, or the $R^1$ substituents set out herein.

The term "cycloalkenyl", as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, 3, or 4 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, aminosulfonylphenyl, arylsulfinyl, arylsulfinylalkyl, arylsulfonylamino or arylsulfonaminocarbonyl or any of the $R^1$ groups or the $R^1$ substituents set out herein.

The term "aralkyl", "aryl-alkyl", or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be independently substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or any of the $R^1$ groups or $R^1$ substituents thereof as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the $R^1$ groups, or the $R^1$ substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl., cycloalkyl, amino, heteroaryl, cycloheteroalkyl, hydroxy, alkanoylamino, alkylamido, arylcarbonylamino, nitro, cyano, thiol, and/or alkylthio, or any of the $R^1$ groups, or the $R^1$ substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", if respectively, and may optionally be substituted as defined above for "alkenyl" and "alkynyl".

Suitable alkylene, alkenylene or alkynylene groups, and $(CH_2)_p$ groups, (where p is 1 to 8, preferably 1 to 5) (which may include alkylene, alkenylene or alkynylene groups) as defined herein, may optionally include 1, 2, or 3 substituents which include any of the $R^1$ groups, or the $R^1$ substituents set out herein.

Examples of alkylene, alkenylene and alkynylene groups include

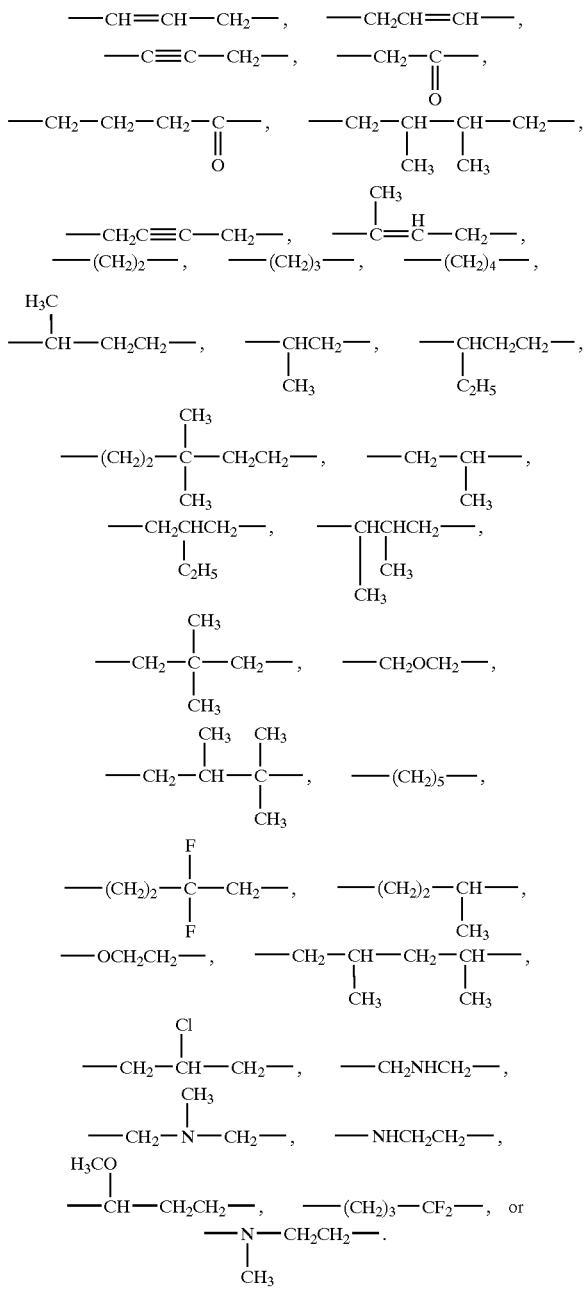

The term "halogen" or "halo" as used herein alone or as part of another group refers to chlorine, bromine, fluorine, and iodine as well as $CF_3$, $CF_3CH_3$, $CF_2H$, $CFH_2$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

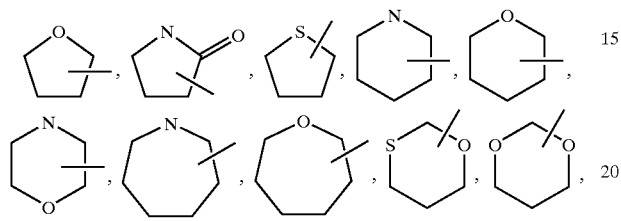

and the like. The above groups may include 1 to 4 substituents such as alkyl, halo, oxo and/or any of the $R^1$ groups, or the $R^1$ substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the $R^1$ groups or the $R^1$ substituents set out above, for example, amino, alkoxy, alkylcarbonylamino, alkylthio, nitro, dialkyl, halo, alkyl(alkanoylamino), alkyl(amino), alkyl(halo), arylaminocarbonylamino(alkyl), alkylcarbonylamino(alkyl), heteroaryl, heteroaryl(alkyl), alkyl, aryl, diaryl, diamino, guanidinyl(alkyl), alkylthio (alkyl), amino(aryl), alkylcarbonylamino(aryl), alkylaminocarbonylamino(alkyl), alkoxycarbonylamino) alkyl), heteroarylalkyl(alkyl), trifluoroalkyl(amino), aminocarbonylamino(alkyl), arylcarbonylamino, arylheteroarylcarbonylamino, aryl(alkyl), alkylcarbonyloxyalkylcarbonylamino, cycloheteroalkyl, cycloheteroalkyl(aryl).

Examples of heteroaryl groups include the following:

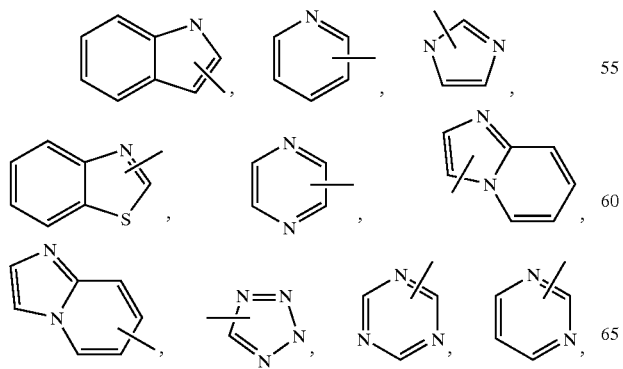

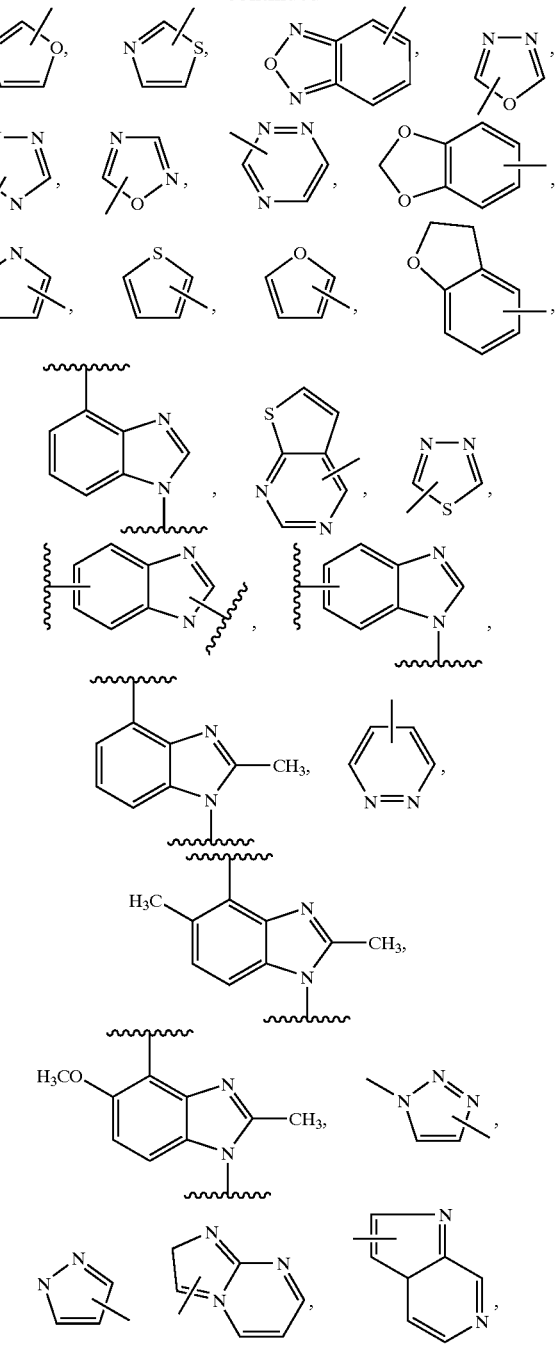

and the like.

Preferred heteroaryl groups are imidazole, oxazole, thiazole, 1,2,3-triazole, 1,2,4-triazole, pyrazole and benzimidazole.

The term "cycloheteroalkylalkyl" as used herein alone or as part of another gorup refers to cycloheteroalkyl groups as defined above linked through a C atom or heteroatom to a $(CH_2)_p$ chain.

The term "heteroarylalkyl" or "heteroarylalkenyl", as used herein alone or as part of another group refers to a heteroaryl ar group as defined above linked through a C atom or heteroatom to a —(CH$_2$)$_p$— chain, alkylene or alkenylene as defined above.

The term "heterocyclyl" as used herein alone or as part of another group refers to heteroaryl or cycloheteroalkyl.

The term "polyhaloalkyl" as used herein refers to an "alkyl" group as defined above which includes from 2 to 9, preferably from 2 to 5, halo substituents, such as F or Cl, preferably F, such as CF$_3$CH$_2$, CF$_3$ or CF$_3$CF$_2$CH$_2$.

The term "polyhaloalkyloxy" as used herein refers to an "alkoxyl" or "alkyloxy" group as defined above which includes from 2 to 9, preferably from 2 to 5, halo substituents, such as F or Cl, preferably F, such as CF$_3$CH$_2$O, CF$_3$O or CF$_3$CF$_2$CH$_2$O.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$–C$_4$)-alkyl- or aryl-sulfonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate, nitrate or maleate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

It should be understood that the present invention includes prodrug forms of the compounds of formula I such as alkylesters of acids or any of the prodrugs for guanidines disclosed in U.S. application Ser. No. 08/641,718, filed May 2, 1996, and in U.S. Pat. No. 5,561,146 which are incorporated herein by reference.

The compounds of the instant invention may, for example, be in the free or hydrate form, and may be obtained by methods exemplified by the following descriptions.

The compounds of formula I may be prepared by the preferred processes described in the following reaction schemes. Exemplary reagents and procedures for these reactions appear hereinafter and in the working Examples.

Compounds of formula I of the invention where Z is aminoimidazole can be prepared from the corresponding carboxylic acids by using the sequence of steps outlined in Scheme 1 set out below. Activation of carboxylic acid 1 with various activating reagents (e.g. 1,1'-carbonyldiimidazole (CDI), thionyl chloride, oxalyl chloride, and the like) (employing a molar ratio of activating agent:acid 1 within the range from about 1:1 to about 10:1) in an organic solvent such as THF or methylene chloride, convert acids 1 to 2. Subsequent treatment of the compound of formula 2 with excess diazomethane in dichloromethane (employing a molar ratio of diazomethane:2 within the range from about 1:1 to about 20:1) gives the compound of formula 3 after treatment with excess hydrochloric acid.

The compound of formula a is treated with acetylguanidine in DMF to provide acetylimidazole of the formula 4 which upon hydrolysis provides compounds of formula IC (T. L. Little, and S. E. Weber, J. Org. Chem. 59, 7299, 1994).

The carboxylic acid of formula 1 can either be commercially available or can be prepared by methods known in the art.

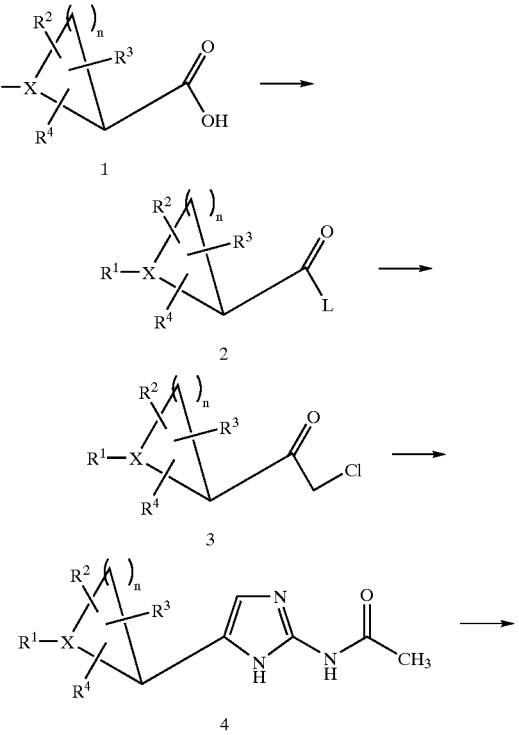

Scheme 1

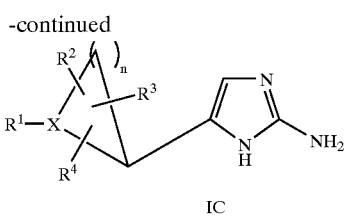

(L=a leaving group such as halide, alkoxy, aryloxy or imidazolyl).

Compounds of formula ID of the invention where Z is aminoimidazole or 5-substituted aminoimidazole can be prepared from the corresponding carboxylic acids by using the sequence of steps outlined in Scheme 2 set out below.

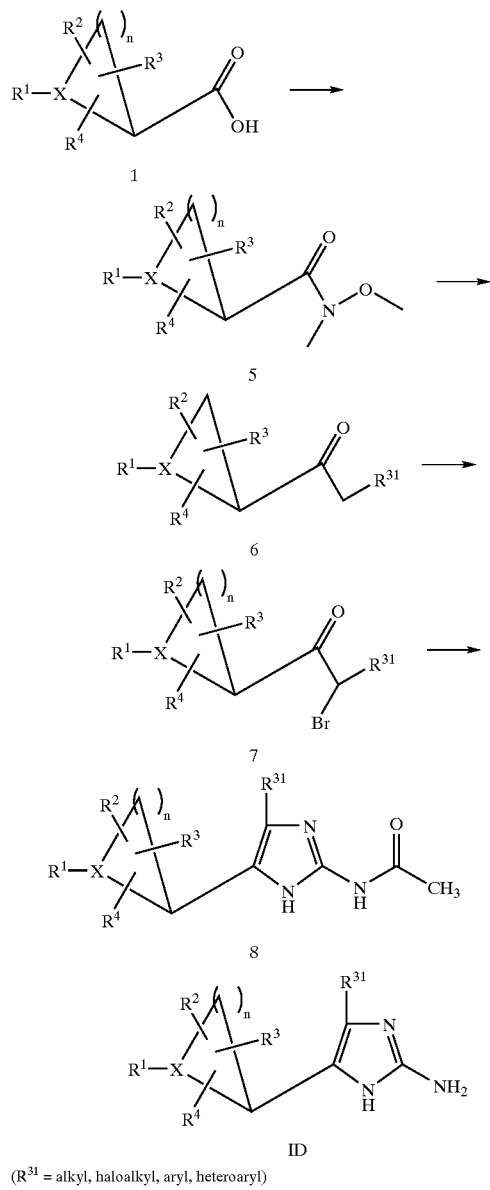

($R^{31}$ = alkyl, haloalkyl, aryl, heteroaryl)

Coupling of the acid 1 with N,O-dimethyl-hydroxylamine using standard coupling reagents such as 1,1'-carbonyldiimidazole or PyBOP, affords the corresponding Weinreb amide 5 which can be converted to ketone 6 upon treatment with a Grignard reagent such as ethyl- or isopropylmagnesium bromide. The ketone 6 can be converted to the α-bromoketone 7 by sequential treatment with lithium bis(trimethylsilyl)amide and N-bromosuccinimide. Alternatively, the bromide 7 can be prepared by treating E with Cu(II)Br$_2$ and hydroxy(tosyloxy)iodobenzene. The bromoketone 7 can be converted to the compound of formula ID via compound a as described for Scheme 1.

Compounds of formula I of the invention where n=1 and X is other than nitrogen (e.g., arylcyclopropane) and Z is aminoimidazole (compounds of formula IE) or imidazole (compounds of formula IF) are prepared from the corresponding α,β-unsaturated ketones by using the sequence of steps outlined in Scheme 3. The unsaturated ketone 12 is prepared by Wittig reaction of aldehyde 9 with the ylide 9a to form 10. Cyclopropanation of 10 to form 11 followed by the formation of silyl enol ether and bromination with N-bromosuccinimide (NBS) affords 12. The bromoketone 12 can be transformed to compounds of formula IE as described for Scheme 1. Alternatively the bromoketone 12 can be converted to the compounds of the formula IF by heating with formamide.

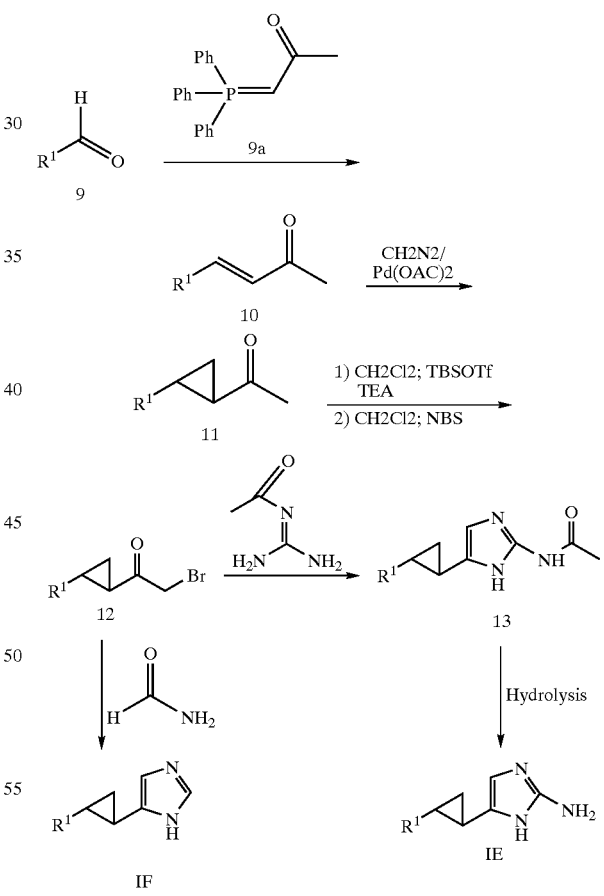

The compounds of formula IG of the invention where X is nitrogen and Z is aminoimidazole can be prepared as outlined in Scheme 4. Compound of formula 14 wherein L is a leaving group (e.g., halide or triflate) is treated with an amine of formula 15 in the presence of a base (e.g., triethylamine, and ethyldiisopropylamine) in an organic solvent (such as DMF) to provide a compound of formula 16. Compound 16 is converted to the desired product IG as described for Schemes 1 or 2. The coupling of 14 and 15 to provide compounds of formula 16 can also be carried out in the presence of palladium catalysts by methods described in the literature (Wagaw, S. et al, J. Amer. Chem. Soc. 1997, Vol. 119, 8458 and references therein).

Compounds of formulae 14 and 15 are commercially available or they can be prepared by methods described in the literature.

Scheme 4

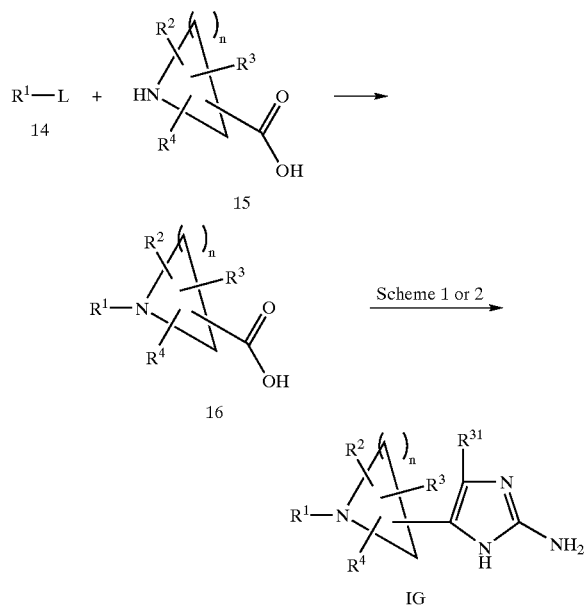

Compounds of formula IH of the invention wherein two of $R^2$, $R^3$ and $R^4$ taken together form a carbocyclic ring and Z is aminoimidazole can be prepared according to Scheme 5. The reaction of cyclopentadiene 17 with an unsaturated ester of formula 18 in the presence of a Lewis acid (diethylaluminum chloride, tin chloride etc.) gives ester of formula 19 which can be hydrolysed to give the corresponding acid and converted to the desired compounds of formula IH by the method described in Schemes 1 or 2. Compounds of formula 17 and 18 are commercially available or they can be prepared by methods described in the literature.

Scheme 5

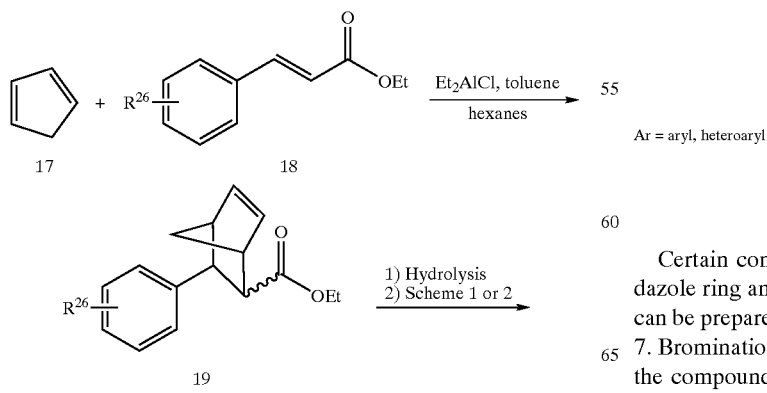

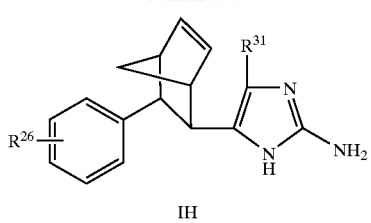

$R^{26}$ = halo, alkyl, aryl, heteroaryl, cyano or nitro.

Certain compounds of the invention of Formula IHH where n=4, X=N, Z=an imidazole ring and $R^1$ is a 4-aryl- or heteroarylpyrazole ring can be prepared as outlined in Scheme 6. Coupling of 20 with diketene affords ketoamides 21 which is converted to IHH upon sequential treatment with various hydrazines and phosphorus oxytrichloride according to the procedure of Bouillon et al (J. P. Bouillon, C. Ates, Z. Janousek, H. G. Viehe, Tetrahedron Lett. 34, 1993, 5075)). Compound of the formula 20 can be synthesized as described by by Jegham, Samir et al (EP0507650).

Scheme 6

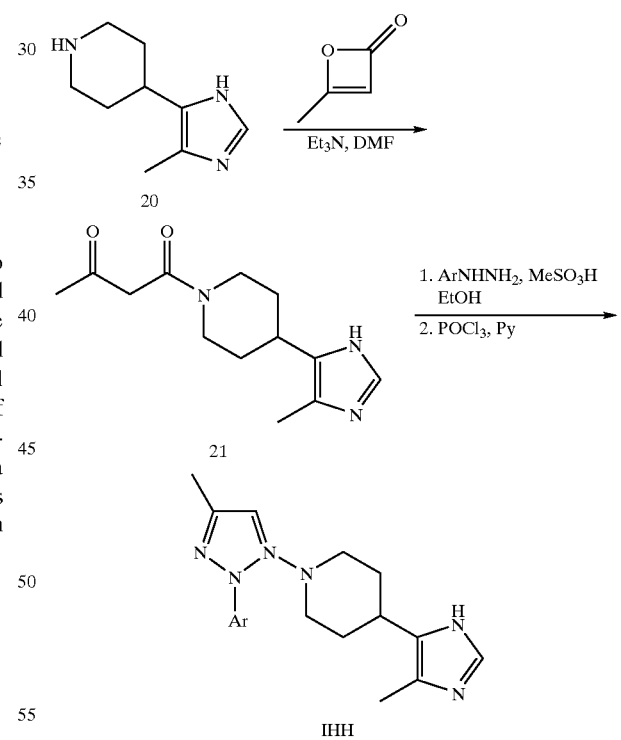

Ar = aryl, heteroaryl

Certain compounds of formula IJ where n=4, Z=an imidazole ring and $R^1$ is a 4-aryl- or 4-heteroaryl-pyrazole ring can be prepared by the sequence of steps outlined in Scheme 7. Bromination of IHH affords 23 which can be converted to the compounds of Formula IJ via a coupling reaction with aryl or heteroaryl boronic acids.

Scheme 7

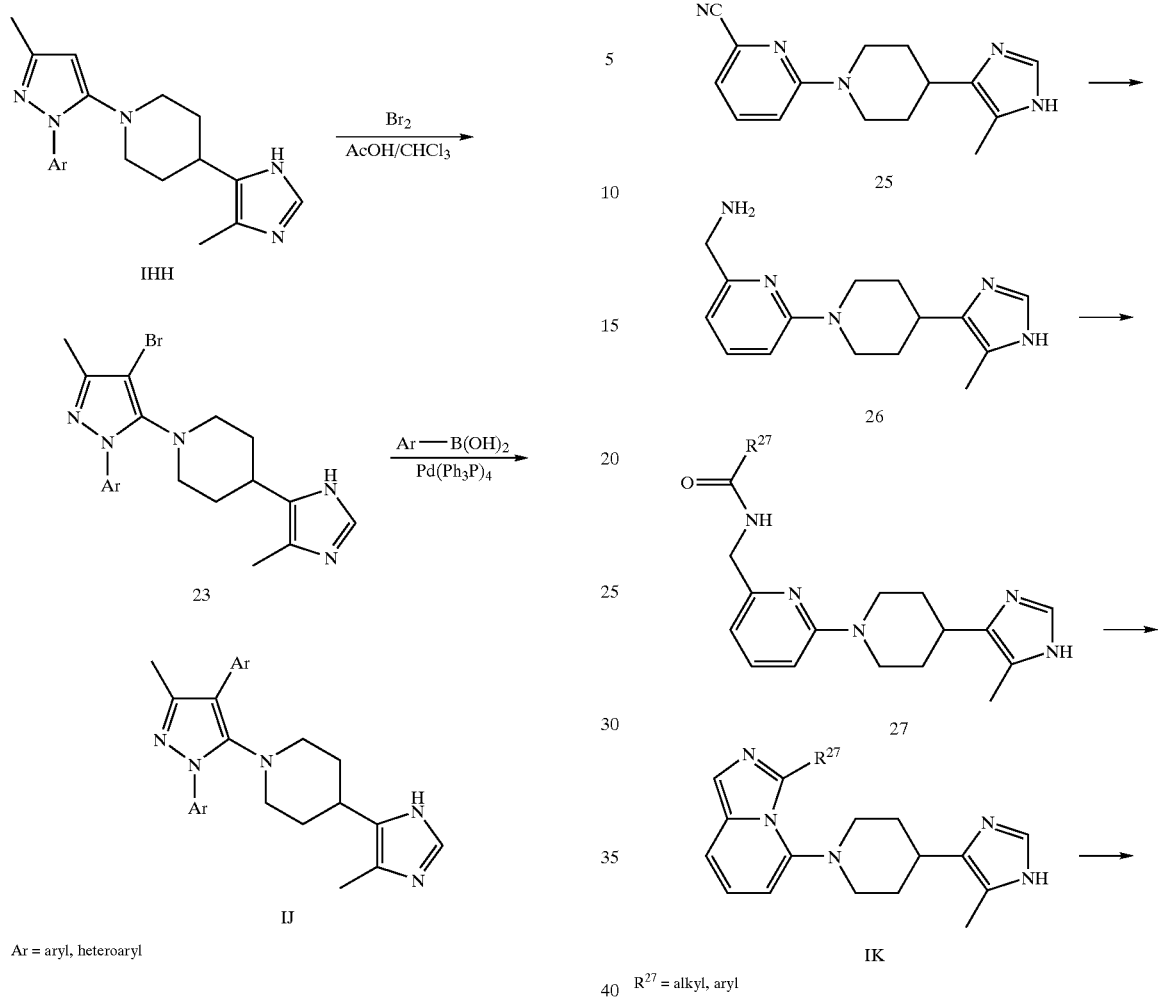

Ar = aryl, heteroaryl

R²⁷ = alkyl, aryl

Compounds of formula IK where n=4, Z=an imidazole ring and R¹ is an imidazopyridine ring are prepared as outlined in Scheme 8. Coupling of compound 20 with 2,6-dibromopyridine affords compound 24 which is coverted to the amide 27 via the nitrile 25 and the amine 26. Cyclization of 27 affords compounds of the formula IK.

Scheme 8

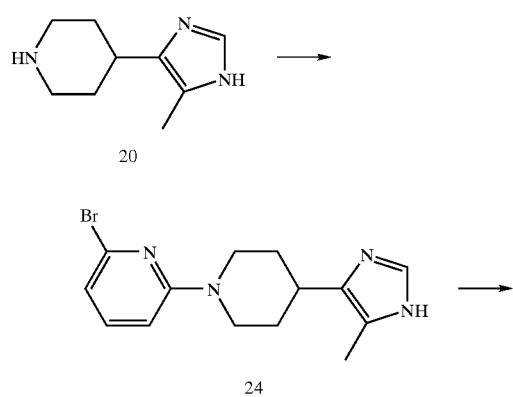

Certain compounds of Formula IL where n=1, Z=aminoimidazole and R¹ is a triazole ring are prepared by the sequence of steps outlined in Scheme 9. The amide 31 can be prepared from ethyl t-butyl fumarate via cyclopropanation (WO 9933460) followed by selective hydrolysis and coupling with N,O-dimethylhydroxylamine as described above for Scheme 2. The amide 31 is converted to the acetylaminoimidazole 32 as outlined in Scheme 2. Hydrolysis of the ester 32 followed by coupling of the resulting acid 33 with various imino esters 33a affords 34. Treatment of 34 with various hydrazines followed by hydrolysis affords compounds of the formula IL.

Scheme 9

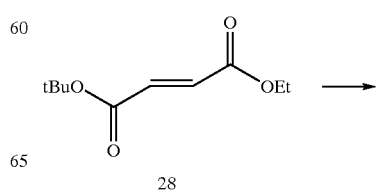

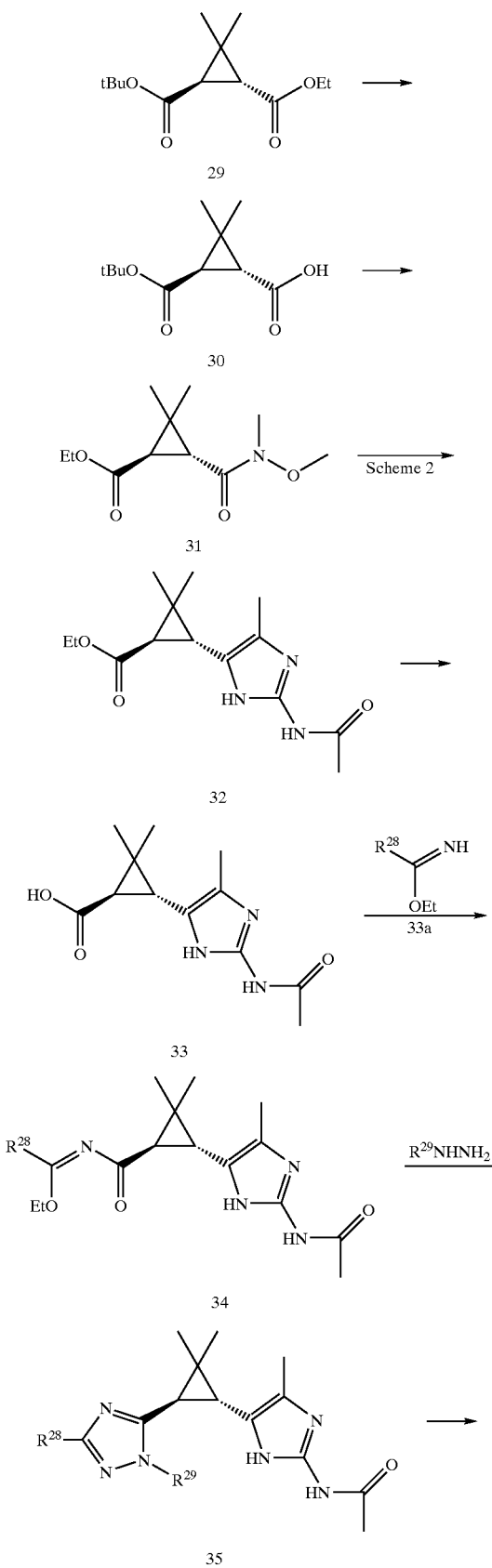

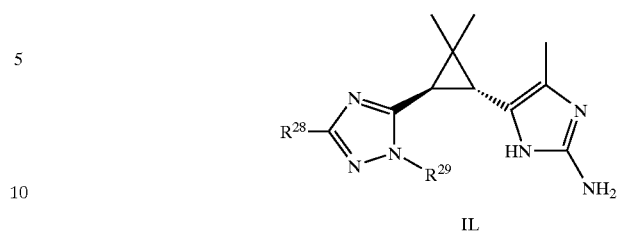

IL $R^{28}$ = alkyl, aryl, heteroaryl
$R^{29}$ = alkyl, aryl, heteroaryl

Compounds of the Formula IM where n=4, Z=an imidazole ring and $R^1$ is tetrazole ring can be prepared as outlined in Scheme 10. The 5-chlorotetrazole intermediate 38 is prepared from the corresponding isothiocyanate 36 via the dichloroimine 37. Coupling of the tetrazole 38 with the piperidine 20 affords the compound of Formula IM.

Scheme 10

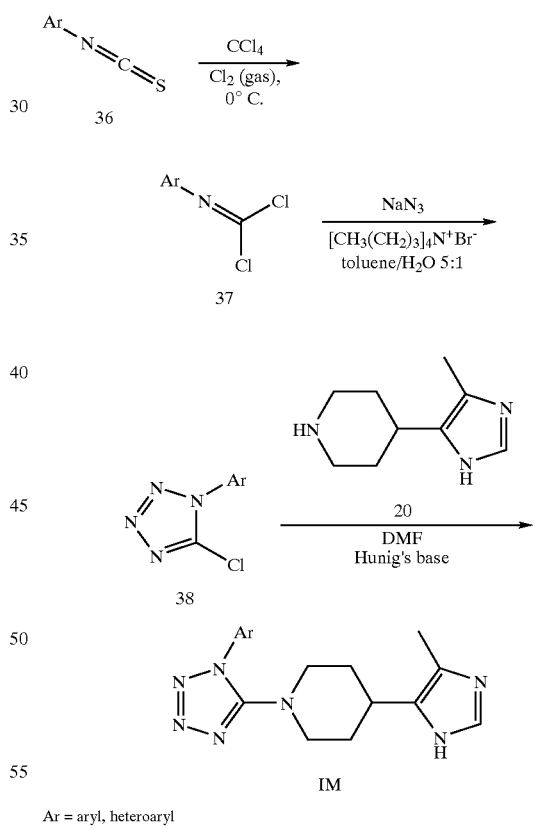

Ar = aryl, heteroaryl

Compounds of the Formula IN where n=4, Z=an imidazole ring and $R^1$ is tetrazole ring can also be prepared as outlined in Scheme 11. Compound 20 is treated with various isocyanates 39 to afford the corresponding urea 40. The urea 40 is converted to the compounds of Formula IN via the triazolyl intermediate 41.

Scheme 11

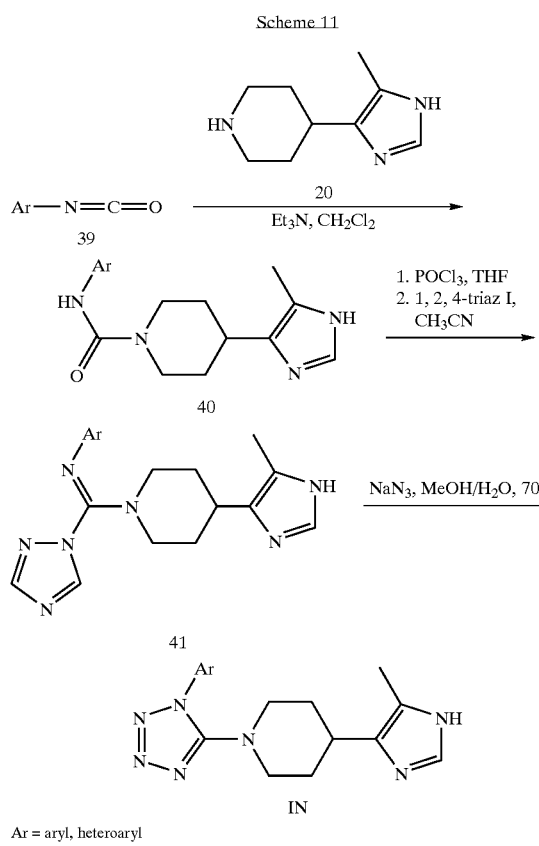

Ar = aryl, heteroaryl

Compounds of the Formula IO where n=4, Z=an imidazole ring and $R^1$ is a pyrimidine ring can be prepared as outlined in Scheme 12. The chloropyrimidines of formula 42 are either commercially available or are they can prepared by methods known in the art.

Scheme 12

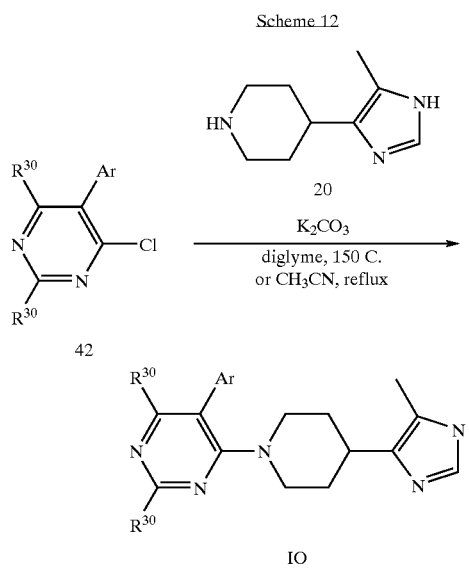

Ar = aryl, heteroaryl
$R^{30}$ = alkyl, halo,

Certain compounds of the Formula IP where n=4, Z=an imidazole ring and $R^1$ is a pyrimidine ring are prepared as outlined in Scheme 13. The bromide 44 is prepared by coupling 43 with 20. Coupling of the bromide 44 with various aryl or heteroaryl boronic acids in the presence of a Pd(0) catalyst affords 45 which is converted to the compounds of the Formula IP by treatment with nucleophile NuH or NuM.

Scheme 13

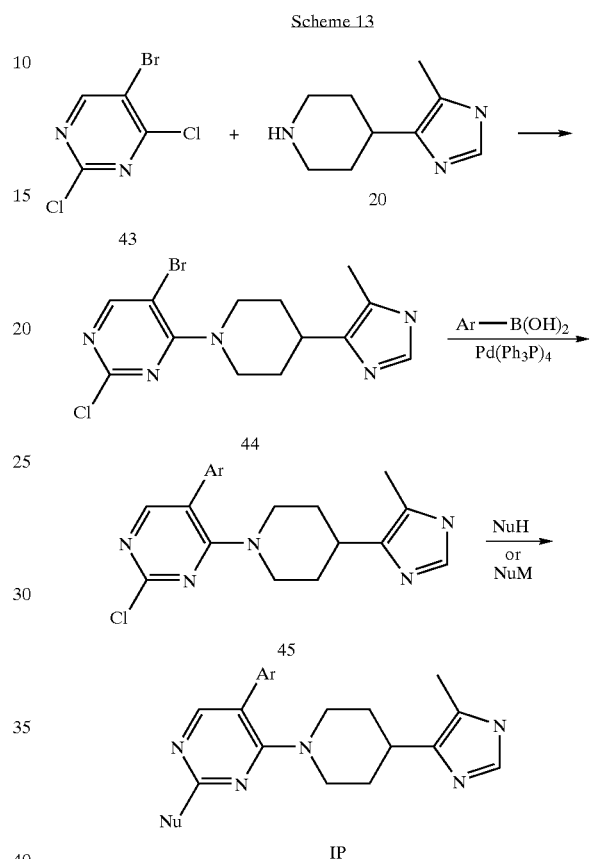

Ar = aryl, heteroaryl
Nu = alkyl-O, alkylNH, (alkyl)$_2$N, alkyl-S, or alkyl
M = Li, MgBr.

Certain compounds of the Formula IQ where n=4, Z=an imidazole ring and $R^1$ is a pyrimidine ring are also prepared as outlined in Scheme 14. Coupling of 20 with 46 affords 47 which is converted as in Scheme 13 to the compounds of the Formula IQ.

Scheme 14

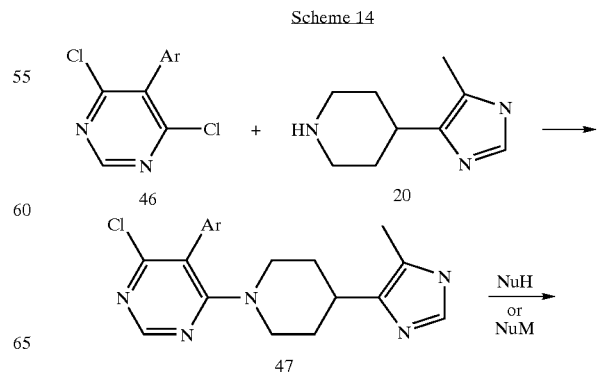

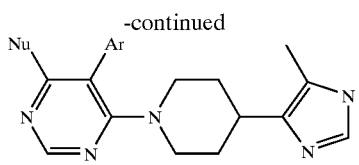

IQ

Ar = aryl, heteroaryl
Nu = alkyl-O, alkylNH, (alkyl)$_2$N, alkyl-S, or alkyl
M = Li, MgBr.

Certain compounds of formula IS where Z is an aminoimidazole are also prepared from the corresponding imidazoles IR (which may be prepared as outlined in Schemes 3, 6, 7, 8, 10, 11, 12, 13 and 14) upon the 2 step amination procedure of Commercon et al (A.

Commercon, C. Gueremy, TetrahedronLett. 12, 1993, 1419) outlined in Scheme 15.

Scheme 15

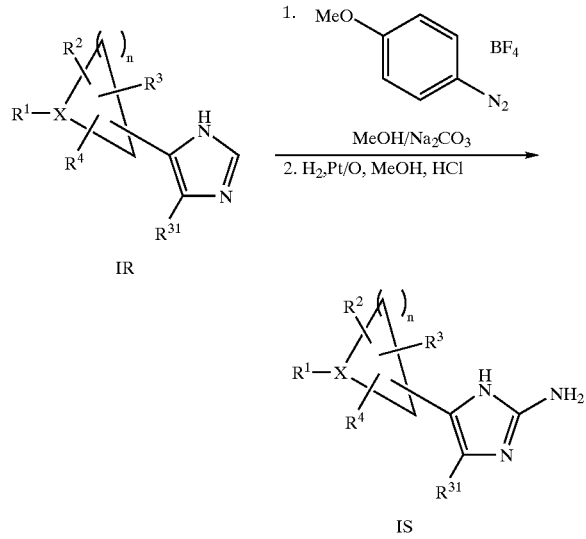

Compounds of formula I wherein Z is an imidazole other than the imidazolyl or aminoimmidazolyl groups described above can be prepared from the carboxylic acid precursor by methods known in the art such as those described in Novel Functional M$_1$ Selective Muscarinic Agonists. Synthesis and Structure—Activity Relationships of 3-(1,2,5-Thiadiazolyl)-1,2,5,6-tetrahydro-1-methylpyridines. Sauerberg, P. et al, J. Medicinal Chemistry, 1992, Vol. 35, 2274–2283;

Tetrahydropyridyloxadiazoles:Semirigid Muscrinic Ligands, Showell, G. A. et al, J. Medicinal Chemistry, 1991, Vol. 34, 1086–1094;

Azabicyclic Esters and Oxadiazoles as Receptor Ligands, Orlek, et al, J. Medicinal Chemistry, 1991, Vol. 34, 2726–2735, and references therein.

Other compounds of formula I wherein Z is imidazolyl or a substituted imidazolyl can be prepared according to methods described in the literature such as those in Comprehensive Heterocyclic Chemistry, Vol. 5, part 4A, Editor Kevin T. Potts, Pergamon Press;

Synthesis and Reactions of Lithiated Monocyclic Azoles Containing Two or More Heteroatoms, Part IV, Imidazoles, Iddon, B; Ngochindo, RI, Heterocycles 1994, Vol. 38, 2487–2568;

Advances in Imidazole Chemistry, Grimmett, M. R., Advances in Heterocyclic Chemistry, 1970, Vol. 12, 103–183;

Bioisosteric Prototype Design of Biaryl Imidazolyl and Triazolyl Competitive Histamine H2-Receptor Antagonists, Lipinski, C. A., LaMattina, J. L., Oates, P. J., J. Medicinal Chemistry 1986, Vol. 29, 2154–2163.

The above schemes as shown fix the position of the heterocyclic (e.g. imadazole) moiety relative to the group B. However, it will be understood that these schemes apply to preparing compounds of formula I of the invention wherein the heterocyclic moiety may be attached at any of the ring positions of the group A.

The compounds of formula I of the invention exhibit Na$^+$/H$^+$ exchange inhibitory activity, and hence, are useful for treating or preventing disorders caused by intracellular acidosis during myocardial ischemia, such as cardiac dysfunction, myocardial necrosis, arrhythmia, reperfusion injury, and the like which are observed in ischemic heart diseases (e.g., myocardial infarction and angina pectoris).

Thus, compounds of formula I of the invention may be used as antiischemic agents, i.e., for the treatment of ischemic conditions including acute and chronic ischemic conditions such as myocardial ischemia, cerebral ischemia, peripheral vascular diseases or disorders including lower limb ischemia, peripheral atherosclerotic disease, tissue ischemia and intermittent claudication, LeRiches Syndrome and Raynaud's disease. Thus, a composition containing one (or a combination) of the compounds of this invention, may be administered to a species of mammal (e.g., humans, dogs or cats) suffering from an ischemic condition or any of the conditions set out above.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the Na$^+$/H$^+$ exchange inhibiting activity of the compounds of this invention, these compounds are also useful in the treatment of cardiovascular disorders. For example, compounds of the present invention are useful as therapy for congestive heart failure, therapy for peripheral vascular disorders (e.g., intermittent claudication and Raynaud's Disease), therapy for hypertension, as antianginal agents, as antifibrillatory agents, and in limiting myocardial infarction.

Compounds of the present invention are additionally expected to be useful in the treatment of cerebral ischemia (e.g., stroke).

As a result of the Na/H exchange inhibiting activity, the compounds of this invention can also be used for the treatment of diseases associated with proliferation of smooth muscle cells, mesangial cells, and fibroblasts. Such diseases include restenosis after angioplasty, renal fibrosis, atherosclerosis, hepatic fibrosis, prostate hypertrophy, pulmonary fibrosis and glomerular nephrosclerosis.

Other uses for compounds of this invention which inhibit Na/H exchange include treatments for diseases such as cardiac hypertrophy, ischemic/reperfusion injury associated with organ transplantation, and other surgical procedures such as percutaneous transluminal coronary angioplasty (PTCA).

Due to their Na/H exchange inhibiting properties, compounds of this invention can also be used for CNS disorders associated with cerebral ischemia such as cerebral infarction, cerebral edema and like. Additionally, they can be used for ischemia and ischemia-reperfusion injury resulting from shock and trauma.

The compounds of the invention are also anti-thrombotic agents and antiproliferative agents and are also useful in treating renal disease.

The compounds of the invention are also dual inhibitors of NHE-1 and NHE-3 and thus can be used as cardioprotectants for the treatment of heart disease, whilst also improving renal function by protecting against renal damage, or reversing hypertension by a direct modulation of sodium resorbtion in the kidney. As dual inhibitors, the compounds of the invention are also useful in a combination of therapies, for example, hypertension in patients with acute coronary syndromes, MI, recovery from MI and chronic stable angina. They are also useful for heart failure when an anti-hypertensive or diuretic agent is required for treatment.

Compounds of this invention can be additionally used for the treatment of diabetes mellitus and other diabetic complications and for lowering serum lipids such as lowering LDL-cholesterol.

Where desired, the compounds of this invention may be used in combination with one or more other antianginal and cardioprotective agents, one or more diuretic agents, one or more antithrombotic or anticoagulant agents, one or more anti-platelet agents or platelet aggregation inhibitors, one or more prothrombolytic agents, one or more antihypertensive agents, one or more antiatherosclerotic agents, one or more antidiabetic agents, one or more hypolipidemic agents or lipid-lowering agents, one or more mineralocorticoid receptor antagonists, and/or one or more growth hormone secretagogues.

The compounds of the invention can be used or formulated in combination with one or more antianginal agents such as long-acting nitrates, for example, nitroglycerin, isosorbide mononitrate, and isosorbide dinitrate.

The compounds of the invention can be used or formulated in combination with one or more cardioprotective agents such as digitalis and oriabion.

The compounds of this invention can be used or formulated in combination with one or more diuretics such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid, tricrynafen, torasemide, idapamide, chlorthalidone, furosemide, musolimine, bumetamide, triamterene, amiloride and spironolactone and salts of such compounds.

Such combination products if formulated as a fixed dose employ the compounds of this invention within the dose range described above and the other pharmaceutically active agent within its approved dose range.

The compounds of the invention can be used or formulated in combination with one or more anti-platelet agents or platelet aggregation inhibitors or P2Y(AC) antagonists such as clopidogrel, ticlopidine and CS-747, one or more GPIIb/IIIa blockers such as abciximab (Reopro®), eptifibatide (Integrilin®), and tirofiban (Aggrastat), eptifibalide, anagrelide, one or more thromboxane receptor antagonists such as ifetroban, one or more PAI-1 inhibitors such as XR-330 and T-686, one or more inhibitors of α-2-antiplasmin such as anti-α-2-antiplasmin antibody, one or more prostacyclin mimetics, one or more phosphodiesterase inhibitors, such as dipyridamole or cilostazol, one or more (PDE) inhibitors in combination with thromboxane receptor antagonists/thromboxane A synthetase inhibitors (such as picotamide), one or more serotonin-2-receptor antagonists (such as ketanserin), or one or more fibrinogen receptor antagonists.

The compounds of the invention may be used or formulated in combination with one or more antithrombotic or anticoagulant agents such as warfarin, lower molecular weight heparins, such as enoxaparin (Lovenox®), one or more Factor Xa inhibitors and/or Factor VIIa inhibitors, such as compounds disclosed in pending U.S. application Ser. No. 09/478,632 filed Jan. 6, 2000, and its continuation-in-part appication filed Aug. 7, 2000 and U.S. applicatin Ser. No. 09/496,571, filed Feb. 2, 2000.

Compounds of the present invention are also useful in combination with anti-arrhythmic agents such as for atrial fibrillation, for example, amiodarone or dofetilide.

The compounds of the present invention may also be used in combination with β-adrenergic agonists such as albuterol, terbutaline, formoterol, salmeterol, bitolterol, pilbuterol, or fenoterol, as well as with anticholinergics such as ipratropium bromide, anti-inflammatory cortiocosteroids such as beclomethasone, triamcinolone, budesonide, fluticasone, flunisolide or dexamethasone, and anti-inflammatory agents such as cromolyn, nedocromil, theophylline, zileuton, zafirlukast, monteleukast and pranleukast.

The antiatherosclerotic agent suitable for use herein may be one or more ACAT inhibitors such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The compounds of structure I may be used or formulated in combination with one or more hypolipidemic agents or lipid-lowering agents including one or more MTP inhibitors, one or more HMG CoA reductase inhibitors, one or more squalene synthetase inhibitors, one or more fibric acid derivatives, one or more lipoxygenase inhibitors, one or more cholesterol absorption inhibitors, one or more ileal $Na^+$/bile acid cotransporter inhibitors, one or more upregulators of LDL receptor activity, one or more bile acid sequestrants, and/or nicotinic acid and derivatives thereof.

MTP inhibitors employed herein include MTP inhibitors disclosed in U.S. Pat. No. 5,595,872, U.S. Pat. No. 5,739, 135, U.S. Pat. No. 5,712,279, U.S. Pat. No. 5,760,246, U.S.

Pat. No. 5,827,875, U.S. Pat. No. 5,885,983 and U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

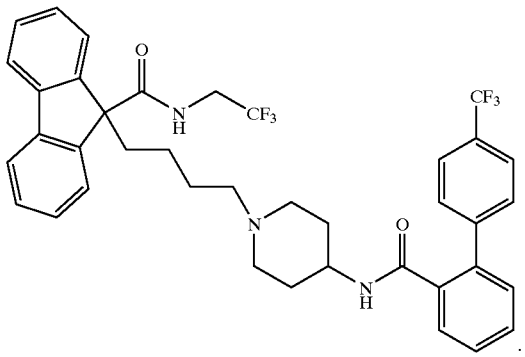

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (atavastatin or rosuvastatin) (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322, and statins, disclosed in U.S. provisional applications No. 60/211,594 filed Jun. 15, 2000, and No. 60/211,595 filed Jun. 15, 2000.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 2, 243–249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, itavastatin and visastatin.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The antidiabetic agent which may be optionally employed in combination with the compound of formula I may be 1,2,3 or more antidiabetic agents or antihyperglycemic agents including insulin secretagogues or insulin sensitizers, which may include biguanides, sulfonyl ureas, glucosidase inhibitors, PPAR γ agonists, such as thiazolidinediones, aP2 inhibitors, PPAR α/γ dual agonists, dipeptidyl peptidase IV (DP4) inhibitors, SGLT2 inhibitors, and/or meglitinides, as well as insulin, and/or glucagon-like peptide-1 (GLP-1).

The antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1 (7–36) amide, GLP-1 (7–37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Preferred are metformin/glyburide combinations such as disclosed in U.S. Ser. No. 09/432,465 filed Nov. 3, 1999, and U.S. Ser. No. 09/460,920 filed Dec. 14, 1999.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an SGLT2 inhibitor such as disclosed in U.S. provisional application No. 60/158,773, filed Oct. 12, 1999, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. provisional application No. 60/127,745, filed Apr. 5, 1999, employing dosages as set out herein. Preferred are the compounds designated as preferred in the above applications.

The antidiabetic agent may be a DP4 inhibitor such as disclosed in Provisional Application 60/188,555 filed Mar. 10, 2000, WO99/38501, WO99/46272, WO99/67279 (PROBIODRUG), WO99/67278 (PROBIODRUG), WO99/61431 (PROBIODRUG), NVP-DPP728A (1 [[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996)) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor beta drug and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The growth hormone secretagogue suitable for use herein includes those described in U.S. Ser. No. 09/417,180 filed Oct. 12, 1999.

The thyroid receptor beta compound which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers, centrally acting agents, and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986);

40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31-2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl)disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril, moexipril, cilazopril, delapril, or pentopril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, U.S. Pat. No. 5,552,397, U.S. Pat. No. 5,504,080, U.S. Pat. No. 5,612,359,U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Calcium channel blockers suitable for use herein include verapamil, nifedipine, diltiazem, felodipine, nisoldipine, isradipine, nicardipine and amlodipine besylate (Norvasc®).

β-blockers suitable for use herein include one or more of atenolol, carvedilol, nadolol, propranolol and sotalol.

Examples of most preferred antihypertensive agents suitable for use herein include omapatrilat (Vanlev®) gemopatrilat, amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Mineralocorticoid receptor antagonists suitable for use herein include spironolactone and epherenone.

Antiosteoporosis agents suitable for use herein in combination with the compounds of formula I of the invention include parathyroid hormone or bisphosphonatesi, such as MK-217 (alendronate) (Fosamax®). Dosages employed will be as set out in the PDR.

Unless otherwise specified, the various components employed in combinations of the invention with compounds of formula I will be employed in dosages and amounts as described in the PDR, and/or patents and other references disclosing such compounds.

The compounds of the invention can be administered orally or parenterally such as subcutaneously or intravenously, as well as by inhalation and nasal application, rectally, transdermally, or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 500 mg, preferably from about 5 to about 200 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound or mixture of compounds of formula I. They may be compounded in conventional matter with a physiologically acceptable vehicle or carrier, excipient, binder, preservative, stabilizer, flavor, etc., as called for by accepted pharmaceutical practice.

The following abbreviations are employed herein-before and in the Examples:
Ph=phenyl
Bn=benzyl
t-Bu=tertiary butyl
Me=methyl
Et=ethyl
TMS=trimethylsilyl
TMSN$_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
Et$_2$O=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
EDC or DCE=1,2 dichloroethane
HMPA=hexamethyl phosphoric triamide
HOAc or AcOH=acetic acid TFA=trifluoroacetic acid
DIEA or Hunig's Base or i-Pr$_2$NEt=N,N-diisopropyl-ethylamine
TEA or Et$_3$N=triethylamine
NMM=N-methyl morpholine
DMAP=4-dimethylaminopyridine
NaBH$_4$=sodium borohydride
NaBH(OAc)$_3$=sodium triacetoxyborohydride
DIBAL or DIBALH=diisobutyl aluminum hydride
LiAlH$_4$=lithium aluminum hydride
n-BuLi=n-butyllithium
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)$_2$=sodium hexamethyldisilazide or sodium bis(trimethylsilyl)amide
Ph$_3$P=triphenylphosphine
Pd(OAc)$_2$=Palladium acetate
(Ph$_3$P)$_4$Pd$^o$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
DCM=dichloromethane
PyBOP=benzotriazole-1-yl-oxy-trispyrrolidino-phosphonium hexafluorophosphate
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance mp=melting point The following examples and preparations describe the manner and process of making and using the invention and are of preferred embodiments of the invention. It should be understood that there may be other embodiments which fall within the spirit and scope of the invention as defined by the claims appended hereto.

EXAMPLE 1

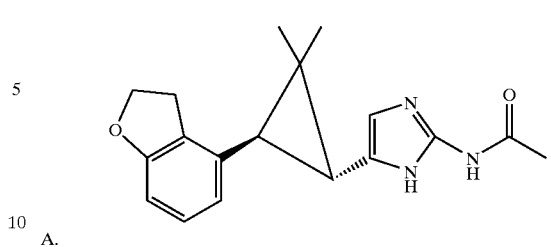

A.

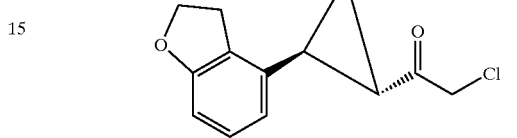

A solution of oxalyl chloride (2M in dichloromethane, 2.15 mL) was added to a solution of

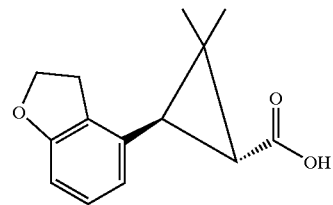

(1.0 g, prepared as described in WO 9933460) in 10 mL dichloromethane followed by the addition of 2 drops DMF. The reaction mixture was stirred at RT for 1 h and concentrated to afford the corresponding acid chloride. This material was dissolved in 5 mL dichloromethane and treated with excess diazomethane in ether at RT. Stirring was continued at RT for 3 h and the mixture was concentrated to give the corresponding diazomethyl ketone. This compound was dissolved in 5 mL dichloromethane followed by the addition of HCl in ether (2M, 20 mL) and the reaction mixture was stirred at RT for 18 h. The reaction mixture was concentrated to afford the title compound as a brown gummy solid (1.2 g).

B.

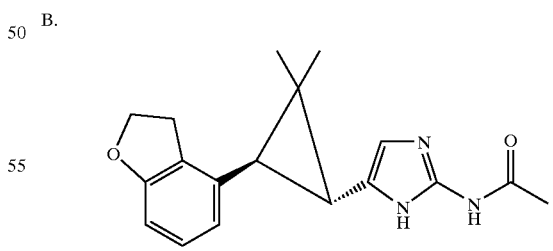

A mixture of the above title compound A (100 mg), acetyl guanidine (114 mg) in 5 mL DMF was heated at 100° C. for 18 h. The solvent was evaporated and the crude product was purified by preparative HPLC (C18 column/water-methanol-trifluoroacetic acid 90:10:0.1 to 10:90:0.1 gradient) to afford the title compound as a light yellow solid; MS m/z 312 (M+H)$^+$.

EXAMPLE 2

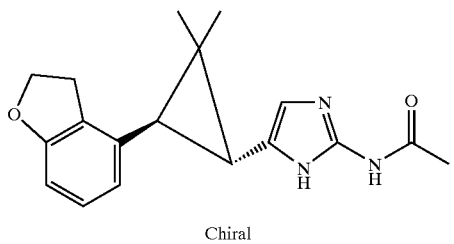

Chiral

This compound was prepared from the corresponding chiral acid (prepared as described in WO 9933460) in a manner similar to that described for Example 1; MS m/z 312 (M+H)+.

EXAMPLE 3

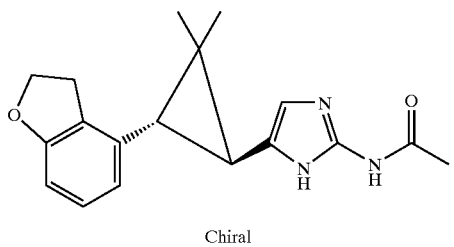

Chiral

This compound was prepared from the corresponding chiral acid (prepared as described in WO 9933460) in a manner similar to that described for Example 1, MS m/z 312 (M+H)+.

EXAMPLE 4

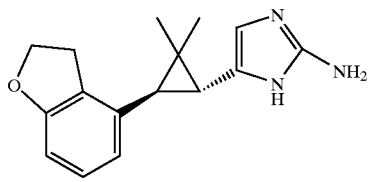

To a mixture of the title compound of Example 1 (40 mg), methanol (2 mL) and water (2 mL) was added 5 drops of concentrated sulfuric acid and the reaction mixture was heated under reflux for 18 h. The mixture was concentrated and the crude product was purified by preparative HPLC as described in example 1 part H to give 24 mg of the title compound as a TFA salt, off-white solid; MS m/z 270 (M+H)+.

EXAMPLE 5

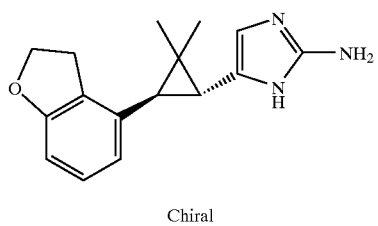

Chiral

This compound was prepared from the title compound Example 2 by using the procedure described in Example 4; MS m/z 270 (M+H)+.

EXAMPLE 6

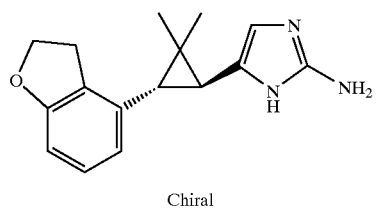

Chiral

This compound was prepared from the title compound Example 3 by using the procedure described in Example 4; MS m/z 270 (M+H)+.

EXAMPLE 7

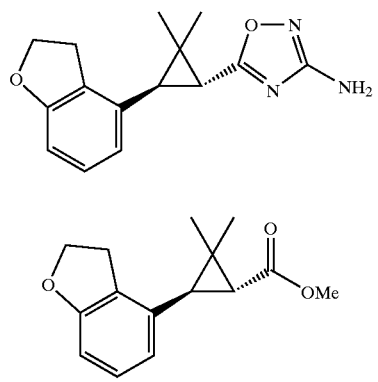

A.

To a stirred solution of

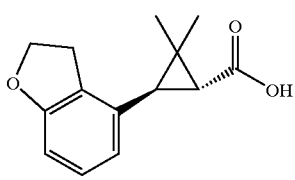

(500 mg, 2.15 mmol) in methanol (10 mL) added thionyl chloride (5.12 g) dropwise. The reaction mixture was stirred for 30 minutes and concentrated to afford 490 mg (94% crude yield) of the title compound as a brown gum.

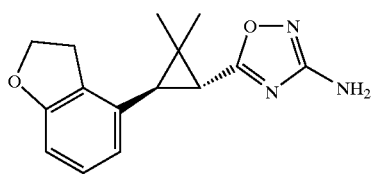

A mixture of the ester from step A (100 mg, 0.41 mol) and hydroxyguanidine in MeOH (2 mL) was refluxed for 18 hrs. Then the solvent was evaporated and the crude product was purified by preprative HPLC as described for Example 1 to give the title compound as TFA salt (60 mg, 54%); $^1$H NMR δ (CDCl$_3$) 7.07 (m, 1H), 6.71 (d, J=6.0 Hz, 1H), 6.60 (d, J=6.0 Hz, 1H), 4.98 (Broad peak), 4.62 (m, 2H), 3.25 (m, 1H), 3.10 (m, 1H), 2.78 (d, 1H), 2.52 (d, 1H), 2.41 (s, 3H), 1.35 (s, 3H), 1.03 (s, 3H).

EXAMPLE 8

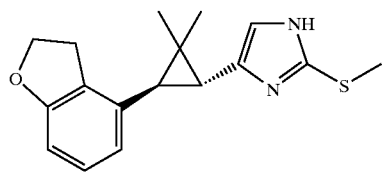

A mixture of the chloromethyl ketone from step A Example 1 (100 mg, 0.38 mmol), S-methylisothiouronium sulfate (126 mg, 0.45 mmol) and sodium acetate (93 mg, 1.14 mmol) in EtOH (20 mL) were refluxed for 18 hours. The solvent was evaporated and the crude product was purified by preparative HPLC as described for Example 1 to give the title compound (30 mg, 27%) as clear gum; $^1$H NMR δ (CDCl$_3$) 7.03 (m, 1H), 6.93 (s, 1H), 6.68 (d, J=7.6 Hz, 1H), 6.54 (d, J=8.0 Hz, 1H), 4.58 (m, 2H), 3.18 (m, 1H), 3.06 (m, 1H), 2.66 (s, 3H), 2.16 (m, 2H), 1.09 (s, 3H), 0.92 (s, 3H).

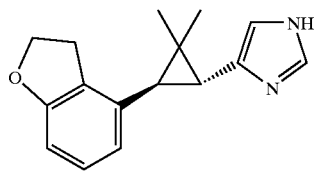

A mixture of Raney nickel (ca. 2 mL of the suspension), the title compound from Example 8 (15 mg, 0.050 mmol) in EtOH (5 mL) and water (5 mL) was stirred at RT for 2 h, filtered through Celite and the solvent was evaporated. The crude product was purified by preparative HPLC as described for Example 1 to give the title compound (10 mg, 83%) as white powder (1yophilate); MS m/z 255 (M+H)$^+$.

EXAMPLE 10

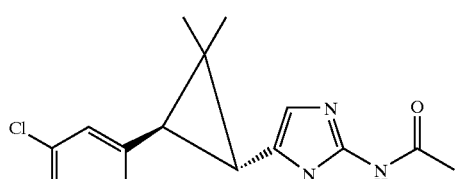

A.

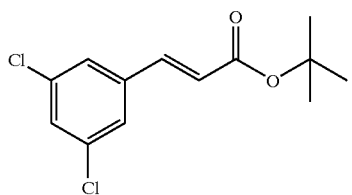

To a solution of tert-butyldiethylphosphonoacetate (6.94 g, 27.5 mmol) in THF (50 ml) at 0° C. was added slowly sodium hexamethyldisilazide (NaHMDS) (27.5 ml, 27.5 mmol). The resulting solution was warmed to 25° C. and stirred for 30 minutes. After cooling the reaction mixture to 0° C., a solution of 3,5-dichlorobenzaldehyde (4.38 g, 25 mmol) in THF (25 ml) was slowly added. The reaction mixture was warmed to 25° C. and stirred overnight. The reaction mixture was poured onto saturated NH$_4$Cl/EtOAc. The aqueous layer was extracted 3 times with EtOAc. The combined organics were washed with brine, dried over Na$_2$SO$_4$, and concentrated in vacuo. Purification of the crude residue by silica gel chromatography (9:1 hexanes-EtOAc) provided 5.19 g (77%) of title compound in the form of a white solid.

B.

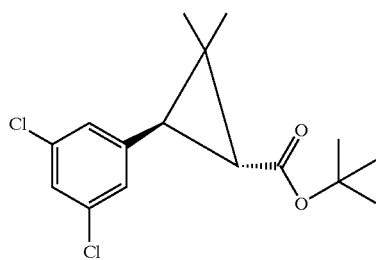

To a suspension of isopropyltriphenylphosphonium iodide (6.48 g, 15 mmol) in THF (45 ml) at -78° C. was added n-BuLi (2.5 M in hexanes, 6.6 ml, 16.5 mmol). The resulting mixture was warmed to 0° C. and stirred 30 minutes. To the reaction mixture was added a solution of the compound from step A (4.11 g, 15 mmol) in THF (30 ml). The reaction mixture was stirred 2 hours at 0° C., then slowly warmed to 25° C. and stirred overnight. The reaction mixture was poured onto 10% H$_2$SO$_4$/EtOAc. The aqueous layer was extracted 3 times with EtOAc. The combined organic layer was washed with saturated NaHCO$_3$, brine, and H$_2$O, dried over NaSO$_4$, and concentrated in vacuo. The crude residue was used without further purification, $^1$H NMR δ (CDCl$_3$) d 7.32 (1H, s) 7.30–7.27 (2H, m), 2.72 (1H, d, J=8.9 Hz), 2.28 (1H, d, J=8.9 Hz), 1.71 (9H, s), 1.51 (3H, 9), 1.08 (3H, s).

C.

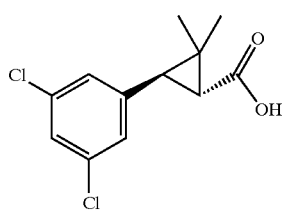

The crude ester from Step B (ca. 25 mmol) was dissolved in 1:1 trifluoroacetic acid-CH₂Cl₂ (25 ml) at 25° C. The resulting solution was stirred 1 hour at 25° C. The reaction mixture was concentrated in vacuo. The crude residue was partitioned between 10% NaOH and Et₂O. The aqueous layer was extracted 3× with ether. The pH of the aqueous layer was adjusted to 4 and was extracted 10× with EtOAc. The combined organic layer was dried over MgSO₄ and concentrated in vacuo to afford 2.32 g (71% over two steps) of a white solid; $^1$H NMR δ (CDCl₃) 7.32 (1H, s) 7.30–7.27 (2H, m), 2.77 (1H, d, J=8.9 Hz), 2.20 (1H, d, J=8.9 Hz), 1.48 (3H, s), 1.05 (3H, s).

D.

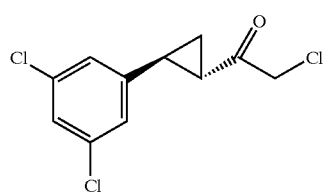

This compound was prepared from the part C compound by the method described in Example 1 part A.

E.

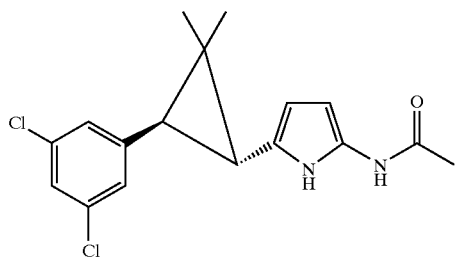

This compound was prepared from the part D compound as described in Example 1 part B; MS m/z 338 (M+H)⁺.

EXAMPLE 11

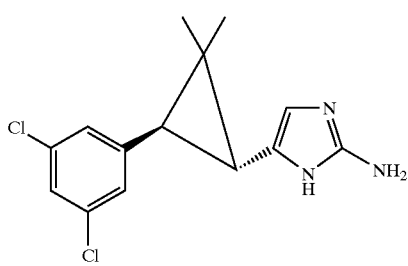

This compound was prepared from the title compound Example 10 by using the procedure described in Example 4; MS m/z 296 (M+H).

EXAMPLE 12

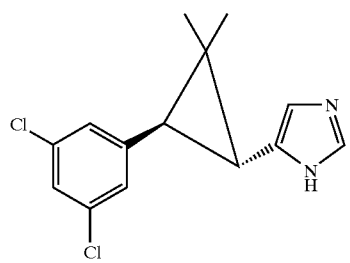

The chloromethyl ketone from Example 10 part D (50 mg) was taken in 5 ml formamide and heated at 160° C. for 4 h The solvent was evaporated and the residue was purified by preparative HPLC as described in Example 1 part H to give the title compound as a TFA salt, clear gummy solid; MS m/z 281 (M+H)⁺.

EXAMPLE 13

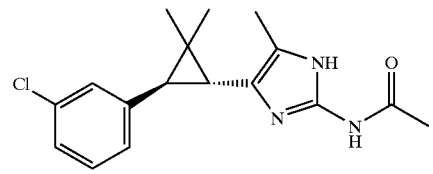

A.

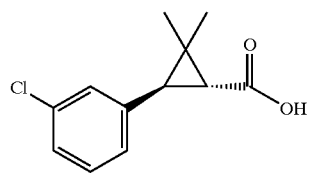

This compound was prepared from the corresponding cinnamic acid as described for Example 10 step B and C.

B.

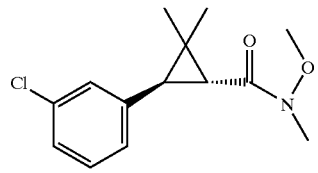

To a stirred solution of the acid from step A (7.0 g, 0.031 mol) in tetrahydrofuran (50 mL) was added CDI (6.1 g, 0.037 mol). After the reaction mixture were stirred at room temperature for 1 hr, N,O-dimethyl hydroxylamine (HCl salt) (3.66 g, 0.037 mol), triethylamine (13 mL, 0.093 mol) and N,N-dimethyl aminopyridine (100 mg) were added to the reaction mixture, then the reaction mixture was stirred for an additional 18 hrs and the solvent was removed. The residue was dissolved in ethyl acetate (150 mL) and washed with 0.5 N sodium hydroxide (2×200 mL) and 1 N hydrochloride acid (2×200 mL). The organic layer was dried over anhydrous magnesium sulfate. After removal of magnesium sulfate by filtration, the filtrate was concentrated to give 6 g (80%) title compound as a clear oil; $^1$H NMR δ (CDCl$_3$) 7.26 (s, 1H), 7.20 (m, 2H), 7.16 (s, 1H), 3.75 (s, 3H), 3.26 (s, 3H), 2.76 (d, J=6 Hz, 1H), 2.40 (s, 1H), 1.30 (s, 3H), 0.96 (s, 3H).

C.

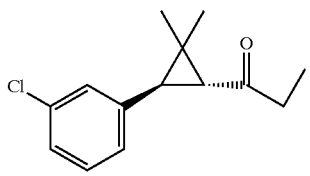

To a stirred solution of the compound from step B (6.0 g, 0.022 mol) in tetrahydrofuran (100 mL) at −20° C. under nitrogen was added 3M ethyl magnesium bromide in ether (19 mL). Then the reaction mixture were warmed to room temperature and stirred for additional 2 hrs. Saturated ammonium chloride in water (50 mL) was added and the reaction mixture was diluted with ethyl acetate (200 mL). The organic layer was collected and washed with brine and dried over anhydrous magnesium sulfate. After removal of magnesium sulfate by filtration, the filtrate was concentrated and the crude product was purified by silica gel chromatography using 70% dichloromethane in hexane as the eluent to give 5.21 g (98.3%) title compound as a clear oil; $^1$H NMR δ (CDCl$_3$) 7.26 (s, 1H), 7.20 (m, 2H), 7.16 (s, 1H), 2.83 (d, J=5.9 Hz, 1H), 2.63 (m, 2H), 2.25 (d, J=5.9 Hz, 1H), 1.31 (s, 3H), 1.14 (m, 3H), 0.95 (s, 3H).

D.

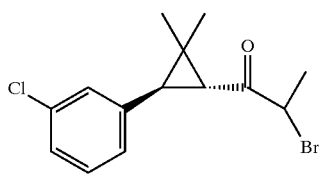

To a stirred solution of compound from step C (3.0 g, 0.013 mol) in tetrahydrofuran (50 mL) at −70° C. under nitrogen was slowly added 1.0 M LiHMDS in tetrahydrofuran (12.7 mL, 0.013 mol). Then the reaction mixture was slowly warmed to 5° C. A solution of N-bromosuccinimide (20 g, 0.013 mol) in dry tetrahydrofuran (10 mL) was slowly added to the reaction mixture at −70° C. under the nitrogen and the reaction mixture was stirred for 2 hrs. Then the reaction mixture was poured into ethyl acetate (100 mL) and 1 N hydrochloride acid (100 mL). The organic layer was washed with 1 N hydrochloride acid (100 mL), dried over anhydrous magnesium sulfate, concentrated and the crude product was purified by silica gel chromatography using 10% dichloromethane/hexane as the eluent to give 2.0 g (50%) title compound as a light green oil; $^1$H NMR δ (CDCl$_3$) 7.26 (s, 1H), 7.20 (m, 2H), 7.16 (s, 1H), 4.58 (m, 1H), 2.89 (d, J=6.0 Hz, 1H), 2.15 (s, 1H), 1.83 (m, 3H), 1.26 (s, 3H), 1.00 (s, 3H).

E.

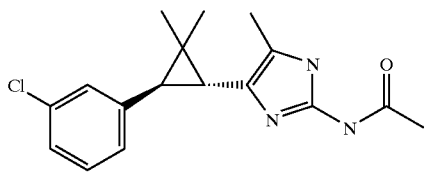

To a stirred solution of the compound from step D (1.8 g, 0.0057 mol) in DMF (14 mL) was added acetyl guanidine (1.8 g, 0.017 mol). The reaction mixture was stirred for 3 days, the solvent was removed under high vacuum and the crude product was purified by preparative HPLC (as described for the title compound of Example 1) to afford the title compound (1.10 g, 61%) as a light brown oil; $^1$H NMR δ (CDCl$_3$) 7.20–7.27 (m, 4H), 2.70 (broad peak), 2.32 (s, 3H), 2.28 (s, 3H), 2.01 (d, J=7.2 Hz, 1H), 1.13 (s, 3H), 0.99 (s, 3H).

EXAMPLE 14

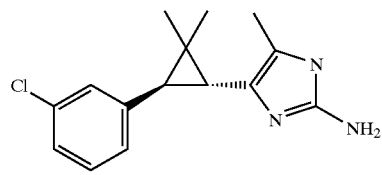

To a stirred solution of the title compound of Example 13 (50 mg, 0.15 mmol) in EtOH (10 mL) and water (5 mL) was added H$_2$SO$_4$(6 drops). The reaction mixture was refluxed for 36 hrs. The solvent was then evaporated and the crude product was purified by preparative HPLC (as described for the title compound of Example 1) to afford the title compound (10 mg, 23%) as an off-white powder (lyophilate); $^1$H NMR δ (CDCl$_3$) 7.20–7.27 (m, 4H), 2.31 (d, J=6.0 Hz, 1H), 2.18 (s, 3H), 1.89 (d, J=5.9 Hz, 1H), 1.11 (s, 3H), 0.93 (s, 3H).

EXAMPLE 15

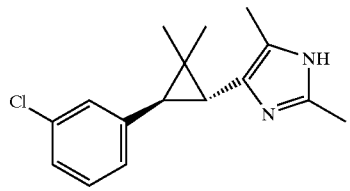

A mixture of the compound of Example 13 step D (100 mg, 0.32 mmol) and acetamidine free base (100 mg, 1.2 mmol) in methanol (2 mL) was stirred at room temperature for 18 hrs. The solvent was then evaporated and the crude product was purified by preparative HPLC (as described for the title compound of Example 1) to afford the title compound (23 mg, 25%) as a clear gum; $^1$H NMR δ (CDCl$_3$) 7.10–7.30 (m, 4H), 2.49 (s, 3H), 2.35 (d, J=1.89 (d, J=6.0 Hz, 1H), 2.22 (s, 3H), 1.97 (d, J=5.9 Hz, 1H), 1.05 (s, 3H), 0.94 (s, 3H).

EXAMPLE 16

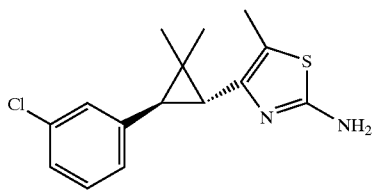

A mixture of the compound of Example 13 step D (180 mg, 0.57 mmol) and thiourea (180 mg, 2.4 mmol) in methanol (10 mL) was refluxed for 18 hrs. The solvent was then removed and the crude product was purified by preparative HPLC as described for the title compound of Example 1 to afford the title compound (192 mg) as white powder; $^1$H NMR δ (CDCl$_3$) 7.10–7.30 (m, 4H), 2.34 (d, J=6.0 Hz, 1H), 2.22 (s, 3H), 1.95(d, J=5.4 Hz, 1H), 1.14 (s, 3H), 0.99 (s, 3H).

EXAMPLE 17

A.

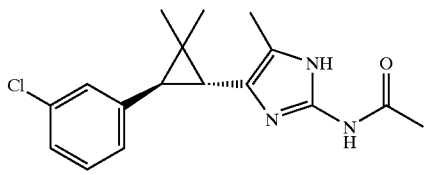

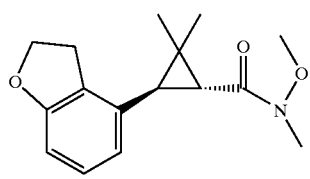

This compound was prepared from the corresponding acid by a procedure described for the synthesis of the step B compound of Example 13.

B.

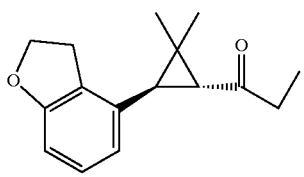

This compound was prepared from the Step A comound by a procedure described for the synthesis of the step C compound of Example 13.

C.

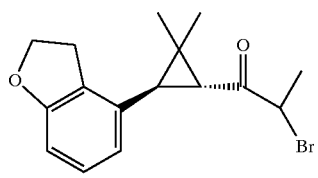

This compound was prepared from the Step B compound by a procedure described for the synthesis of the step D compound of Example 13.

D.

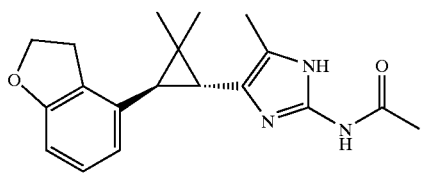

This compound was prepared from the Step C compound by a procedure described for the synthesis of the step E compound of Example 13; MS: m/z 326 (M+H)$^+$.

EXAMPLE 18

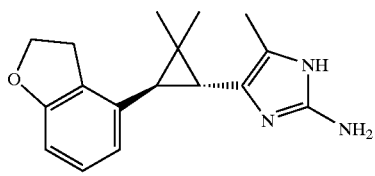

This compound was prepared from the part D compound of Example 17 by a procedure described for the synthesis of the title compound of Example 14; MS: m/z 284(M+H)$^+$.

EXAMPLE 19

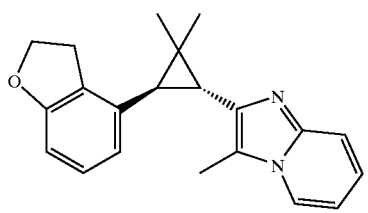

To a solution of the bromide from Example 17 part C (43 mg, 0.13 mmol) in DMF (1 mL) was added 2-aminopyridine (12.5 mg, 0.13 mmol). The mixture was heated at 90° C. for 1.5 h, after which the solvent was removed and the residue purified by preparative HPLC (as described for the title compound of Example 1) to afford the title compound as trifluoroacetic acid salt (19 mg, 34% yield): MS: m/z 319 (M+H)$^+$.

EXAMPLE 20

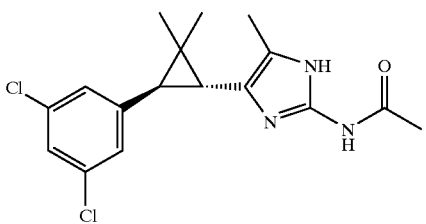

A.

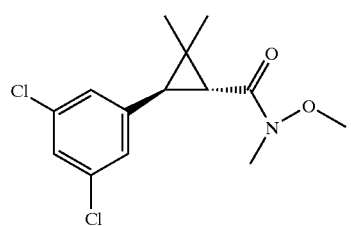

This compound was prepared by a procedure described for the synthesis of the step B compound of Example 13.

B.

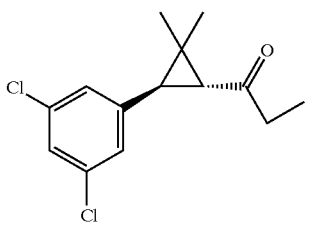

This compound was prepared by a procedure described for the synthesis of the step C compound of Example 13.

C.

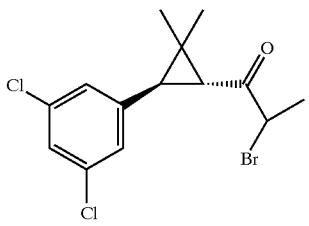

This compound was prepared by a procedure described for the synthesis of the step D compound of Example 13.

D.

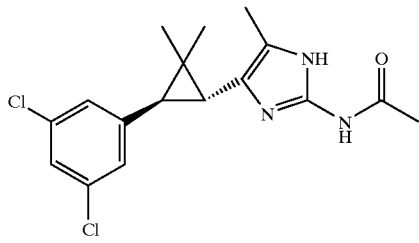

This compound was prepared from the above step C compound according to the procedure described for the synthesis of the title compound of Example 13 part E; MS m/z 352 (M+H)$^+$.

EXAMPLE 21

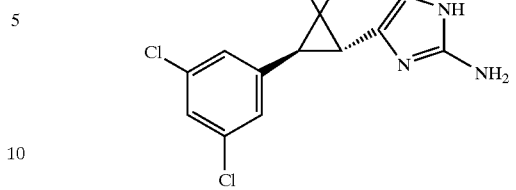

The title compound was prepared from the compound of Example 20 as described for the synthesis of the compound of Example 14; MS: m/z 310 (M+H)$^+$.

EXAMPLE 22

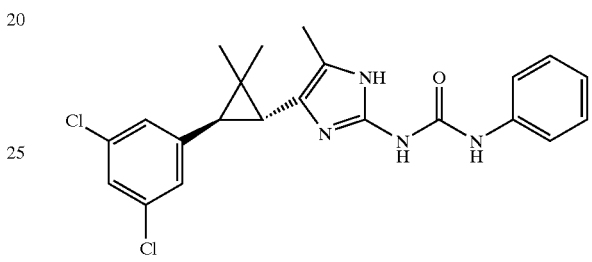

To a solution of the compound of Example 21 (8 mg, 0.026 mmol) in DMF (1 mL) was added phenyl isocyanate (4.1 µL, 0.052 mmol) and N,N-diisopropylethylamine (DIEA) (6.6 µL, 0.052 mmol). The reaction mixture was stirred for 18 hrs. A solution of 8.0 M ammonia in MeOH (1 ml) was added to the reaction mixture, the reaction mixture was stirred for 2 hr. The solvent was removed and the crude product was purified by preparative HPLC (as described for the title compound of Example 1) to afford the title compound (1.79 mg, 16%) as white powder (lyophilate); $^1$H NMR δ (CDCl$_3$): 12.70 (s, 1H), 8.63 (s, 1H), 7.10–7.48 (m, 8H) 2.94 (broad peak), 2.25 (s, 3H), 2.01 (d, J=5.9 Hz, 1H), 1.15 (s, 3H), 1.00 (s, 3H).

EXAMPLE 23

A.

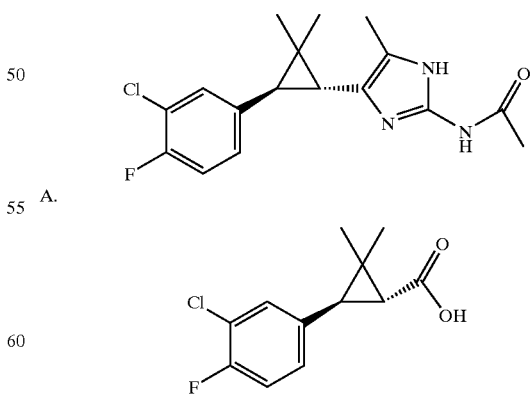

The title compound was prepared as described for the synthesis of the compound of Example 10, steps A, B, and C.

B.

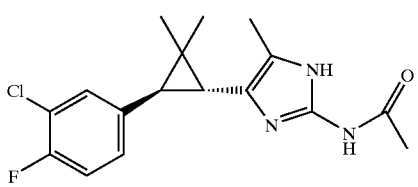

The title compound was prepared from the step A compound as described for the synthesis of Example 13, steps B. C, D and E; MS: m/z 336 (M+H)+.

EXAMPLE 24

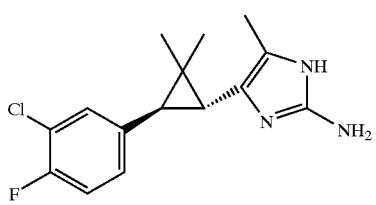

The title compound was prepared from the compound of Example 23 as described for the synthesis of the compound of Example 14; MS: m/z 294 (M+H)+.

EXAMPLE 25

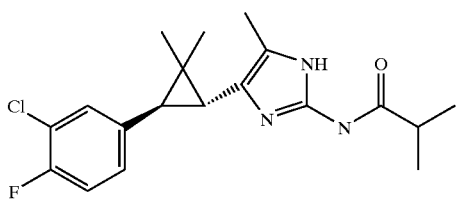

To a solution of the aminoimidazole from Example 24 (8 mg, 0.027 mmol) in dichloromethane (1 mL) was added isobutyryl chloride (28.7 mg, 0.27 mmol) followed by the addition of N,N-diisopropylethylamine (0.047 mL). The reaction mixture was stirred for 18 hrs. Then the solvent was removed and the crude product was purified by preparative HPLC as described for the title compound of Example 1 to afford the title compound. $^1$H NMR δ (CDCl$_3$) 13.80 (s, 1H), 7.35 (m, 2H), 7.11 (m, 1H), 3.90 (broad peak), 2.81 (m, 1H), 2.27 (s, 3H), 1.97 (d, J=5.8 Hz, 1H), 1.26 (s, 3H), 1.25 (s, 3H), 1.13 (s, 3H), 0.99 (s, 3H).

EXAMPLE 26

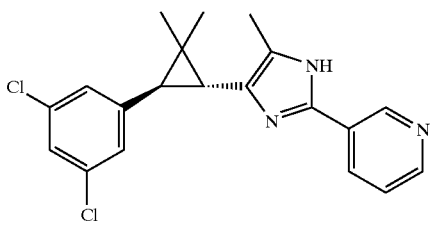

To the freshly prepared sodium methoxide (77 mg, 1.43 mmol) was added 3-amidineopyridine hydyochloride salt (250 mg, 1.59 mmol). The reaction mixture was stirred for 30 mins. Then to this reaction mixture was added the bromide from step C Example 20 (90 mg, 0.25 mmol) in MeOH (1 mL) and the reaction mixture was tirred for 18 hrs. The solvent was removed and the crude product was purified by preparative HPLC (as described for the title compound of Example 1) to afford the product (60.26 mg, 65%) as off-white powder. $^1$H NMR δ (CDCl$_3$) 9.70 (s, 1H), 9.15 (s, 1H), 7.05–7.35 (m, 7H), 2.48 (d, J=5.9 Hz, 1H), 2.37 (s, 3H), 2.11 (d, J=5.9 Hz, 1H), 1.10 (s, 3H), 1.01 (s, 3H).

EXAMPLE 27

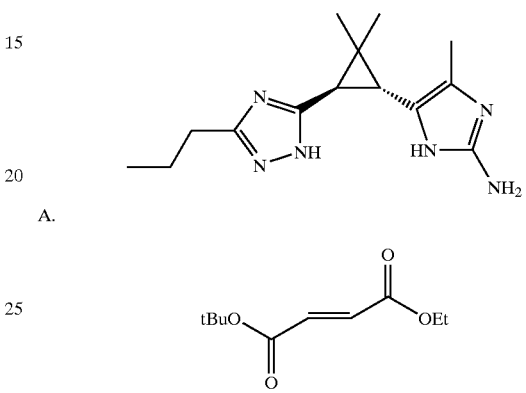

A.

To a stirred solution of fumaric acid mono ethyl ester (30 g, 208 mmol) and di-tert-butyl dicarbonate (57.7 g, 260 mmol) in THF (300 mL) was added 4-dimethylaminopyridine (5.1 g, 41.7 mmol) in small portions at 0° C. The reaction mixture was stirred at ambient temperature for 14 hours, diluted with ethyl acetate and washed sequentially with 10% aqueous sulfuric aic, 10% aqueous NaOH and brine. The organic layer was dried over magnesium sulfate and concentrated to afford the title compound as a brown oil (33 g, 79% yield).

B.

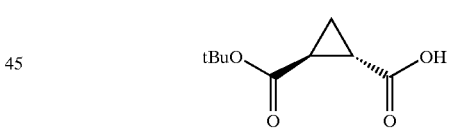

To a stirred suspension of isopropyltriphenyl phosphonium iodide (78.5 g, 181.5 mmol) in 300 mL THF was added n-BuLi (2.5 M in hexanes, 79.2 mL, 198 mmol) at −78° C. under nitrogen. The reaction mixture was briefly allowed to come to −5° C. The resulting clear red solution was cooled to −78° C. followed by the addition of a solution of the compound from part A (33 g, 165 mmol) in 100 mL THF. The mixture was allowed to come to room temperature and stirred for 14 hours. The reaction mixture was worked up as usual with ethyl acetate and saturated sodium bicarbonate to afford a crude gummy residue. This material was dissolved in 300 mL THF, added a solution of LiOH monohydrate (7.92 g, 198 mmol) in 300 mL water and stirred at RT for 14 hours. The mixture was diluted with water, washed with ether, the aqueous layer acidified with 10% NaHSO$_4$ and extracted with ethyl acetate. The ethyl acetate extract was dried over magnesium sulfate and concentrated to afford the title compound as a brown oil (19.9 g, 56% yield).

C.

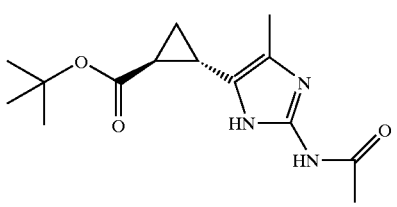

The acid from step B was converted to the title compound via the corresponding ethyl ketone and α-bromoketone by the procedure described for Example 13, steps B, C, D, and E.

D.

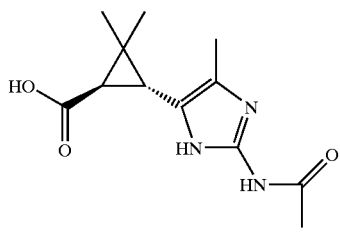

The compound from step C (200 mg) was dissolved in 1.5 mL methylene chloride, added 1.5 mL trifluoroacetic acid and the resulting solution was kept at RT for 12 hours. The mixture was concentrated to afford the title compound (238 mg, 100% yield, TFA salt) as a white solid; MS: m/z 252 (M+H)$^+$.

E.

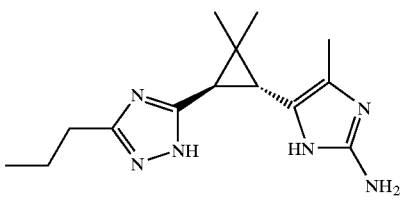

To a stirred solution of the compound from step D (20 mg, 0.06 mmol) and ethyl butanimidate hydrochloride

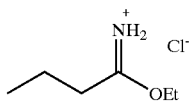

(14.5 mg, 0.096 mmol) in 0.5 mL DMF was sequentially added PyBOB (62 mg, 0.12 mmol) and triethylamine (0.033 mL, 0.24 mmol). The mixture was stirred at RT for 14 h, added 0.2 mL hydrazine and stirred at RT for 12 hours. The mixture was worked up as usual with ethyl acetate and saturated sodium bicarbonate to afford a crude gummy residue. This material was dissolved in 1 mL MeOH, added 0.5 mL water and 3 drops conc. sulfuric acid and the mixture was heated at 120° C. for 48 hours. The reaction mixture was subjected to preparative HPLC (C18 column/water-MeOH-TFA 90:10:0.1 to 10:90:0.1 gradient to afford the title compound as a pale gum (7 mg, TFA salt); MS: m/z 275 (M+H)$^+$.

EXAMPLE 28

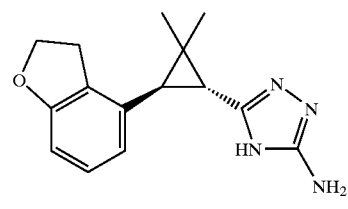

1,1'-Carbonyldiimidazole (0.314 g) was added to a solution of

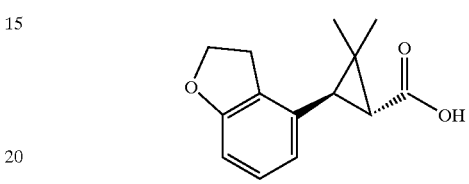

(0.3 g, prepared as described in WO 9933460) in 5 mL DMF. The mixture was stirred at RT for 1 h followed by the addition of aminoguanidine bicarbonate (0.53 g). Stirring was continued at RT for 14 hours and the mixture was diluted with ethyl acetate, washed with water, dried over magnesium sulfate and concentrated to give crude yellow gum. This material was triturated from ether to give white hygroscopic solid (105 mg).

EXAMPLE 29

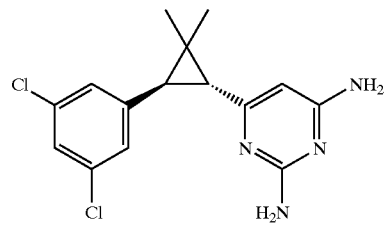

Acetonitrile (0.313 mL, 6 mmol) was added at −78° C. to a stirred solution of lithium bistrimethylsilylamide (6 mL, 1M in THF) in 35 mL THF under argon. The mixture was stirred at −78° C. for 1 h, followed by the addition of a solution of the amide from part A Example 20 in 10 mL THF. The mixture was allowed to come to RT over 1 h, diulted with EtOAc, washed with sat. sodium bicarbonate solution, dried over magnesium sulfate and concentrated to afford 1.3 g crude cyanomethyl ketone as pale oil. A portion of this material (1 g) was dissolved in 20 mL THF, sequentially treated with ethyldiisopropylamine (3 mL) and a freshly generated solution of diazomethane in 100 mL ether (used excess). The mixture was allowed to stand at RT for 14 h, added acetic acid to quench excess diazomethane and concentrated to afford crude enol ether (1 g). A portion of this material was converted to the title compound as described below:

Potassium tert-butoxide (0.571 g, 5.1 mmol) was added to a suspension of guanidine hydrochloride (0.485 g, 5.1 mmol) in 25 mL EtOH and the mixture was refluxed for 1 h. The solvent was removed by distillation and the residue was heated at 150° C. for 1 h. The residue was concentrated from additional 25 ml EtOH and heated for 3 h at 150° and partitioned between water and EtOAc. The organic layer was dried over magnesium sulfate, concentrated and the residue purified by preparative HPLC (C18 column/water-MeOH-TFA 90:10:0.1 to 10:90:0.1 gradient to afford pale gum. Recrystallization from chloroform afforded a white solid (0.1 g); MS: m/z 323 (M+H)$^+$.

EXAMPLE 30

A.

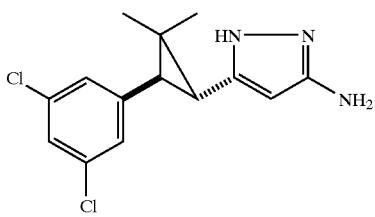

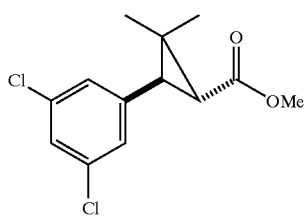

This compound was prepared in a manner similar to that described for the step A comopound of Example 7.

B.

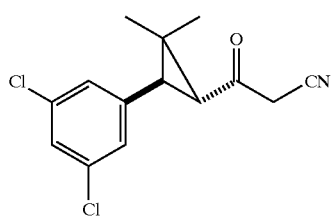

To a solution of 0.11 g (2.7 mmol) of acetonitrile in 20 mL of tetrahydrofuran was add 2.2 mL (3.3 mmol) of 1.5 M butyllithium at −78° C. The solution was stirred for 30 min at −78° C. and a solution of 0.3 g (1.1 mmol) of the part A compound in 10 mL of tetrahydrofuran. The resulting solution was stirred for 2 hr at −78° C. and 20 mL of saturated NH$_4$Cl was added warmed to ambient temperature and concentrated. The residue was then extrated with ethyl acetate. The organic layers were dried and concentrated to give a yellow oil which was not further characterized and was used for the subsequent reaction.

C.

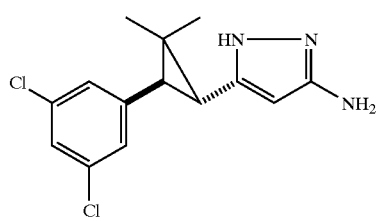

A solution of 0.31 g (1.1 mmol) of part B compound and 66 mg (1.3 mmol) of hydrazine monohydrate in 30 mL of ethanol was stirred of 6 h at 80° C. and cooled ambient temperature and concentrated (Z. Fomum, S. R. Landor, P. D. Landor, G. W. P. Mpango, J. Chem. Soc. Perkin Trans. 1, 1981 2997). The residue was purified using preparative HPLC as described for the title compound of Example 1 to afford 50 mg (16%) of the title compound, MS: m/z 296 (M+H)$^+$.

EXAMPLE 31

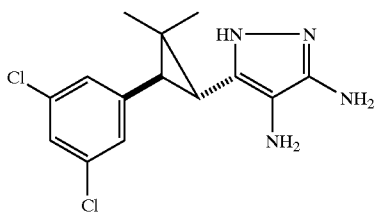

To a solution of 30 mg (0.10 mmol) of the pyrazole in 10 mL of methanol was added a solution of 2 M Na$_2$CO$_3$.

The mixture was cooled to 0° C. and 45 mg (0.20 mmol) of 4-methoxyphenyldiazonium tetrafluoroborate was added. The mixture was stirred for 2 h and concentrated. The residue was diluted with brine and extracted with ethyl acetate. The organic layer was dried and concentrated.

The residue was dissolved into 10 mL of methanol and 2 drops of concentrated HCl was added followed by 10 mg of PtO$_2$. The resulting mixture was hydrogenated at ambient pressure for 2 h and filtered. The filtrate was concentrated. The residue was purified using preparative HPLC as described for the title compound of Example 1 to give 10 mg (33%) of the title compound, MS: m/z 311 (M+H)$^+$.

EXAMPLE 32

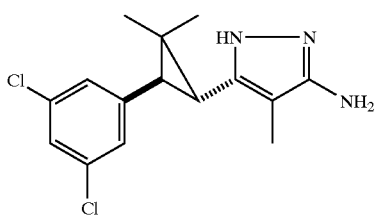

To a solution of 85 mg (1.8 mmol) of propionitrile in 10 mL of tetrahydrofuran was add 1.2 mL (1.8 mmol) of 1.5 M butyllithium at −78° C. The solution was stirred for 30 min at −78° C. and a solution of 0.173 g (0.62 mmol) of Methyl 2-(3,5-dichlorophenyl)-3,3-dimethyl-carboxylate in 5 mL of tetrahydrofuran. The resulting solution was stirred for 2 hr at −78° C. and 20 mL of saturated NH$_4$Cl was added warmed to ambient temperature and concentrated. The residue was then extracted with ethyl acetate. The organic layers were dried and concentrated to give a yellow oil. The yellow oil was then dissolved in 20 mL of ethanol and 37 mg (0.75 mmol) of hydrazine monohydrate was added. The solution was stirred for 18 h at reflux cooled to ambient temperature and concentrated. The residue was purified using preparative HPLC as described for the title compound of Example 1 to give 20 mg (18%) of the product, MS: m/z 310 (M+H)$^+$.

EXAMPLE 33

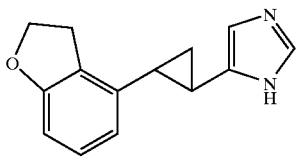

A.

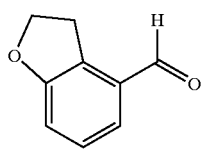

Ozone was bubbled into a stirring cold solution of

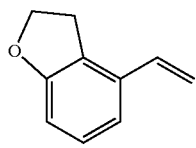

(3 g, 21 mmol, prepared as described in WO 9933460) in dichloromethane (50 mL). The reaction was monitored by TLC (20:1 hexane/ethyl acetate). Upon completion of the reaction the mixture was purged with nitrogen for a few minutes followed by the addition of Hunig's base (N,N-ethyldiisopropylamine, 5.44 g, 42 mmol). Stirring was continued while the reaction warmed to RT. The reaction was washed with 0.5 N HCl, water, and then brine. The organic layer was dried over MgSO$_4$; filtered and concentrated in vacuo. The title compound (oil, 2.10 g, 69% yield) was isolated via silica gel using 10% ethyl acetate in hexanes.

B.

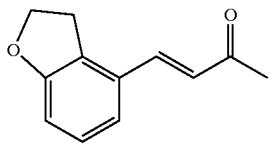

To a solution of the aldehyde A (1.0 g, 6.75 mmol) in dichloromethane (40 mL) was added triphenylphosphoranylidene-2-propanone (3.2 g, 10.12 mmol). The reaction was refluxed for 16 hrs and the solvent was removed in vacuo. The title compound (white solid, 1.86 g, 99% yield) was purified via silica gel chromatography using 5% ethyl acetate in hexanes as the eluent.

C.

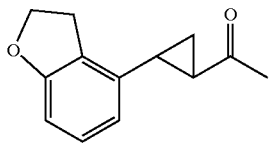

The cyclopropanation of the ketone from step B was done (3.76 g, 20 mmol) in tetrahydrofuran (20 mL) at 0° C. was done by adding an excess of a cold solution of diazomethane in ether followed by Pd(OAc)$_2$. The reaction was monitored by $^1$H NMR. After completion, the excess diazomethane was decomposed by the addition of acetic acid. The reaction was filtered through a Celite pad and the solvent was removed in vacuo. The trans-title compound (heavy oil, 3 g, 74% yield) was isolated via silica gel chromatography using 20% ethyl acetate in hexanes.

D.

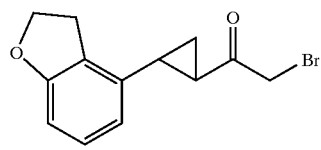

A solution of the cyclopropanated ketone C (540 mg, 2.67 mmol) and triethylamine (1.12 mL, 8.01 mmol) in dichloromethane (20 mL) was stirred under nitrogen at RT. To this solution, tert-butyldimethylsilyltrifluoromethane sulfonate (0.92 mL, 4.01 mmol) was added dropwise. The reaction was monitored by TLC. After completion, the reaction was diluted with dichloromethane and washed with a 1:1 solution of water and saturated NaHCO$_3$. The organic layer was dried over MgSO$_4$ and concentrated to afford the silyl enol ether as a heavy oil. The silyl enol ether was taken in dichloromethane (20 mL) and solid NBS (475 mg, 2.67 mmol) was added. The reaction was monitored by TLC. The title compound (heavy oil, 370 mg, 49% yield) was isolated via silica gel chromatography using 49% ethyl acetate in hexanes.

E.

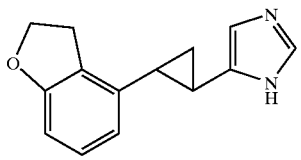

The title compound was prepared from step D compound as described for Example 12. The product was isolated as TFA salt (heavy yellow oil, 9.9% yield), MS: m/z 323 (M+H)$^+$.

EXAMPLE 34

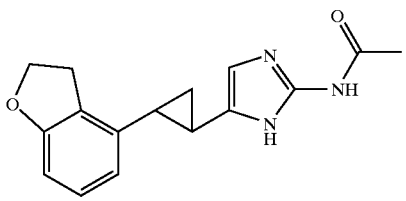

The title compound was prepared from Example 33, step D compound as described in Example 13 step E. The product was isolated as TFA salt, (light yellow solid, 43% yield), MS: m/z 284 (M+H)$^+$.

EXAMPLE 35

A.

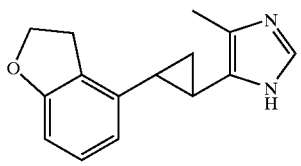

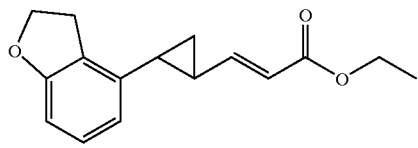

To a stirring solution of the aldehyde from step A Example 33 (400 mg, 2.7 mmol) in dichloromethane (40 mL) was added carbethoxymethylene-triphenylphosphorane (1.41 g, 4.05 mmol). The reaction was refluxed for 16 hrs. and the solvent was removed in vacuo. The title compound (white solid, 533 mg, 91% yield) was isolated from a silica gel column using 20% ethyl acetate in hexanes as the eluent.

B.

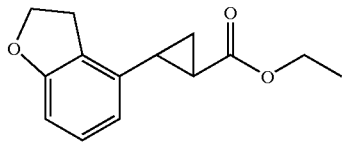

The title compound was prepared from step A compound as described for the step C compound, Example 33.

C.

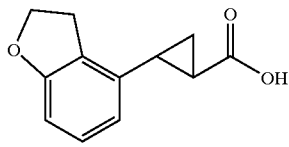

A solution of the ester from step B in a 1:1 mixture of dioxane (10 mL) and 10% KOH (10 mL) was heated at 50° C. for 1 hr. The reaction was acidified with 1N HCl to pH 2 and was extracted with ethyl acetate thrice. The organics were combined, dried over MgSO$_4$, filtered and concentrated in vacuo affording the carboxylic acid as an amorphous solid (410 mg, 93% yield).

D.

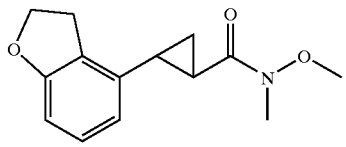

A solution of the carboxylic acid from step C (800 mg, 3.91 mmol) and CDI (1.27 g, 7.82 mmol) in tetrahydrofuran (20 mL) was stirred for 30 min at RT.

Triethylamine (2.2 mL, 15.64 mmol) was added followed by O,N-dimethylhydroxylamine HCl (763 mg, 7.82 mmol) and DMAP. The reaction was stirred at RT for 16 hrs. The reaction was diluted with a 1:1 mixture of diethyl ether and dichloromethane and washed with brine. The organic layer was dried over MgSO4, concentrated and the crude product was purified by silica gel chromatography using 50% ethyl acetate in hexanes; MS: m/z 248 (M+H)$^+$.

E.

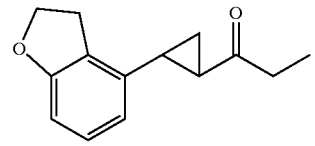

The title ketone (oil, 95% yield) was prepared according to methodology used for the preparation of step C compound, Example 13, MS: m/z 217 (M+H)$^+$.

F.

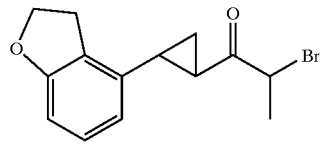

The title alpha-bromo ketone (oil, 85% yield) was prepared from the step E compound by using the procedure of the step D compound, Example 13.

G.

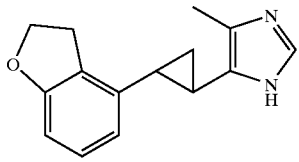

The title compound (TFA salt, yellow oil, 37% yield) was prepared from the step F compound using the procedure described for the synthesis of the compound of Example 12; MS: m/z 241 (M+H)$^+$.

EXAMPLE 36

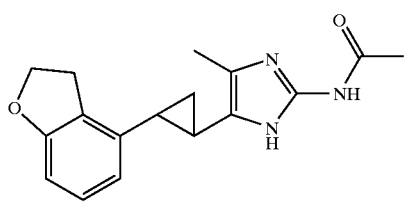

The title compound was prepared from Example 35, step F compound as described in Example 13 step E; TFA salt, tan solid, 10% yield; MS: m/z 298 (M+H)$^+$.

EXAMPLE 37

The title compound (TFA salt, yellow oil, 42% yield) was prepared in a manner similar to that described for the synthesis of the title compound of Example 33; MS: m/z 185 (M+H)$^+$.

EXAMPLE 38

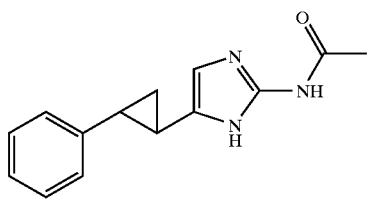

The title compound (TFA salt, yellow solid, 50% yield) was prepared in a manner similar to that described for the synthesis of the title compound of Example 34; MS: m/z 242 (M+H)$^+$.

EXAMPLE 39

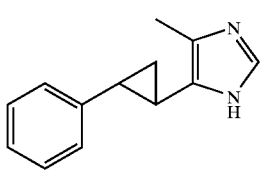

The title compound (TFA salt, yellow oil, 60% yield) was prepared via the corresponding ethyl ketone and alpha-bromoketone using the procedure described for the synthesis of the title compound of Example 35, MS: m/z 199 (M+H)$^+$.

EXAMPLE 40

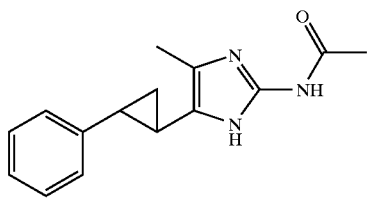

The title compound (TFA salt, tan solid, 12% yield) was prepared from the corresponding alpha-bromoketone using the procedure described in Example 13 step E; MS: m/z 256 (M+H)$^+$.

EXAMPLE 41

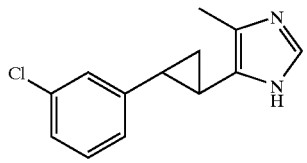

A.

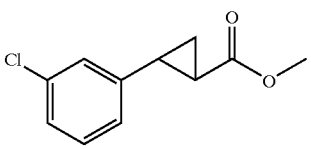

The title ester (oil, 82% yield) was prepared from 3-chlorocinnamic acid by the method described earlier for the synthesis of step C compound of Example 33.

B.

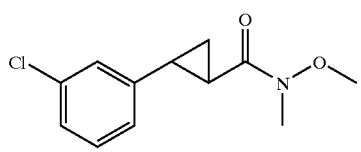

To a solution of O,N-dimethylhydroxylamine HCl (695 mg, 7.13 mmol) in dichloromethane (30 mL) at −78° C. was added a 2.0M solution of trimethylaluminum in toluene (6.42 mL). After stirring for 30 min. the mixture was warmed up to 0° C. A solution of the step A compound (1 g, 4.75 mmol) in dichloromethane (10 mL) was added to the reaction mixture. After 10 min at 0° C., the reaction was refluxed for 16 hrs. The reaction was worked up by adding 1M NaOH (40 mL) and the aluminum salts were filtered off. The aqueous layer was separated and extracted twice with dichloromethane. The combined organic layer was dried over MgSO$_4$, filtered and the solvent was removed in vacuo. The title compound (oil, 820 mg, 72% yield) was purified by silica gel chromatography using 50% ethyl acetate in hexanes.

C.

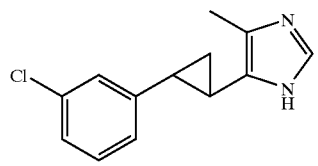

The title compound (TFA salt, yellow oil, 15% yield) was prepared via the corresponding ethyl ketone and alpha-bromoketone using the procedure described for Example 13 step C and D and Example 12, MS: m/z 233(M+H)$^+$.

EXAMPLE 41a

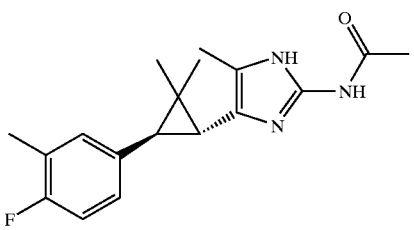

A.

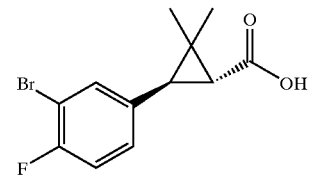

This compound was prepared from the corresponding benzaldehyde as described for Example 10 step A, B and C.

B.

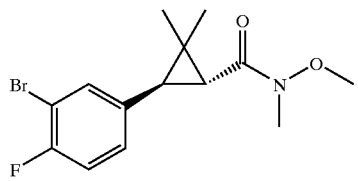

This compound was prepared from the step A compound as described for Example 13 step B; MS m/z 330 (M+H)+.

C.

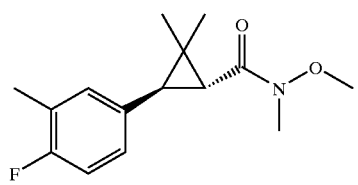

A suspension consisting of compound from step B (200 mg), tetramethyl tin (252 mg), tetrakis(triphenylphosphine) palladium (5 mg) and lithium chloride (50 mg) in DMF (3 ml) was heated to 90° C. for 18 hr. The solution was filtered, concentrated, and purified by preparative HPLC (as described for Example 1 part H) to give 147 mg as clear oil; MS m/z 266 (M+H).

D.

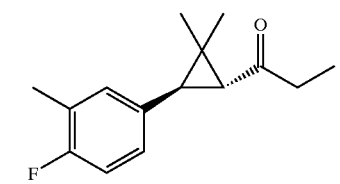

This compound was prepared from the step C compound as described for Example 13 step C.

E.

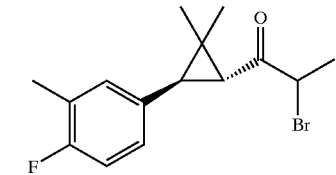

This compound was prepared from the step D compound as described for Example 13 step D.

F.

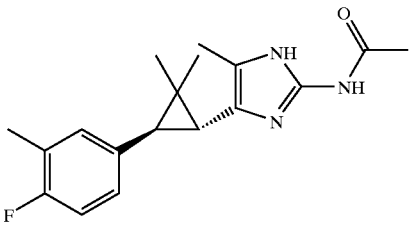

This compound was prepared from the step E compound as described for Example 13 step E. MS m/z 316 (M+H).

EXAMPLE 41 b

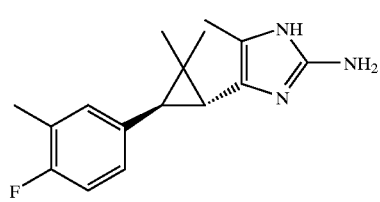

This compound was prepared from the title compound of Example 41a as described for Example 14; MS m/z 274 (M+H)+.

EXAMPLE 41c

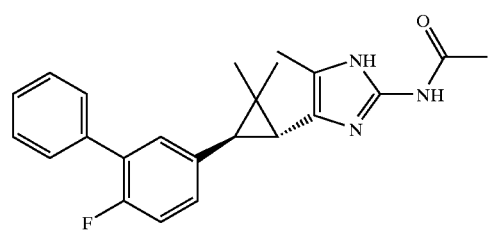

A.

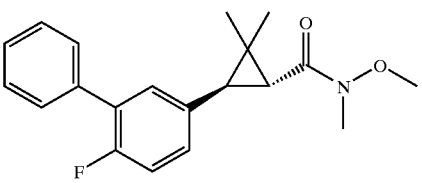

A suspension consisting of compound from Example 41a step B (200 mg), phenyl boronic acid (148 mg), tetrakis(triphenylphosphine)palladium (5 mg) and 2.0M Na$_2$CO$_3$ (0.76 ml) in DMF (3 ml) was heated to 90° C. for 18 hr. The solution was filtered, concentrated, and purified by preparative HPLC (as described for example 1 part H) to give 152 mg as clear oil; MS m/z 328 (M+H)+.

B.

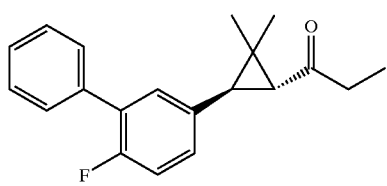

This compound was prepared from step A as described for Example 13 step C.

C.

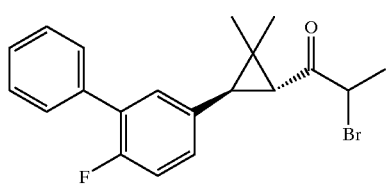

This compound was prepared from step B as described for Example 13 step D.

D.

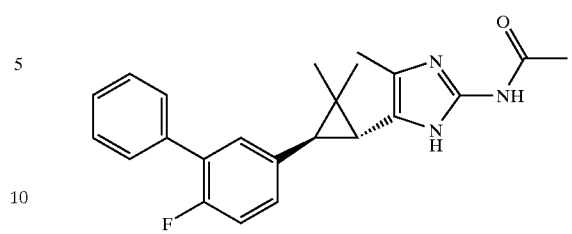

This compound was prepared from step C as described for Example 13 step E; MS m/z 378 (M+H)$^+$.

EXAMPLE 41d

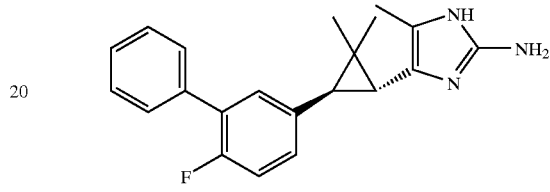

This compound was prepared from Example 41c as described for Example 14; MS m/z 336 (M+H)$^+$.

The following Examples were prepared according to the procedures described above for Examples 1 through Example 41d.

| Example # | Structure | Characterization MS: (M + H)$^+$ |
|---|---|---|
| 42 | 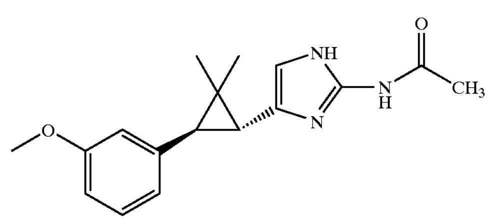 | 300 |
| 43 | 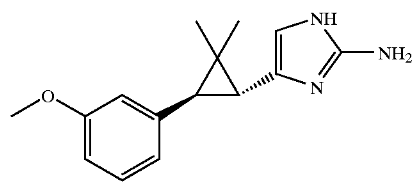 | 258 |
| 44 | 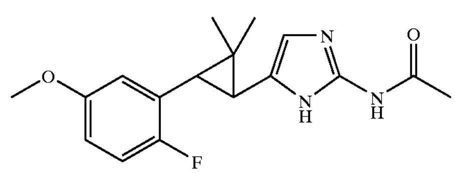 | 318 |
| 45 | 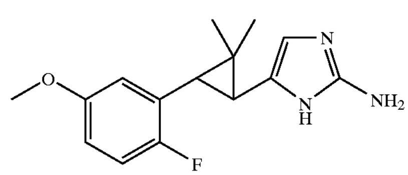 | 276 |

-continued
| Example # | Structure | Characterization MS: (M + H)+ |
|---|---|---|
| 46 | 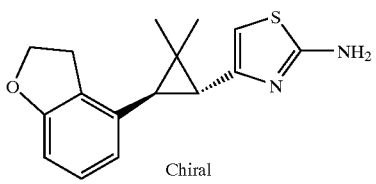 Chiral | 287 |
| 47 | 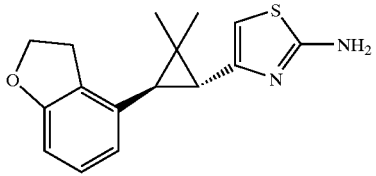 | 287 |
| 48 | 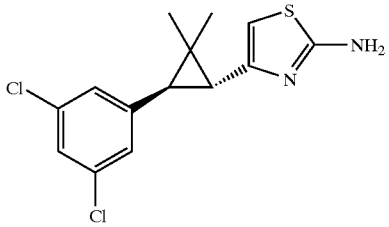 | 313 |
| 49 | 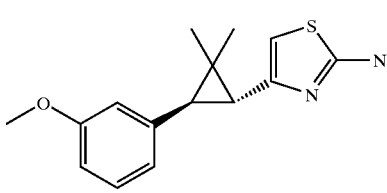 | 275 |
| 50 | 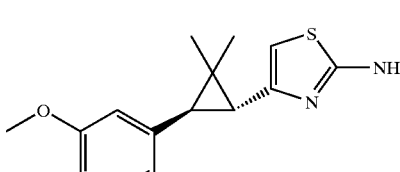 | 293 |
| 51 | 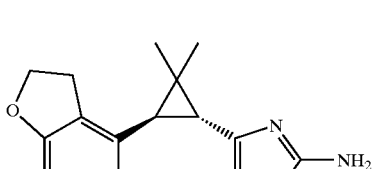 | 301 |
| 52 | 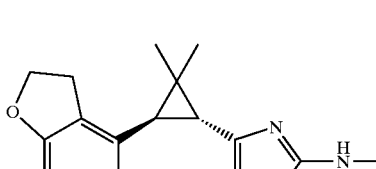 | 343 |

| Example # | Structure | Characterization MS: (M + H)+ |
|---|---|---|
| 53 | 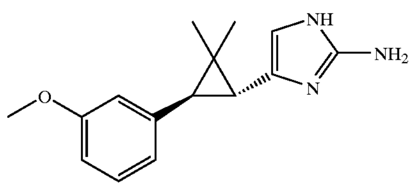 | 258 |
| 54 | Chiral | 301 |
| 55 | Chiral | 269 |
| 56 | 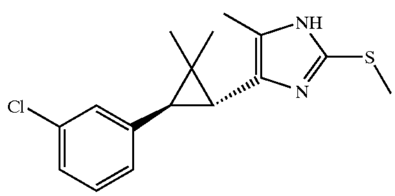 | 307 |
| 57 | 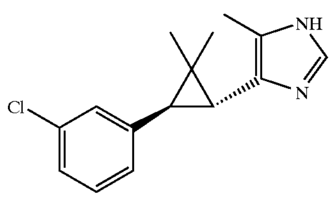 | 261 |
| 58 | 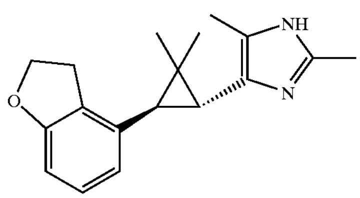 | 283 |
| 59 | 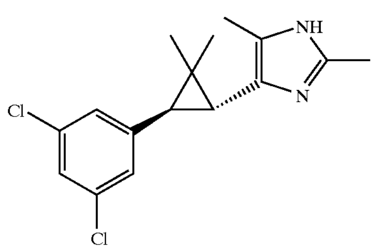 | 309 |

-continued
| Example # | Structure | Characterization MS: (M + H)+ |
|---|---|---|
| 60 | 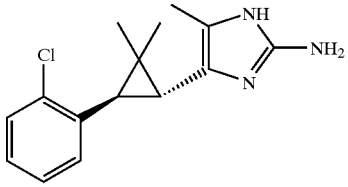 | 276 |
| 61 | 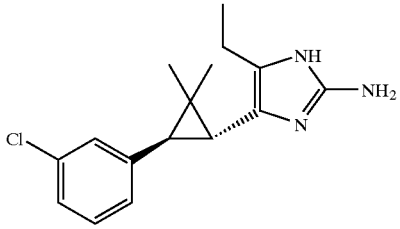 | 290 |
| 62 | 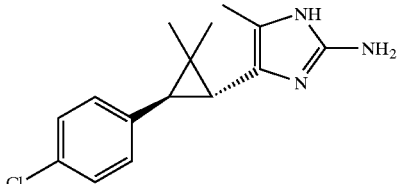 | 276 |
| 63 | 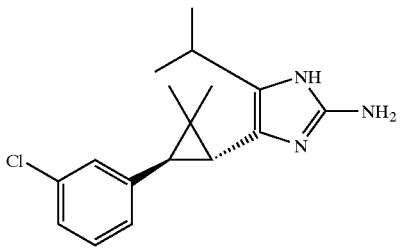 | 304 |
| 64 | 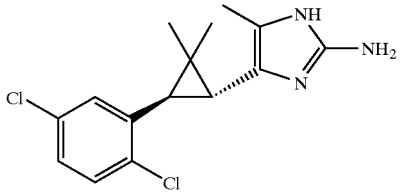 | 310 |
| 65 | 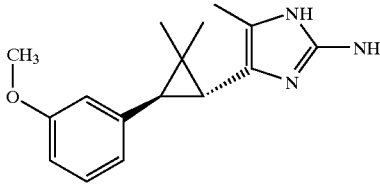 | 272 |
| 66 | 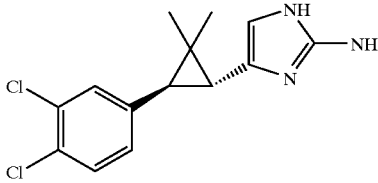 | 296 |

| Example # | Structure | Characterization MS: (M + H)+ |
|---|---|---|
| 67 | 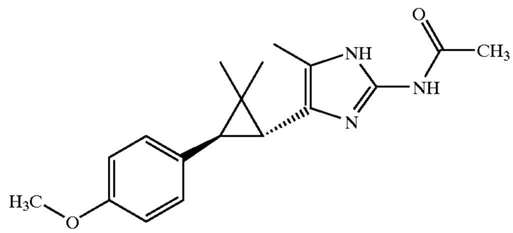 | 314 |
| 68 | 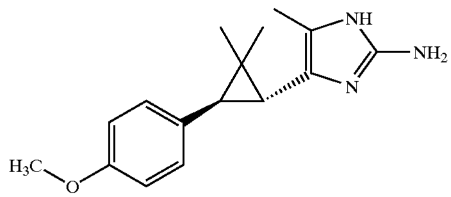 | 272 |
| 69 | 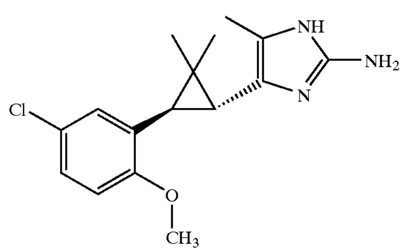 | 306 |
| 70 | 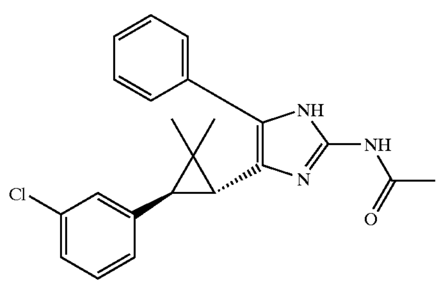 | 380 |
| 71 | 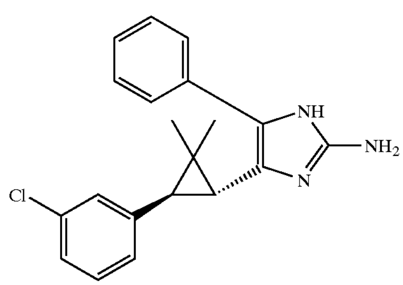 | 338 |
| 72 | 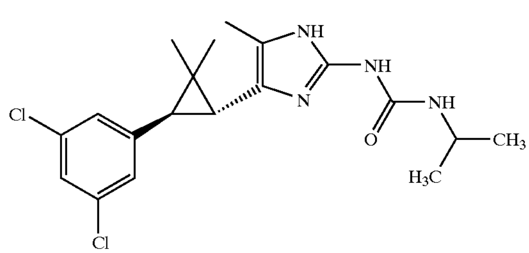 | 395 |

-continued

| Example # | Structure | Characterization MS: (M + H)+ |
|---|---|---|
| 73 | 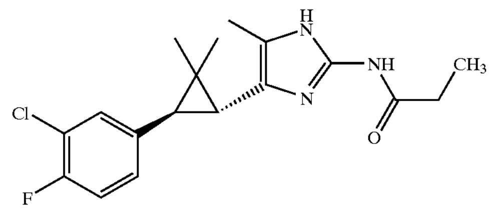 | 350 |
| 74 | 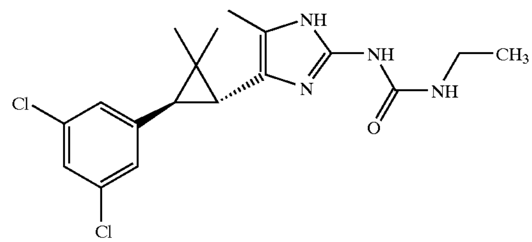 | 381 |
| 75 | 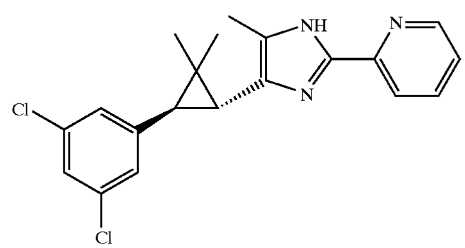 | 372 |
| 76 | 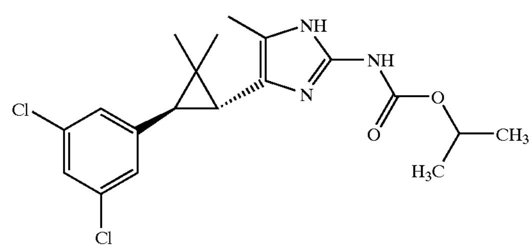 | 396 |
| 77 | 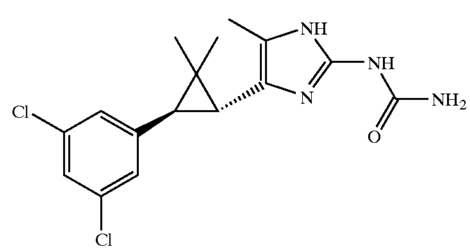 | 353 |
| 78 | 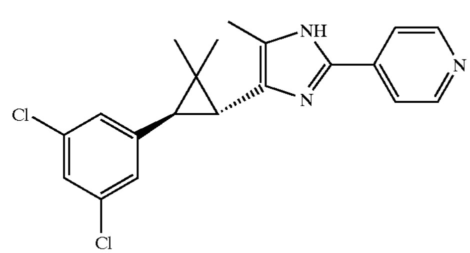 | 372 |

-continued

| Example # | Structure | Characterization MS: (M + H)+ |
|---|---|---|
| 79 | 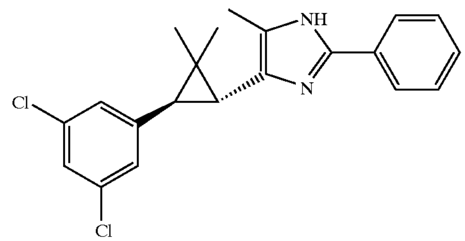 | 371 |
| 80 | 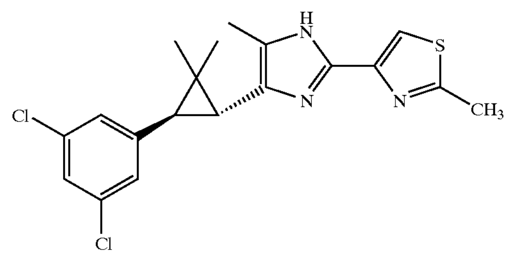 | 392 |
| 81 | 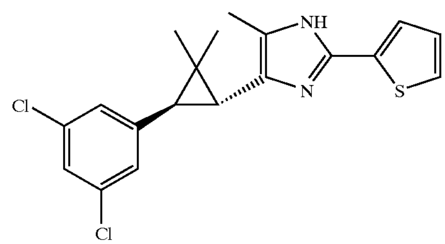 | 377 |
| 82 | 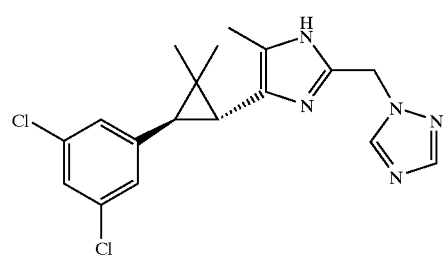 | 376 |
| 83 | 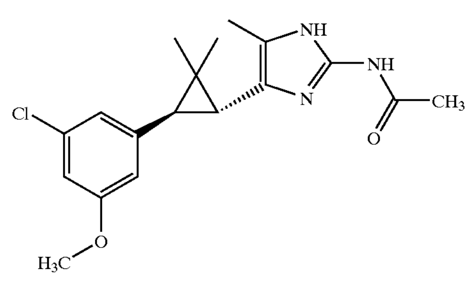 | 347 |
| 84 | 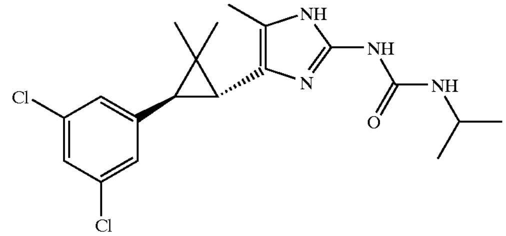 | 395 |

-continued
| Example # | Structure | Characterization MS: (M + H)+ |
|---|---|---|
| 85 | 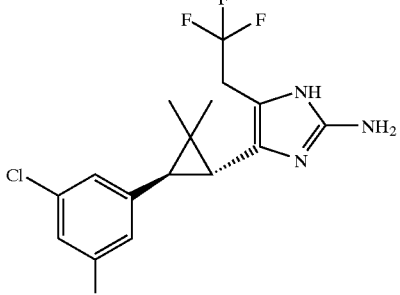 | 378 |
| 86 | 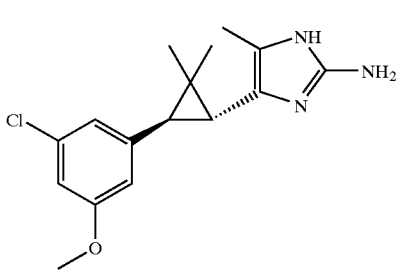 | 306 |
| 87 | 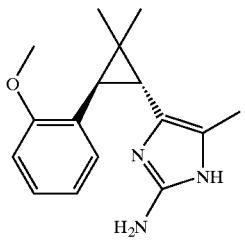 | 272 |
| 88 | 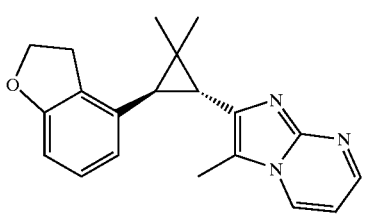 | 320 |
| 89 | 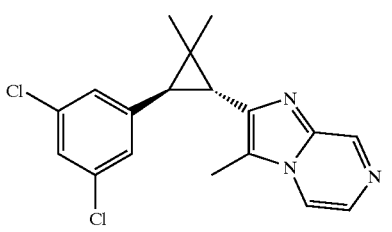 | 346 |
| 90 | 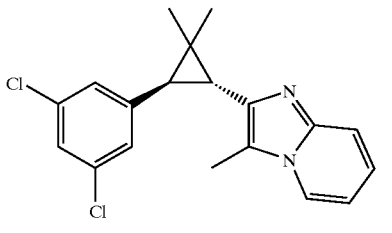 | 345 |

-continued

| Example # | Structure | Characterization MS: (M + H)+ |
|---|---|---|
| 91 | 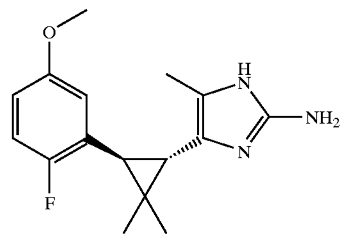 | 290 |
| 92 | 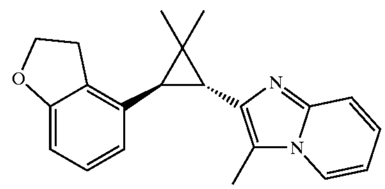 | 319 |
| 93 | 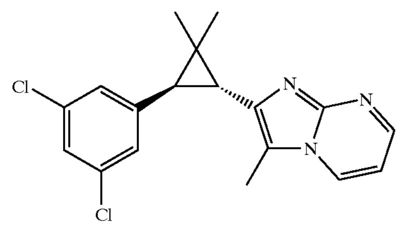 | 346 |
| 94 | 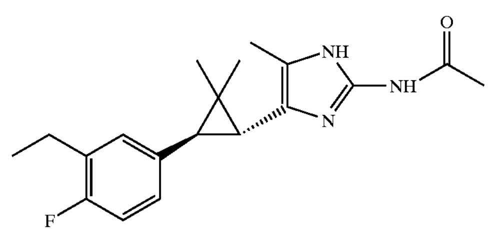 | 330 |
| 95 | 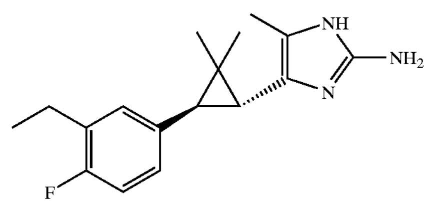 | 288 |
| 96 | 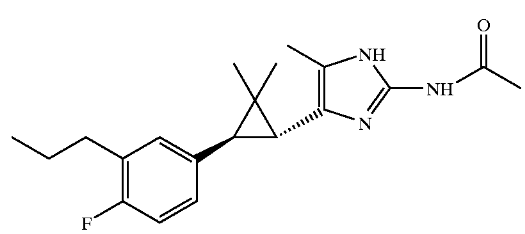 | 344 |
| 96a | 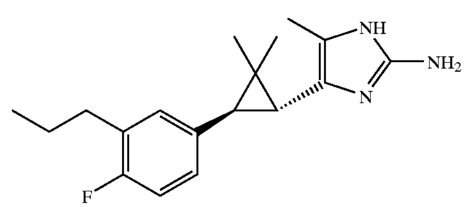 | 302 |

-continued

| Example # | Structure | Characterization MS: (M + H)+ |
|---|---|---|
| 96b | 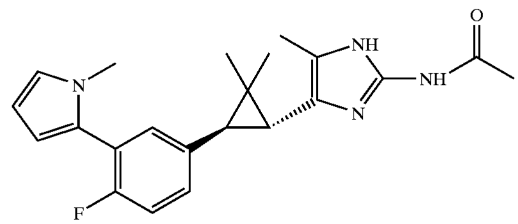 | 381 |
| 96c | 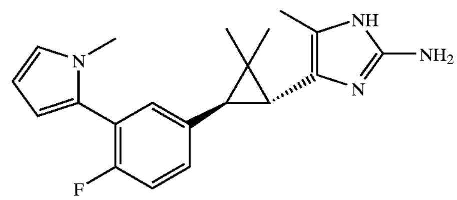 | 339 |
| 97 | 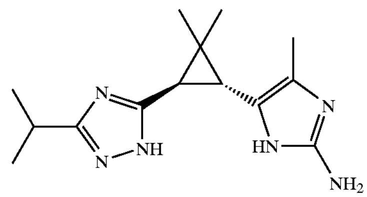 | 275 |
| 98 | 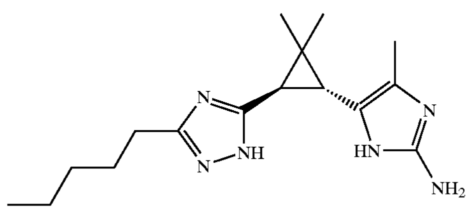 | 303 |
| 99 | 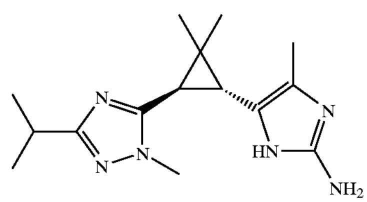 | 289 |
| 100 | 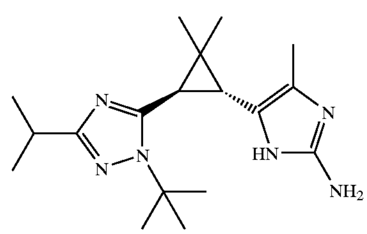 | 331 |
| 101 | 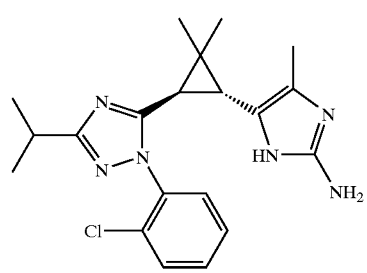 | 385 |

-continued
| Example # | Structure | Characterization MS: (M + H)+ |
|---|---|---|
| 102 | 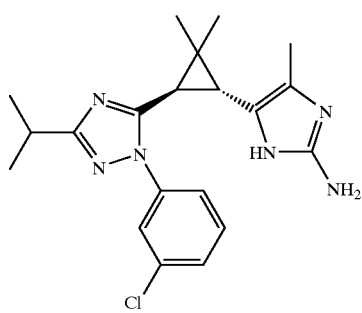 | 385 |
| 103 | 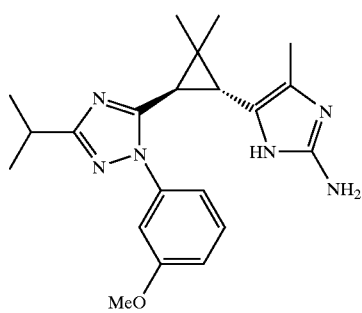 | 381 |
| 104 | 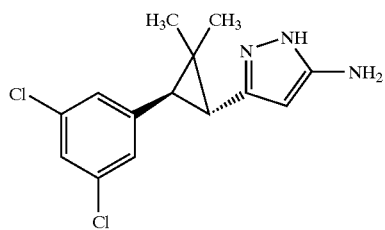 | 296 |
| 105 | 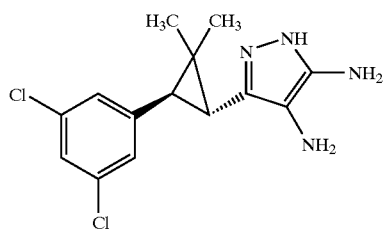 | 311 |
| 106 | 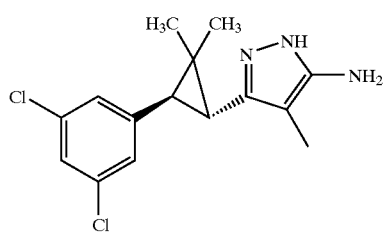 | 310 |

EXAMPLE 107

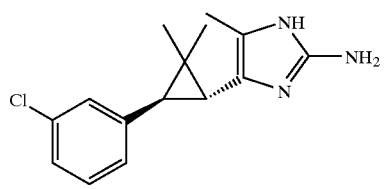

This compound was prepared in enantiomerically pure form by subjecting the corresponding racemic mixture from Example 14 to chromatography on a chiral column (CHIRACELL OD/hexane-isopropanol-triethylamine 90:10:0.1); MS: m/z 276 (M+H)$^+$.

EXAMPLE 108

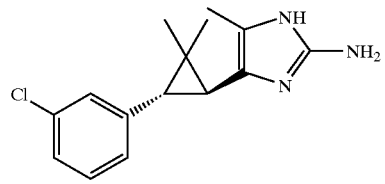

Chiral

This compound was prepared in enantiomerically pure form by subjecting the corresponding racemic mixture from Example 14 to chromatography on a chiral column (CHIRACELL OD/hexane-isopropanol-triethylamine 90:10:0.1); MS: m/z 276 (M+H)$^+$.

The following Examples 109 to 118 compounds were prepared by resolving the corresponding racemic mixtures as described for Examples 107 and 108 except that hexane-isopropanol-triethylamine 95:5:0.1 was used as the eluent.

| Example # | Structure | Characterization MS: m/z (M + H)$^+$ |
|---|---|---|
| 109 | 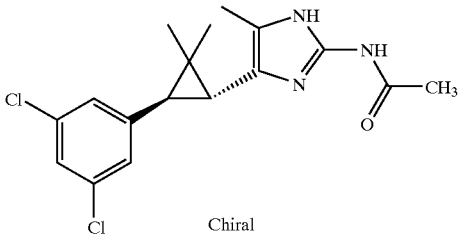 Chiral | 352 |
| 110 | 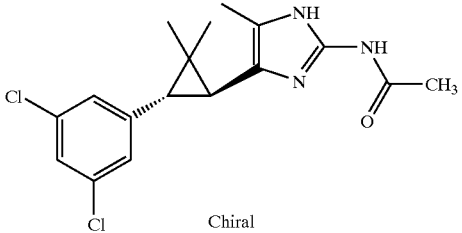 Chiral | 352 |
| 111 | 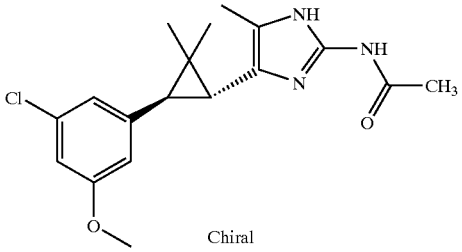 Chiral | 348 |
| 112 | 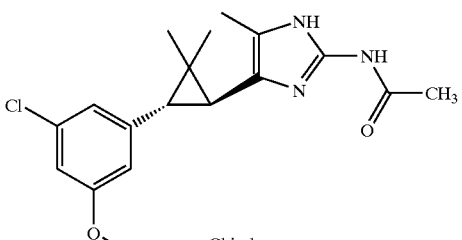 Chiral | 348 |

-continued

| Example # | Structure | Characterization MS: m/z (M + H)+ |
|---|---|---|
| 113 | (2-methoxy-5-chlorophenyl cyclopropyl methylimidazole acetamide), Chiral | 348 |
| 114 | (2-methoxy-5-chlorophenyl cyclopropyl methylimidazole acetamide), Chiral | 348 |
| 115 | (3-chloro-4-fluorophenyl cyclopropyl methylimidazole acetamide), Chiral | 336 |
| 116 | (3-chloro-4-fluorophenyl cyclopropyl methylimidazole acetamide), Chiral | 336 |
| 117 | (3-chloro-4-fluorophenyl cyclopropyl methylimidazole propanamide), Chiral | 350 |
| 118 | (3-chloro-4-fluorophenyl cyclopropyl methylimidazole propanamide), Chiral | 350 |

EXAMPLE 119

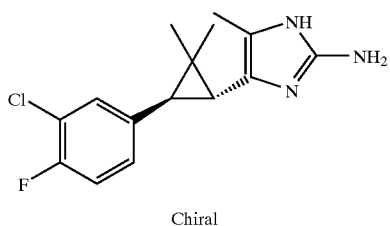

Chiral

The title compound was prepared from the compound of Example 115 as described for the synthesis of the compound of Example 14; MS: m/z 294 (M+H)⁺.

EXAMPLE 120

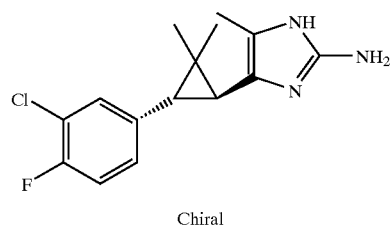

Chiral

The title compound was prepared from the compound of Example 116 as described for the synthesis of the compound of Example 14; MS: m/z 294 (M+H)⁺.

The following Examples 121 to 126 compounds were prepared according to the procedure described for the synthesis of the compounds of Example 119 and 120.

| Example # | Structure | Characterization MS: m/z (M + H)⁺ |
|---|---|---|
| 121 | 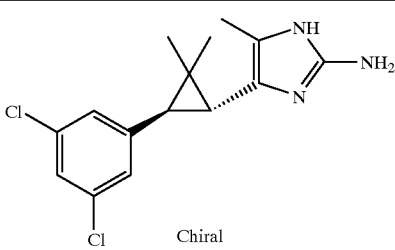 Chiral | 310 |
| 122 | 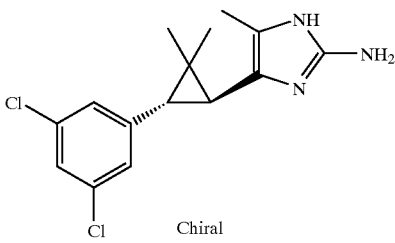 Chiral | 310 |
| 123 | 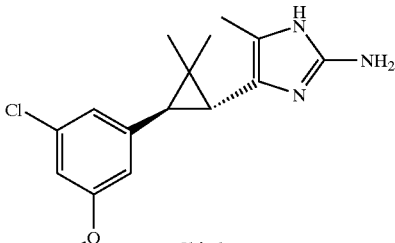 Chiral | 306 |
| 124 | 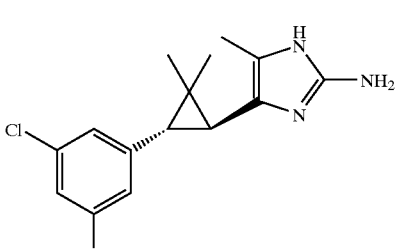 Chiral | 306 |

-continued

| Example # | Structure | Characterization MS: m/z (M + H)+ |
|---|---|---|
| 125 | 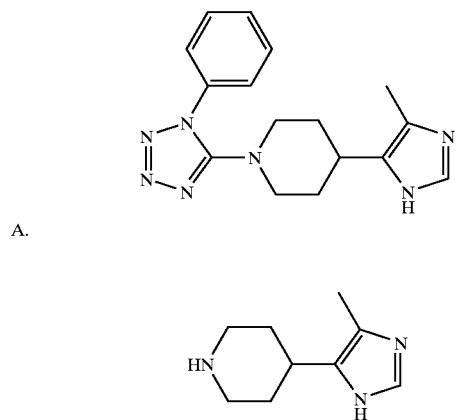 | 306 |
| 126 | 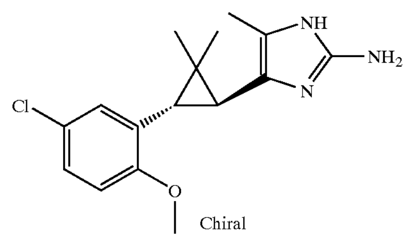 | 306 |

EXAMPLE 127

A.

B.

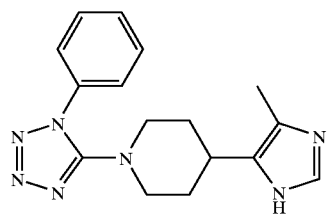

This compound was prepared as described by Jegham, Samir et al (EP0507650).

A mixture of 1-phenyl-2-chlorotetrazole (90.5 mg, 0.5 mmol), compound from part A (82.5 mg, 0.5 mmol) and 0.1 mL triethylamine in 1 mL N-methylpyrrolidinone was heated at 120° C. for 24 h, concentrated in vacuo and the residue subjected to preparative HPLC (C18 column/water-MeOH-TFA 90:10:0.1 to 10:90:0.1 gradient) to afford the title compound as a pale gum (62 mg); MS: m/z 310 $(M+H)^+$.

EXAMPLE 128

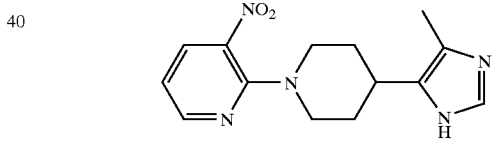

The mixture of the imidazole compound from Example 127 step A (6.00 g, 25.19 mmol), 2-chloro-3-nitropyridine (4.39 g, 27.71 mmol) and Hunig's base (11.7 g, 90.7 mmol) in DMF (45 mL) were heated at 85° C. for overnight. Upon completion, the reaction mixture was partitioned between dichloromethane and saturated sodium bicarbonate solution. The aqueous layer was washed with dichloromethane twice. The organic layers were combined, dried over magnesium sulfate and concentrated. The resulting brown residue was purified by silica gel chromatography (10%; methanol in ethyl acetate with 0.1% of TEA) to give 5.7 g (yield: 79%) of the title compound as a yellow solid; MS: m/z 288 $(M+H)^+$.

The following Examples 129 to 133 compounds were prepared by the methods described above.

| Example # | Structure | Characterization MS: (M + H)+ |
|---|---|---|
| 129 | 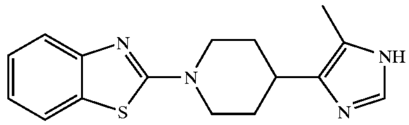 | 299 |
| 130 | 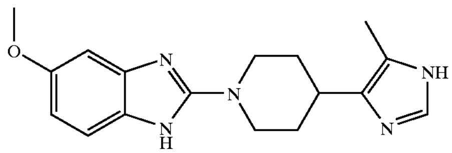 | 312 |
| 131 | 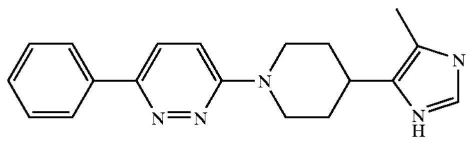 | 420 |
| 132 | 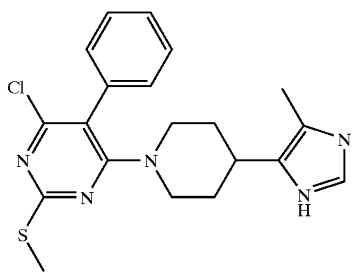 | 400 |
| 133 | 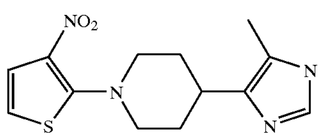 | 293 |

EXAMPLE 134

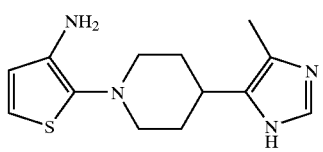

To a stirred solution of the compound of Example 133 (100 mg, 0.342 mmol) in EtOH/H$_2$O (1 mL:1 mL) was added ferrous sulfate. The reaction mixture was refluxed for 1 hr. Then aqueous ammonium hydroxide (0.8 mL) was added slowly and the reaction mixture was refluxed for additional 2 hours. The reaction mixture was extracted with ethyl acetate three times and the combined organic layers dried over magnesium sulfate. After the filtration, the solvent was evaporated to afford the title compound as a brown solid; MS: m/z 263 (M+H)+.

EXAMPLE 135

A.

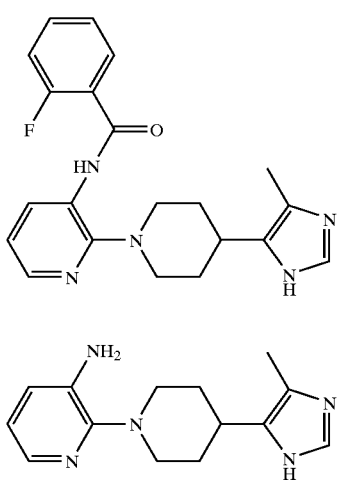

To the solution of the compound of Example 128 (100 mg, 0.348 mmol) in THF/MeOH (3 mL:3 mL) was added Pd/C. A balloon with hydrogen was placed on the reaction and the reaction mixture was stirred for 30 min. Then the reaction mixture was filtered and the solution was concentrated to afford (67 mg, 75% yield) the title compound as a brown powder.

B.

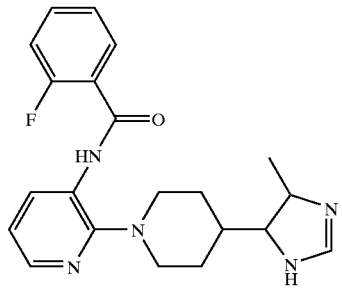

To a stirred solution of the step A compound (20 mg, 0.078 mmol) in THF (1 mL) was added triethylamine (39 mg, 0.39 mmol), followed by 2-fluorobenzoyl chloride (37 mg, 0.233 mmol) in THF (0.2 ml). The reaction mixture was stirred overnight. The solvent was concentrated and the crude was purified by preparative HPLC as in Example 1 to afford the title compound as the TFA salt; MS: m/z 380 (M+H)$^+$.

The following Examples 136 to 145 compounds were prepared by the methods described above.

| Example # | Structure | Characterization MS: (M + H)$^-$ |
|---|---|---|
| 136 | 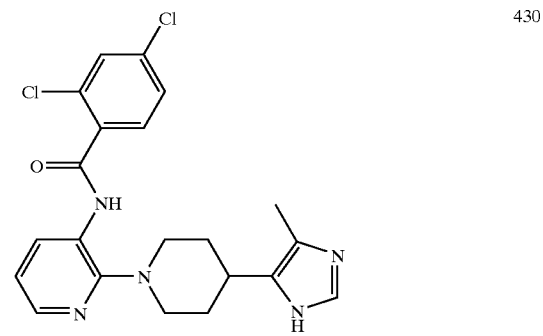 | 430 |
| 137 | 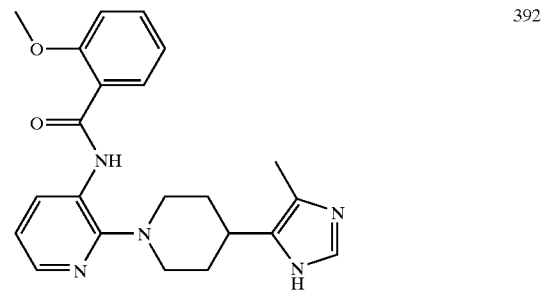 | 392 |
| 138 | 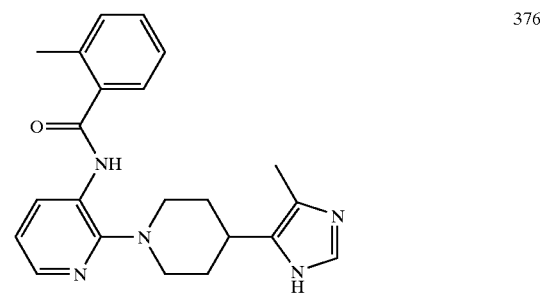 | 376 |

| Example # | Structure | Characterization MS: (M + H)⁻ |
|---|---|---|
| 139 | 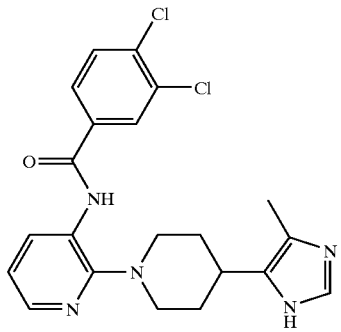 | 430 |
| 140 | 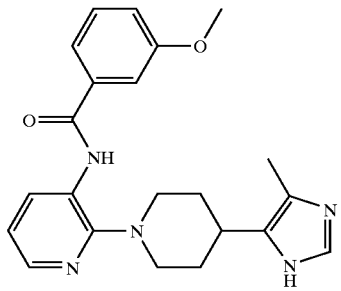 | 392 |
| 141 | 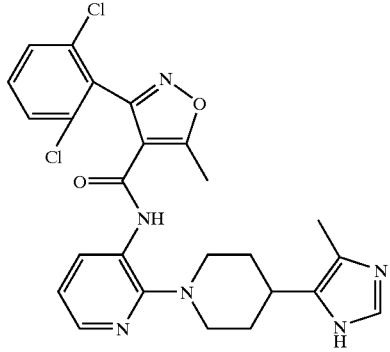 | 511 |
| 142 | 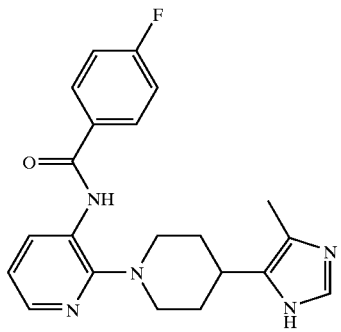 | 380 |

-continued
| Example # | Structure | Characterization MS: (M + H)⁻ |
|---|---|---|
| 143 | 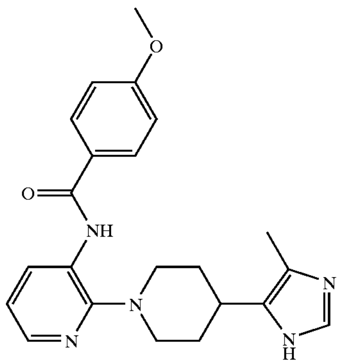 | 392 |
| 144 | 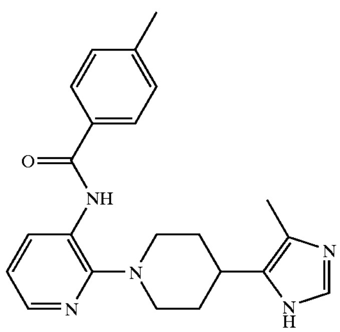 | 376 |
| 145 | 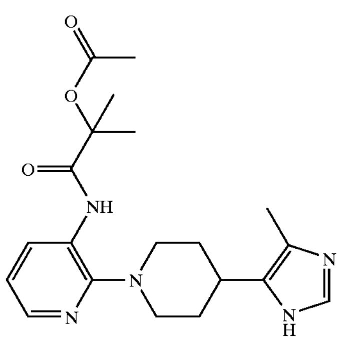 | 386 |
EXAMPLE 146
A.
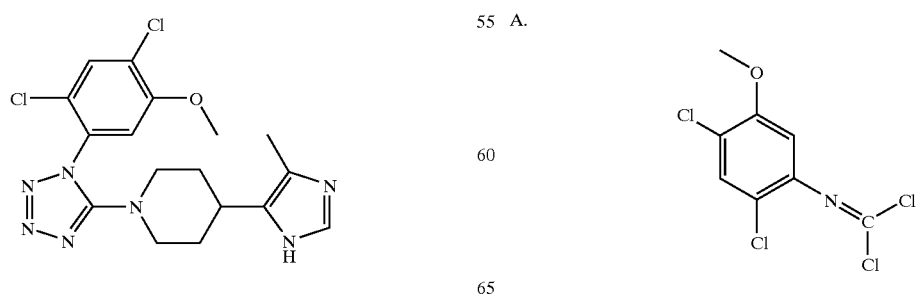

Excess chlorine gas was bubbled through a stirred solution of 3-methoxyphenyl-isothiocyanate (2 g, 0.012 mol) in CCl$_4$ (50 mL) at 0° C. and the reaction mixture was kept at RT for 24 hrs. The solvent was removed under vacuum to give a crude mixture containing the title compound.

B.

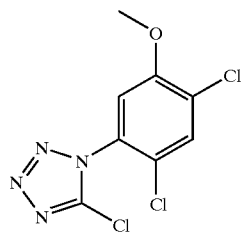

To a stirred solution of crude step A compound (3.26 g, 0.012 mol) in toluene (25 mL) at room temperature was added a solution of sodium azide (1.17 g, 0.018 mol) and tetrabutylammonium bromide (0.27 g, 0.84 mmol) in water (5 mL). The reaction mixture was stirred at room temperature overnight. The aqueous layer was saturated with NaCl and the organic layer was separated. The aqueous layer was then extracted with toluene. The organic layers were combined, dried over sodium sulfate and concentrated. The resulting residue was purified by silica gel chromatography (10% ethylacetate in hexane) to give 1.5 g of the title compound as a tan solid.

C.

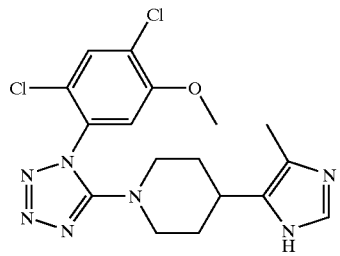

To a stirring suspension of the step A Example 127 compound (20 mg, 0.084 mmol) in DMF (1 mL) was added the step B compound from above (28 mg, 0.101 mmol), followed by the addition of N,N-ethyldiisopropylamine (33 mg, 0.252 mmol). The reaction mixture was heated at 90° C. overnight, concentrated and the crude product was purified by preparative HPLC as described for Example 1 to give the title compound (10 mg, 23%) as TFA salt; MS: m/z 408 (M+H)$^+$.

The following Examples 147 to 155 compounds were prepared by the methods described above.

| Example # | Structure | Characterization MS: (M + H)$^=$ |
|---|---|---|
| 147 | 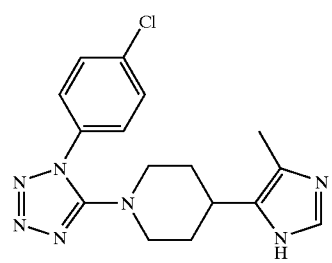 | 344 |
| 148 | 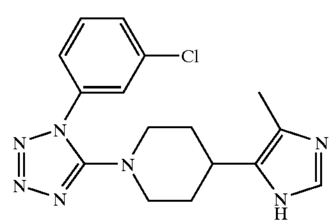 | 344 |
| 149 | 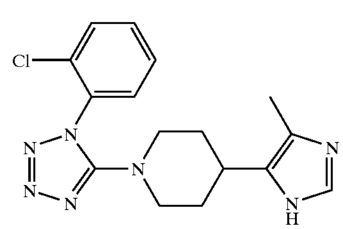 | 344 |

-continued

| Example # | Structure | Characterization MS: (M + H)⁻ |
|---|---|---|
| 150 | 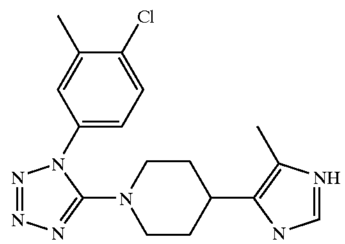 | 358 |
| 151 | 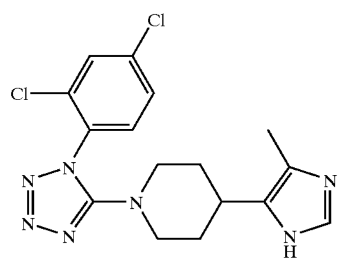 | 378 |
| 152 | 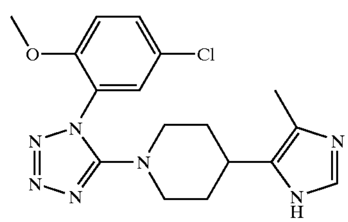 | 374 |
| 153 | 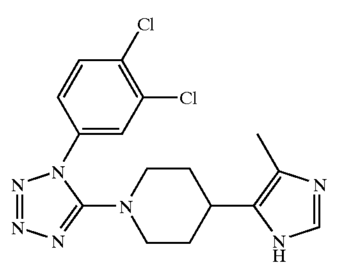 | 379 |
| 154 | 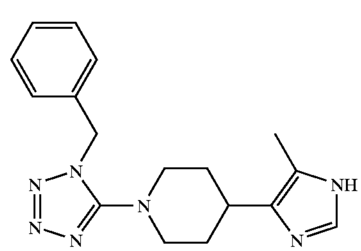 | 324 |
| 155 | 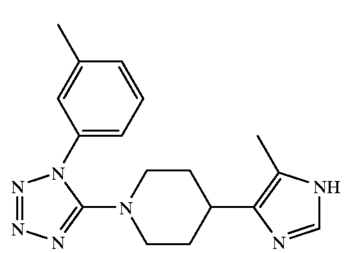 | 324 |

EXAMPLE 156

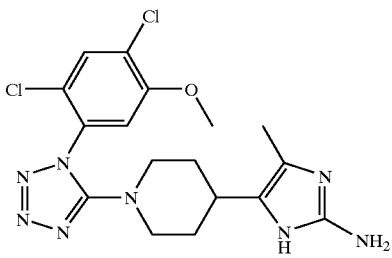

A.

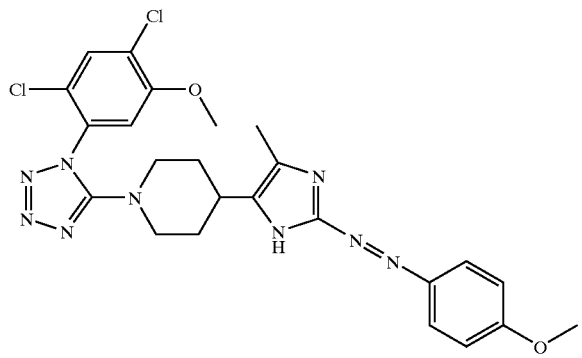

To a stirred solution of the title compound of Example 146 (28 mg, 0.044 mmol) in methanol at 0° C. was added 2 M Na₂CO₃ in water (2.5 mL), followed by the addition of 4-methoxybenzenediazonium tetrafluoroborate (11 mg) in 1 ml of water. The reaction mixture was stirred at 0° C. for 30 min. Then the reaction mixture was extracted with ethyl acetate twice. The organic layer was combined and dried over magnesium sulfate. After the magnesium sulfate was filtered off, the solvent was removed to give the title compound as a yellow/orange solid.

B.

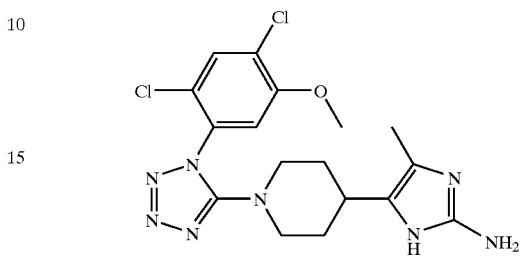

The crude compound of step A was dissolved in 2% HCl in methanol solution (10 mL). Then, to this yellow solution was added PtO₂ (10 mg) and the solution was stirred under hydrogen for 30 min until all the yellow color disappeared. The reaction mixture was filtered and the filtrate was concentrated. The crude residue was purified by preparative HPLC (as described for the title compound of Example 1) to give the title compound (14 mg) as TFA salt in 499 yield; MS: m/z 423 (M+H)⁺.

The following Examples 157 to 164 compounds were prepared by the methods described above.

| Example # | Structure | Characterization MS: (M + H)⁺ |
|---|---|---|
| 157 | 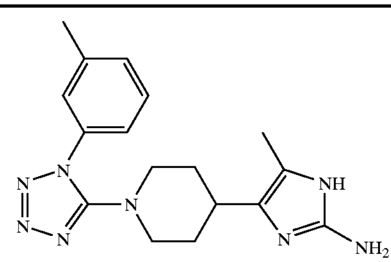 | 339 |
| 158 | 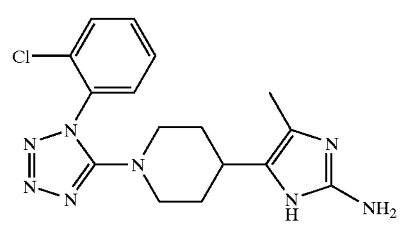 | 359 |
| 159 | 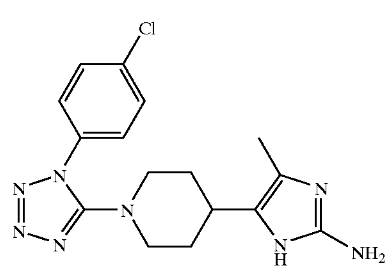 | 359 |

| Example # | Structure | Characterization MS: (M + H)+ |
|---|---|---|
| 160 | 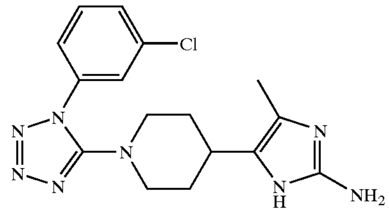 | 359 |
| 161 | 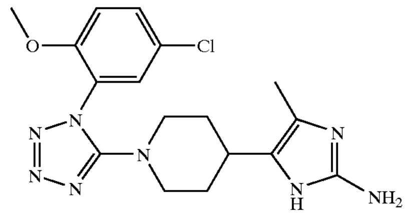 | 389 |
| 162 | 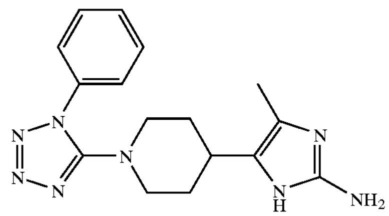 | 325 |
| 163 | 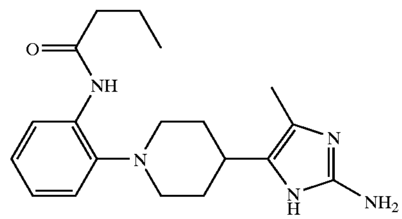 | 342 |
| 164 | 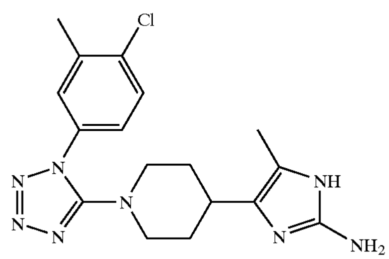 | 373 |

EXAMPLE 165

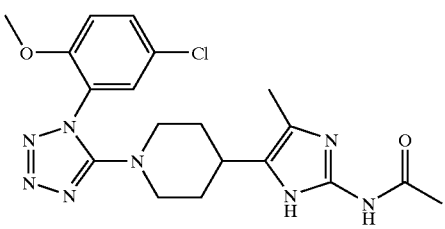

A mixture of the aminoimidazole (10 mg, 0.016 mmol) from Example 161, acetic anhydride (41 mg, 0.40 mmol) and pyridine (3 mL) was stirred at ambient temperature. LC-MS was used to monitored the reaction. The reaction was quenched with 2N NH3 in methanol (2 mL) and stirring was continued for an additional 1 hr. The solvent was removed in vacuo and the residue subjected to preparative HPLC (C18 column/water-MeOH-TFA 90:10:0.1 to 10:90:0.1 gradient) to afford the title compound (off-white solid, 0.9 mg, 85% yield) as a TFA salt; MS: m/z 431 (M+H)+.

The following Examples 166 to 168 compounds were prepared according to the procedure described above.

| Example # | Structure | Characterization MS: (M + H)+ |
|---|---|---|
| 166 | 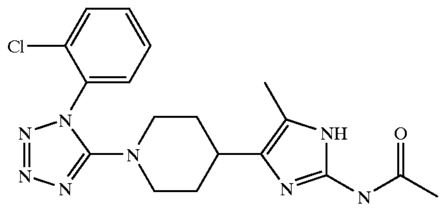 | 401 |
| 167 | 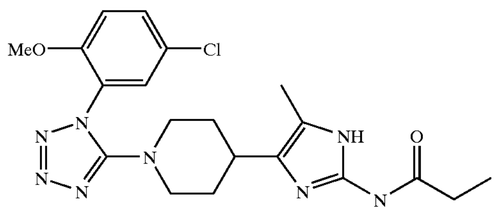 | 445 |
| 168 | 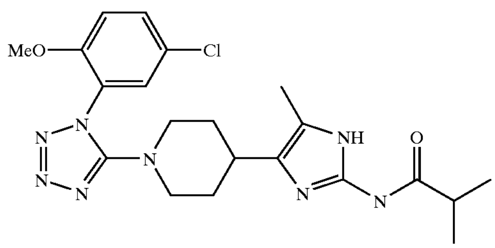 | 459 |

EXAMPLE 169

A.

B.

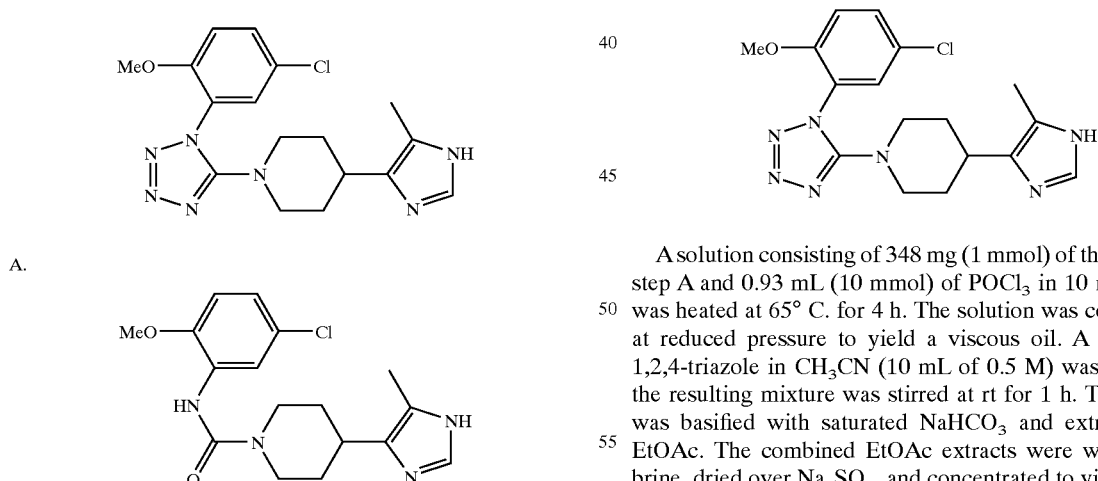

Solid 5-chloro-2-methoxyphenylisocyanate (0.77 g, 4.19 mmol) was added to a solution containing 1.0 g (4.19 mmol) of the bis hydrochloride salt of 4-(4-piperidine)-5-methylimidazole (step A Example 127) and 935 mg (9.24 mmol) of triethylamine in 30 mL of $CH_2Cl_2$. The solution was stirred for 2 h at RT and concentrated to yield 1.4 g of the crude desired urea as a white solid. The crude material was used without further purification.

A solution consisting of 348 mg (1 mmol) of the urea from step A and 0.93 mL (10 mmol) of $POCl_3$ in 10 mL of THF was heated at 65° C. for 4 h. The solution was concentrated at reduced pressure to yield a viscous oil. A solution of 1,2,4-triazole in $CH_3CN$ (10 mL of 0.5 M) was added and the resulting mixture was stirred at rt for 1 h. The solution was basified with saturated $NaHCO_3$ and extracted with EtOAc. The combined EtOAc extracts were washed with brine, dried over $Na_2SO_4$, and concentrated to yield 760 mg of a viscous yellow oil. The crude residue was dissolved in 10 mL of MeOH, treated with 2 mL of a 5 M $NaN_3$ solution in water, and heated at 70° C. for 5 h. The solution was concentrated and extracted with EtOAc. The combined extracts were concentrated and purified by preparative HPLC (as described for the title compound of Example 1) to yield 250 mg of the TFA salt of the title compound as white solid; MS: m/z 374 $(M+H)^+$.

The following Examples 170 to 172 compounds were prepared by the methods described above.

| Example # | Structure | Characterization MS: (M + H)+ |
|---|---|---|
| 170 | 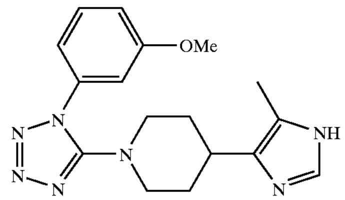 | 340 |
| 171 | 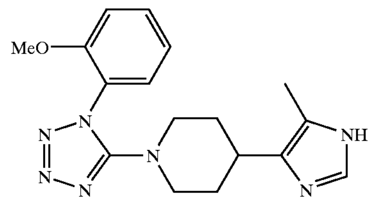 | 340 |
| 172 | 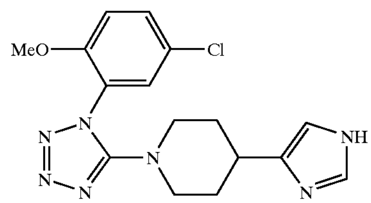 | 360 |

EXAMPLE 173

A.

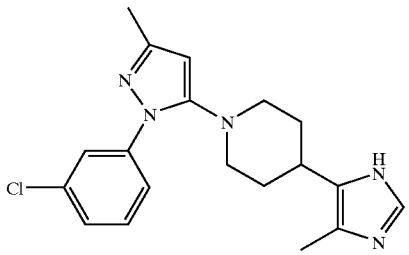

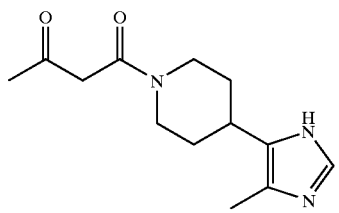

To a mixture of 1.5 g (6.3 mmol) of 4-(5-methylimidazo-4-yl)piperidine hydrochloride salt (the compound of Example 127, step A)in 20 mL of DMF was added 1.5 g (15.2 mmol) of triethylamine at ambient temperature. The mixture was stirred for 30 min at ambient temperature and 0.63 g (7.6 mmol) of diketene was added dropwise. The resulting mixture was stirred for 18 hrs at ambient temperature and concentrated. The residue mixture was dissolved in methanol and purified by preparative HPLC to give 2.1 g (90%) of the title compound.

B.

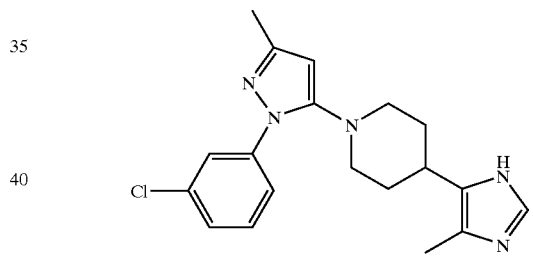

To a solution of 100 mg (0.4 mmol) of the step A compound and 72 mg (0.4 mmol) 3-chlorophenylhydrazine in 20 mL of ethanol was added 6 µL of methansulfonic acid (J. P. Bouillon, C. Ates, Z. Janousek, H. G. Viehe, Tetrahedron Lett. 34, 1993, 5075). The solution was stirred for 4 hrs at ambient temperature, 100 µL of pyridine was added and concentrated. The residue was taken up with 10 mL of pyridine and 135 mg (0.88 mmol) of POCl$_3$ at ambient temperature. The resulting red mixture was stirred for 18 hrs at ambient temperature and concentrated. The residue was taken up with 10% methanol in water and purified by preparative HPLC to give 30 mg (20%) of the title compound; MS: m/z 356 (M+H)+.

EXAMPLE 174

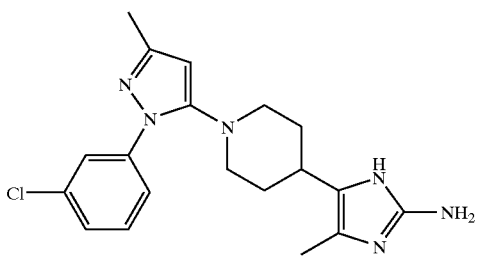

To a solution of 8 mg (0.02 mmol) of the title compound of Example 173 in 5 mL methanol was added 2 mL of 2 M sodium carbonate solution in water at 0° C. (A. Commercon, C. Gueremy, Tetrahedron Lett. 32, 1993, 1419). The solution was stirred for 5 min at 0° C. and 4.4 mg (0.04 mmol) 4-Methoxyphenyl diazonium tetrafluoroborate was added and stirred for 2 hrs at 0° C. and then placed in refrigerator overnight. The reaction mixture was extracted with ethyl acetate. The organic layer was dried with magnesium sulfate and concentrated. The reaction was then taken up in 10 mL of methanol and acidified to pH 3 with a solution of 2% hydrochloric in methanol. To this solution was added 2 mg of 25% w/w PtO2 and hydrogenated at ambient pressure. The mixture was stirred for 15 min at the point the mixture was decolorized. The reaction mixture was then filtered through celite and the filtrate was concentrated. The residue was taken up in minimum amount of methanol and added two drops of TFA and purified by preparative HPLC to give 4 mg (85%) of title compound; MS: m/z 371 (M+H)$^+$.

EXAMPLE 175

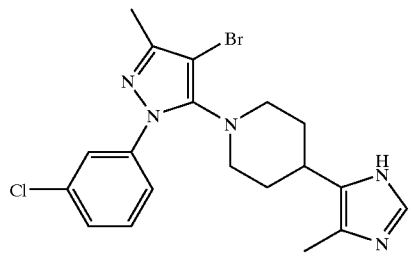

To a solution of 50 mg (0.14 mmol) of the title compound of Example 173 in 5 mL of chloroform and 2 mL of acetic acid was added bromine at 0° C. The solution was stirred for 1 hr at 0° C. and warmed to ambient temperature. The mixture was concentrated and the crude product was purified by preparative HPLC as described for Example 1 to give 23 mg (38%) of title compound as TFA salt; MS: m/z 434 (M+H)$^+$.

The following Examples 176 to 227 compounds were prepared by the methods described above.

| Example # | Structure | Characterization MS: (M + H)$^+$ |
|---|---|---|
| 176 | 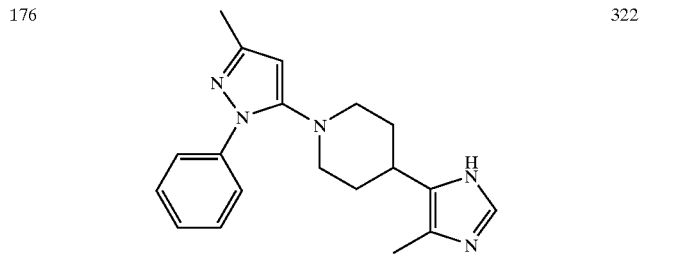 | 322 |
| 177 | 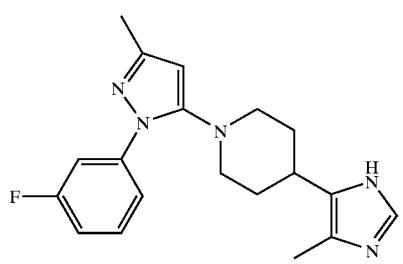 | 340 |
| 178 | 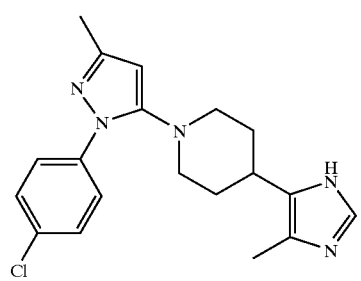 | 356 |

-continued

| Example # | Structure | Characterization MS: (M + H)+ |
|---|---|---|
| 179 | 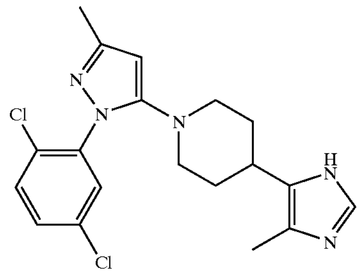 | 391 |
| 180 | 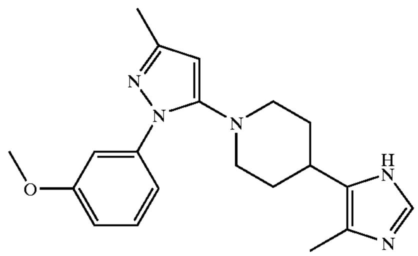 | 352 |
| 181 | 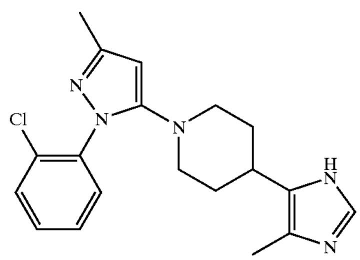 | 356 |
| 182 | 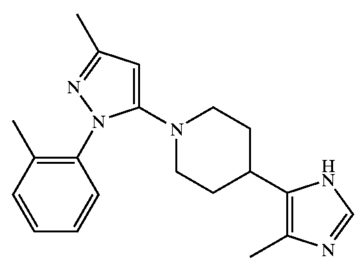 | 336 |
| 183 | 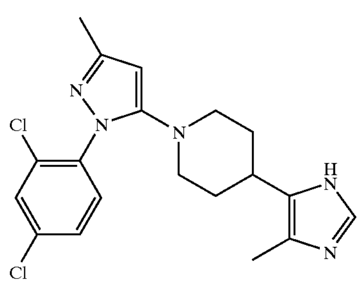 | 391 |

-continued

| Example # | Structure | Characterization MS: (M + H)+ |
|---|---|---|
| 184 | 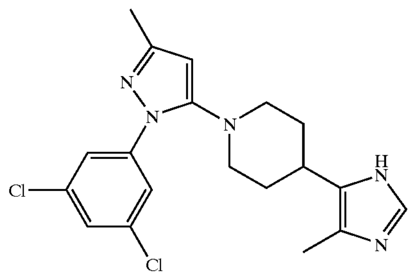 | 391 |
| 185 | 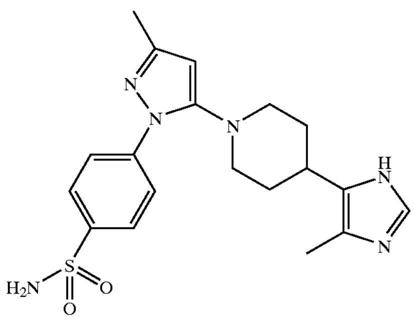 | 401 |
| 186 | 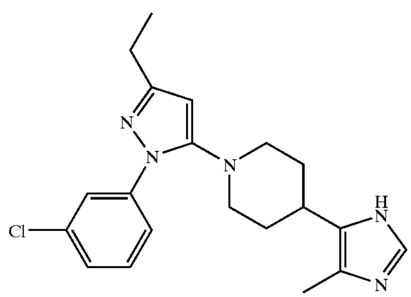 | 370 |
| 187 | 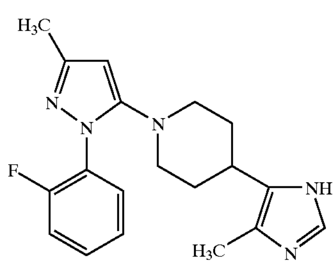 | 340 |
| 188 | 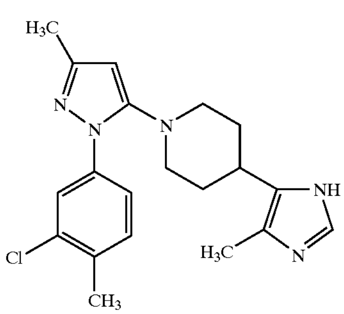 | 370 |

-continued

| Example # | Structure | Characterization MS: (M + H)+ |
|---|---|---|
| 189 | 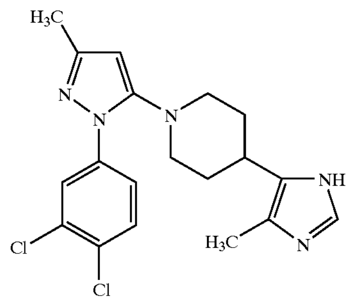 | 391 |
| 190 | 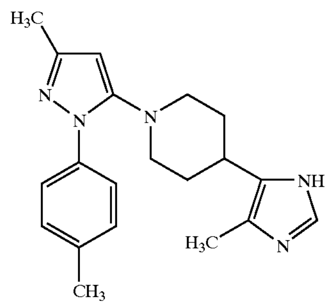 | 336 |
| 191 | 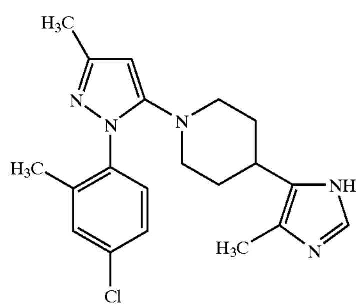 | 370 |
| 192 | 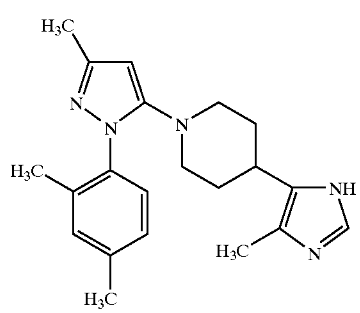 | 350 |
| 193 | 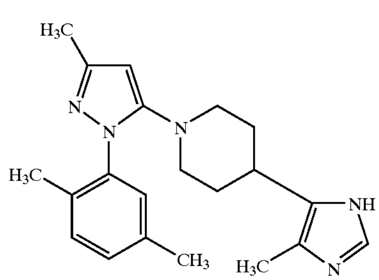 | 350 |

-continued

| Example # | Structure | Characterization MS: (M + H)+ |
|---|---|---|
| 194 | 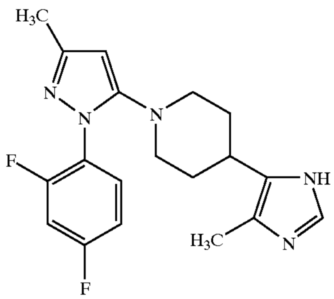 | 358 |
| 195 | 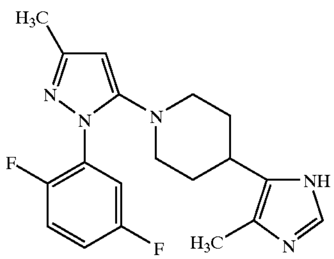 | 358 |
| 196 | 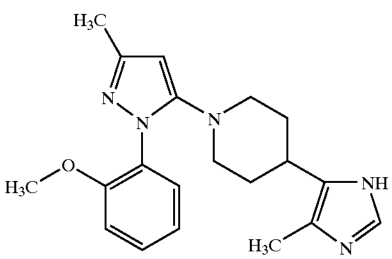 | 352 |
| 197 | 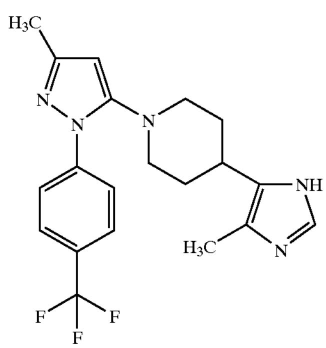 | 390 |
| 198 | 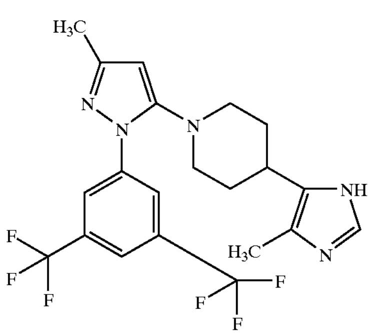 | 458 |

-continued

| Example # | Structure | Characterization MS: (M + H)+ |
|---|---|---|
| 199 | 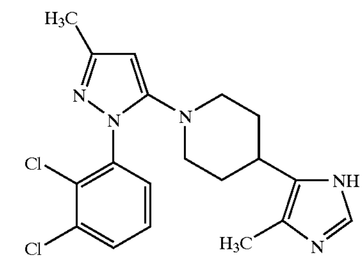 | 391 |
| 200 | 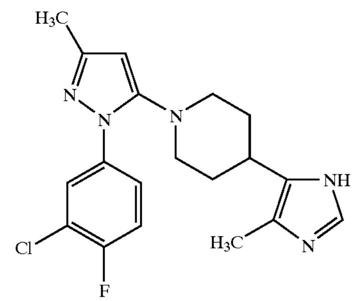 | 374 |
| 201 | 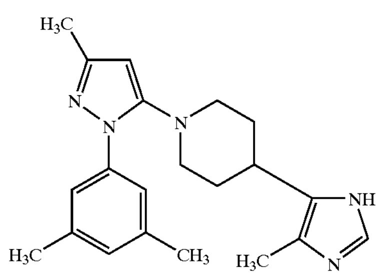 | 350 |
| 202 | 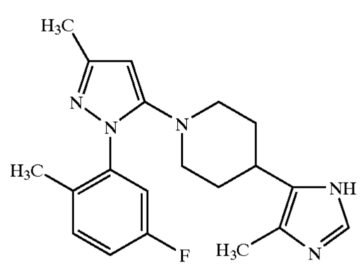 | 354 |
| 203 | 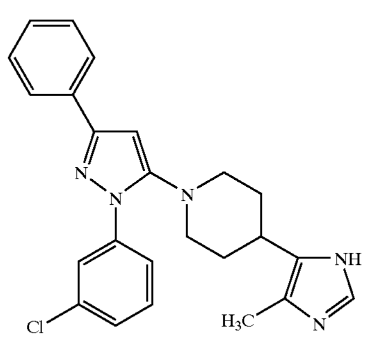 | 418 |

| Example # | Structure | Characterization MS: (M + H)+ |
|---|---|---|
| 204 | 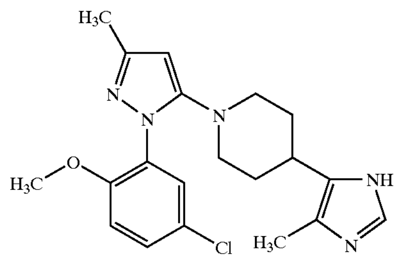 | 386 |
| 205 | 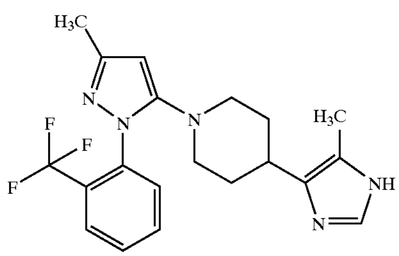 | 390 |
| 206 | 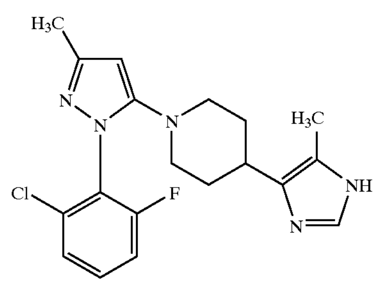 | 374 |
| 207 | 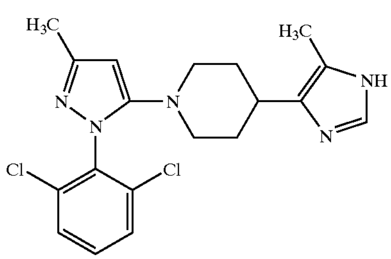 | 391 |
| 208 | 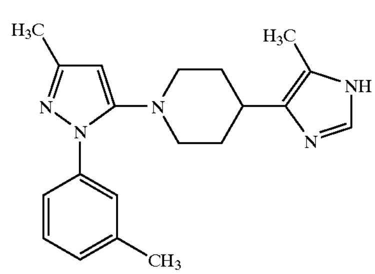 | 336 |

-continued

| Example # | Structure | Characterization MS: (M + H)+ |
|---|---|---|
| 209 | 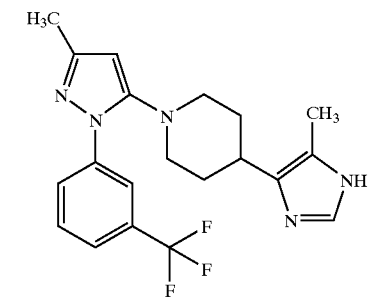 | 389 |
| 210 | 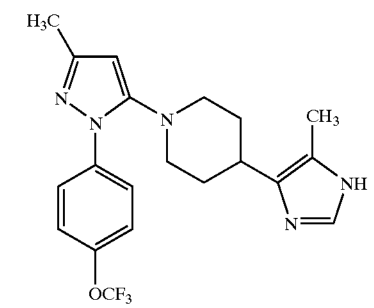 | 405 |
| 211 | 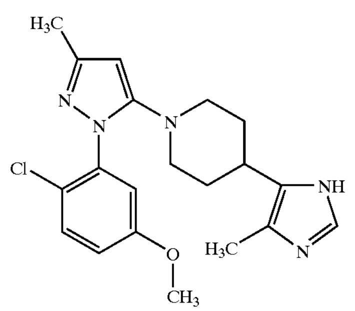 | 386 |
| 212 | 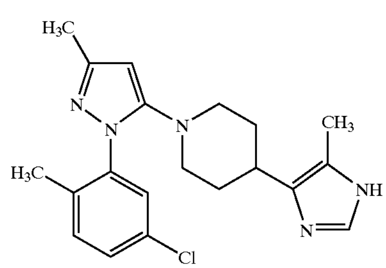 | 370 |
| 213 | 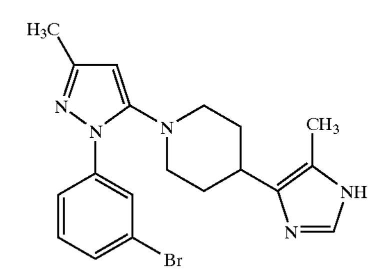 | 401 |

-continued

| Example # | Structure | Characterization MS: (M + H)+ |
|---|---|---|
| 214 | 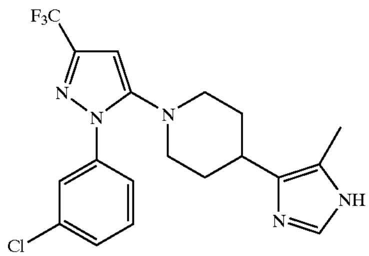 | 410 |
| 214a | 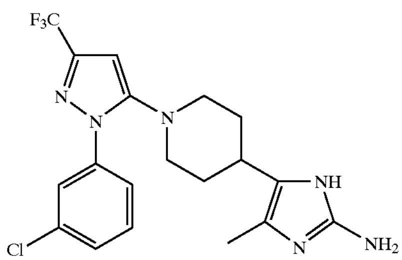 | 425 |
| 214b | 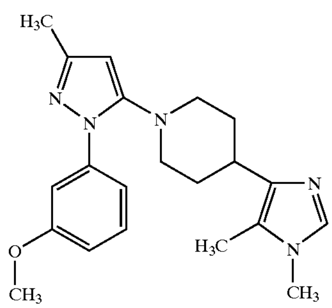 | 366 |
| 214c | 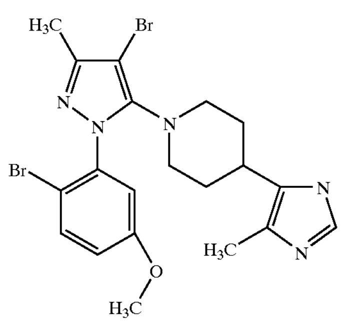 | 510 |
| 214d | 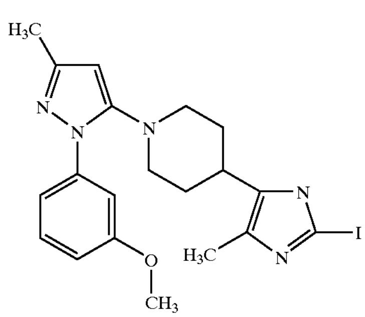 | 478 |

-continued

| Example # | Structure | Characterization MS: (M + H)+ |
|---|---|---|
| 215 | 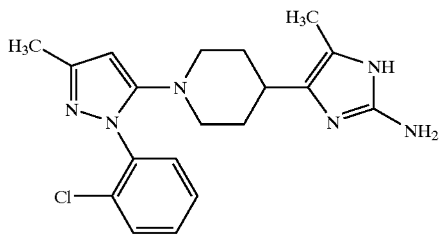 | 371 |
| 216 | 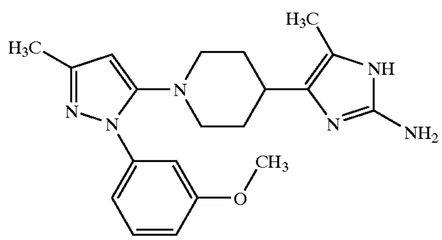 | 367 |
| 217 | 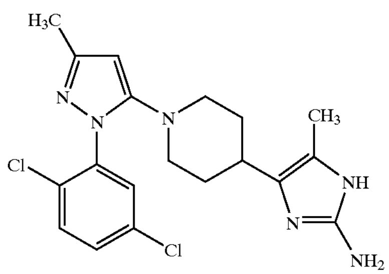 | 406 |
| 218 | 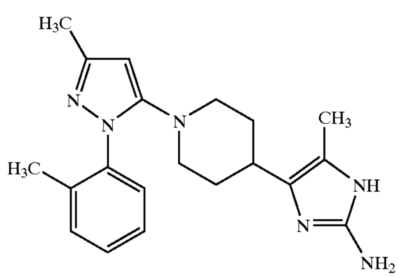 | 351 |
| 219 | 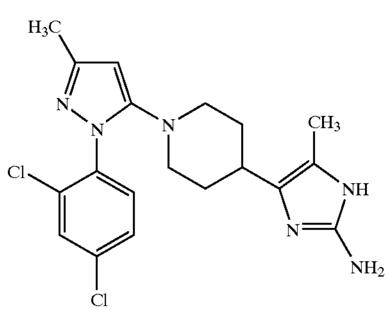 | 406 |

-continued
| Example # | Structure | Characterization MS: (M + H)+ |
|---|---|---|
| 220 | 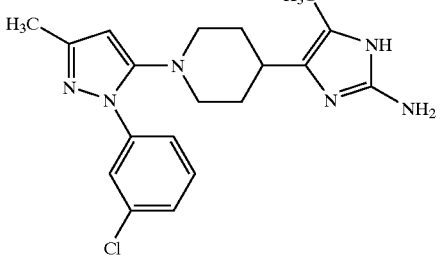 | 371 |
| 221 | 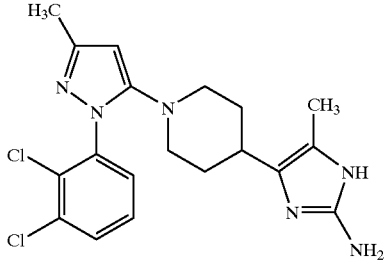 | 406 |
| 222 | 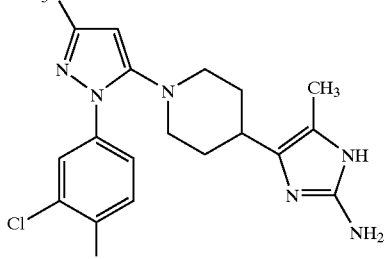 | 389 |
| 223 | 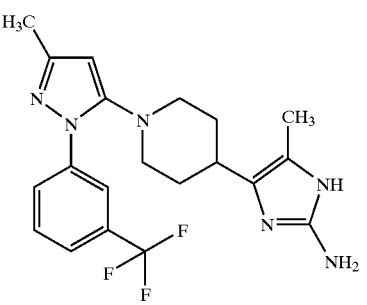 | 405 |
| 224 | 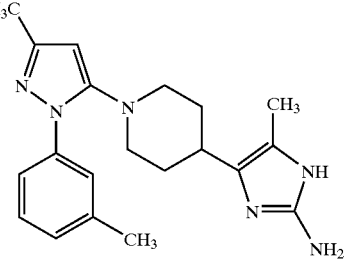 | 351 |

-continued

| Example # | Structure | Characterization MS: (M + H)+ |
|---|---|---|
| 225 | 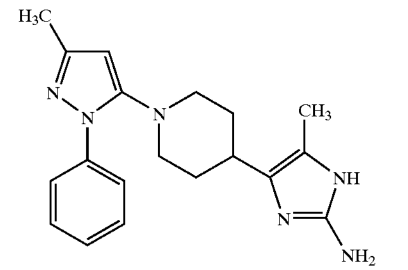 | 337 |
| 226 | 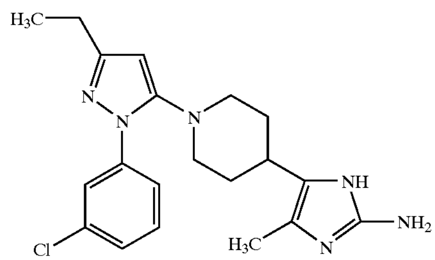 | 385 |
| 227 | 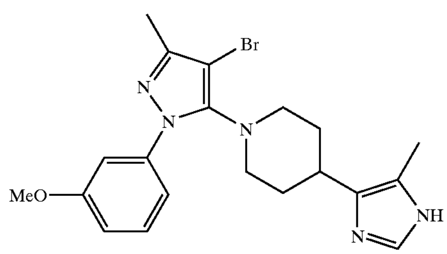 | 431 |

EXAMPLE 228

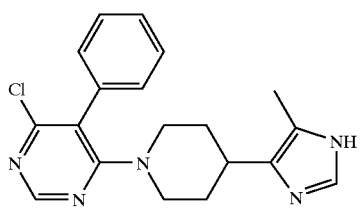

A.

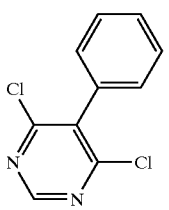

B.

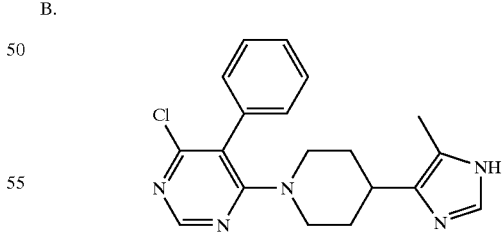

A solution of NaOEt in EtOH was prepared by dissolving 460 mg (20 mmol) of sodium in 15 mL of EtOH. Solid 2-phenylmalonamide and ethyl formate were added sequentially and the solution was heated at 50° C. for 5 h. The solution was cooled and water was added to dissolve the majority of the thick white suspension. The remaining undisolved unreacted malonamide was filtered off. The filtrate was acidified and the dihydroxypyrimidine was collected by filtration. The crude product was dried under vacuum to yield 1.2 g of a pale yellow solid that was used without further purification.

The crude dihydroxypyrimidine was heated at 100° C. in 10 mL of POCl₃ for 2 h. The excess POCl₃ was removed under reduced pressure and the resulting residue was diluted with CH₂Cl₂, washed with water, dried (MgSO₄), and concentrated to yield 950 mg of 4,6-dichloro-5-phenylpyrimidine as an off white solid. The crude product was used without further purification.

A suspension of 237 mg (1.0 mmol) of the bis hydrochloride salt of the step A compound of Example 127 (225 mg, 1.0 mmol) of 4,6-dichloro-5-phenylpyrimidine, and 276 mg (2 mmol) of K₂CO₃ in 5 mL of diglyme was heated at 150° C. for 30 min. The solution was cooled, diluted with MeOH and water, and purified by preparative HPLC (as described for the title compound of Example 1) to yield 0.480 mg of the desired compound as a bis TFA salt; MS: m/z 354 (M+H)+.

The following Examples 229 to 233 compounds were prepared by the methods described above.

| Example # | Structure | Characterization MS: (M + H)+ |
|---|---|---|
| 229 | 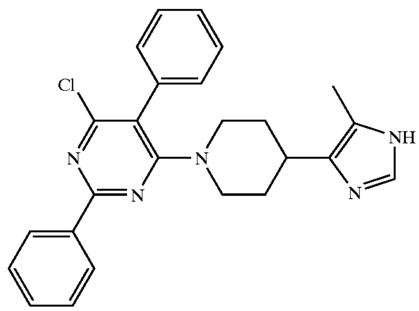 | 430 |
| 230 | 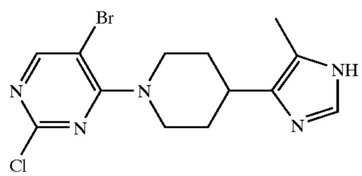 | 356 |
| 231 | 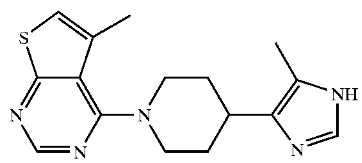 | 314 |
| 232 | 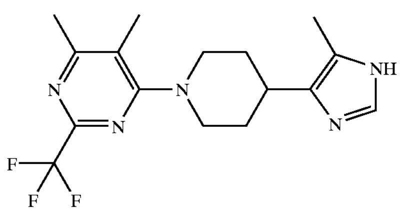 | 340 |
| 233 | 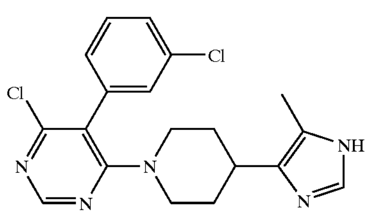 | 388 |

EXAMPLE 234

A.

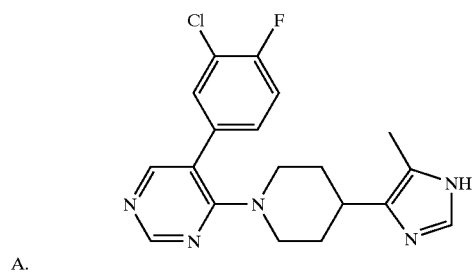

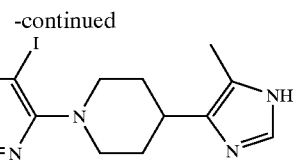

The title compound was prepared from 4-chloro-5-iodopyrimidine in a manner similar to that described for the preparation of the title compound of Example 228.

B.

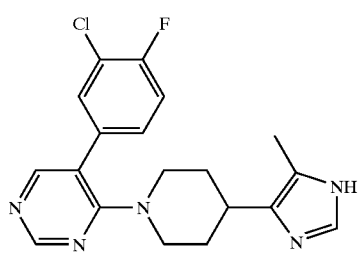

A suspension consisting of 580 mg (1.57 mmol) of the compound from step A, 560 mg (3.2 mmol) of 3-chloro-4-fluorophenyl boronic acid, 6 mL of 1.0 M $Na_2CO_3$, and 50 mg of $(Ph_3P)_4Pd$ in 10 mL of DMF was heated at 80° C. for 24 hrs. The solution was filtered, concentrated, and purified by preparative HPLC (as described for the title compound of Example 1) to yield 616 mg of the bis TFA salt of the desired compound as a pale yellow oil; MS: m/z 372 (M+H)+.

The following Examples 235 to 248c compounds were prepared by the methods described above.

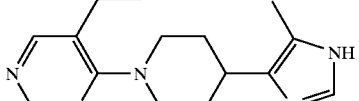

| Example # | Structure | Characterization MS: (M + H)+ |
|---|---|---|
| 235 | 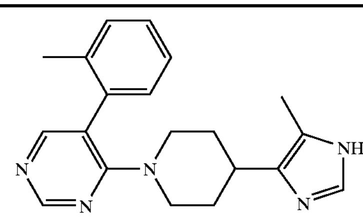 | 334 |
| 236 | 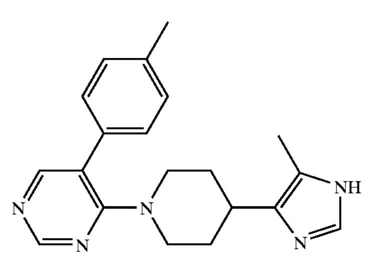 | 334 |

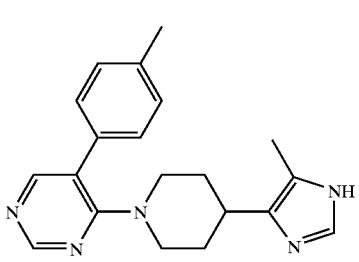

-continued

| Example # | Structure | Characterization MS: (M + H)+ |
|---|---|---|
| 237 | 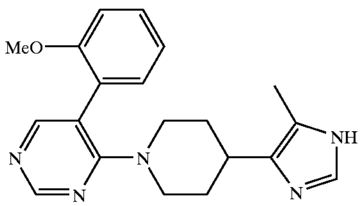 | 350 |
| 238 | 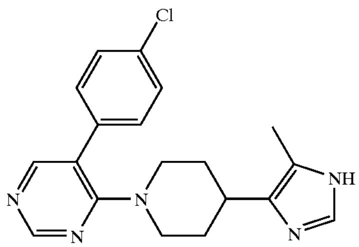 | 354 |
| 239 | 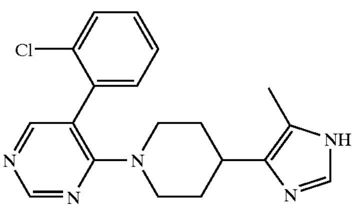 | 354 |
| 240 | 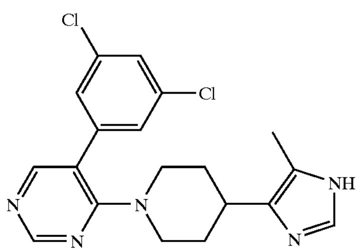 | 388 |
| 241 | 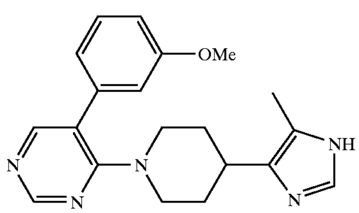 | 350 |
| 242 | 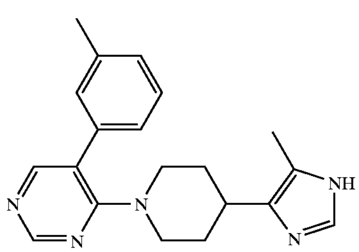 | 334 |

-continued

| Example # | Structure | Characterization MS: (M + H)+ |
|---|---|---|
| 243 | 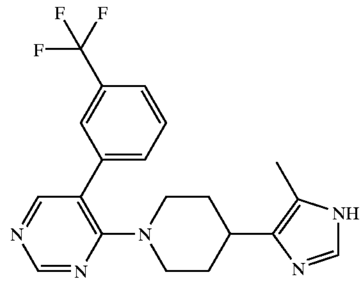 | 388 |
| 244 | 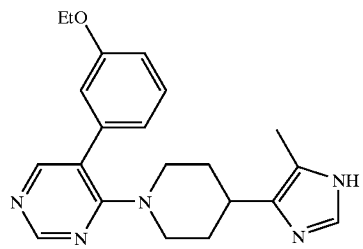 | 364 |
| 245 | 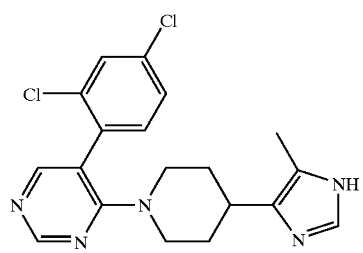 | 388 |
| 246 | 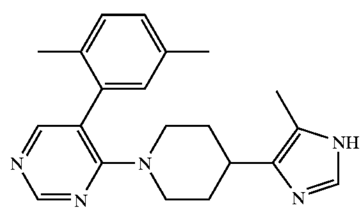 | 348 |
| 247 | 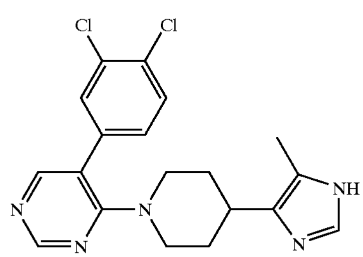 | 88 |
| 248 | 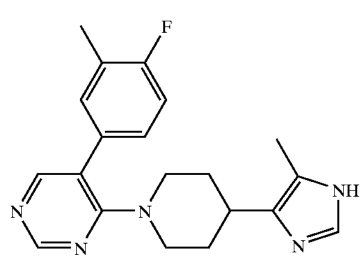 | 352 |

-continued

| Example # | Structure | Characterization MS: (M + H)+ |
|---|---|---|
| 248a | 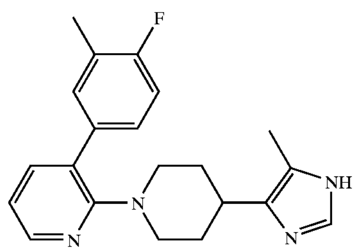 | 351 |
| 248b | 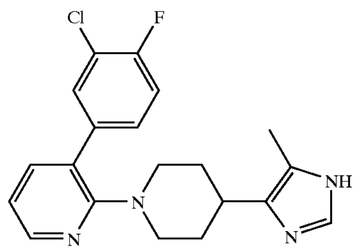 | 371 |
| 248c | 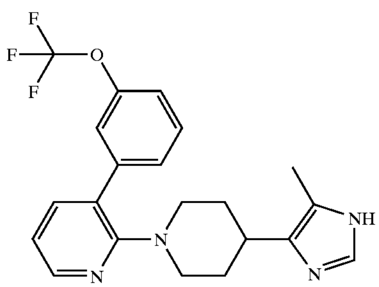 | 403 |
| 249 | 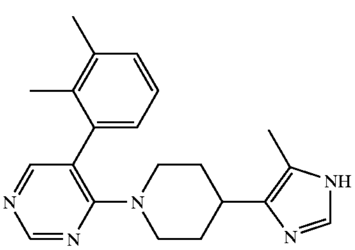 | 348 |
| 250 | 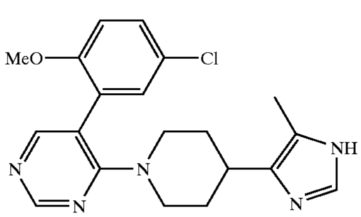 | 384 |
| 251 | 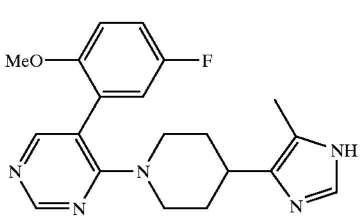 | 368 |

EXAMPLE 252

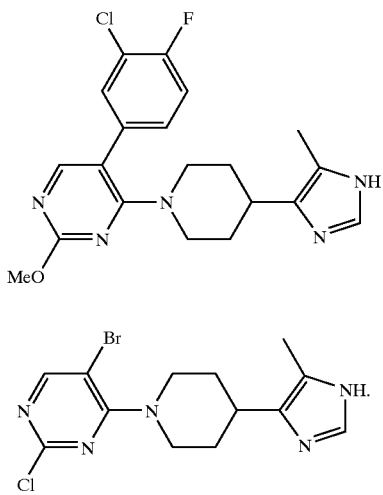

A.

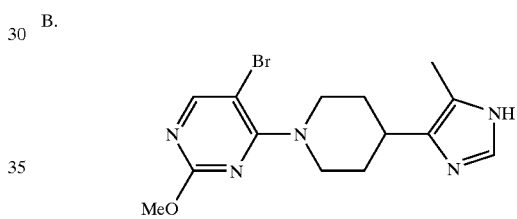

The title compound was prepared from S-bromo-2,4-dichloropyrimidine in a manner similar to that described for the preparation of the title compound of Example 228.

B.

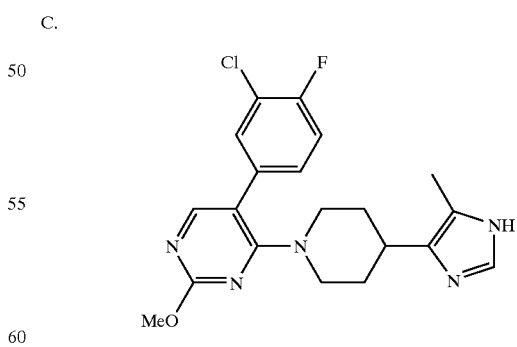

Chloropyrimidine from step A (100 mg) was treated with excess NaOMe in MeOH at 50° C. for 10 h. The solution was quenched with water, saturated with NaCl, and extracted with EtOAc. The extracts were dried over MgSO$_4$ and concentrated to yield 83 mg of the product as a white solid. No purification was required.

C.

The title compound was prepared from the step B compound and 3-chloro-4-fluorophenyl boronic acid in a manner similar to the described for Example 234 step B; MS: m/z 402 (M+H)+.

The following Examples 253–254 compounds were prepared by the methods similar to those described above.

| Example # | Structure | Characterization MS: (M + H)+ |
|---|---|---|
| 253 | ![structure] | 415 |
| 254 | ![structure] | 457 |

EXAMPLE 255

A solution of 35 mg (0.06 mmol) of the bis TFA salt of the compound of Example 228 in excess NaOEt in EtOH was stirred at RT for 2 days and then heated at 75° C. for 6 hrs. The solution was quenched with TFA and purified by preparative HPLC (as described for the title compound of Example 1) to yield 13 mg of the bis TFA salt of the desired compound as a yellow oil; MS: m/z 364 (M+H)+.

The following Examples 256–257 compounds were prepared by the methods described above.

| Example # | Structure | Characterization MS: (M + H)+ |
|---|---|---|
| 256 | 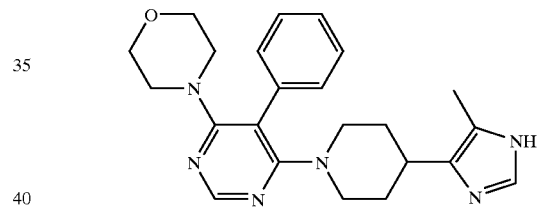 | 350 |
| 257 | 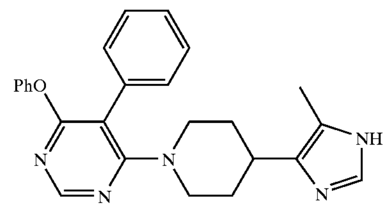 | 412 |

EXAMPLE 258

A solution of 35 mg (0.06 mmol) of the bis TFA salt of the compound of Example 228 was heated in 0.5 mL of neat morpholine at 80° C. for 2 days. The solution was purified directly by preparative HPLC (as described for the title compound of Example 1) to yield 34 mg of the bis TFA salt of the desired compound as a colorless oil; MS: m/z 405 (M+H)+.

The following Example compound was prepared by the methods described above.

| Example # | Structure | Characterization MS: (M + H)+ |
|---|---|---|
| 259 | 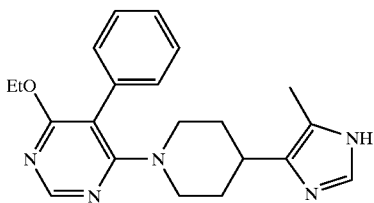 | 403 |

EXAMPLE 260

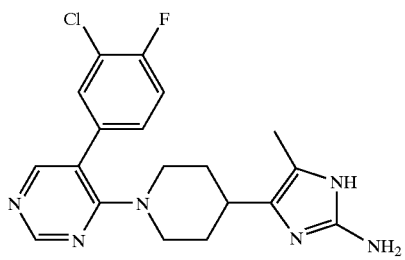

This compound was prepared in a manner similar to that described for the title compound of Example 174; MS: m/z 387 (M+H)$^+$.

EXAMPLE 261

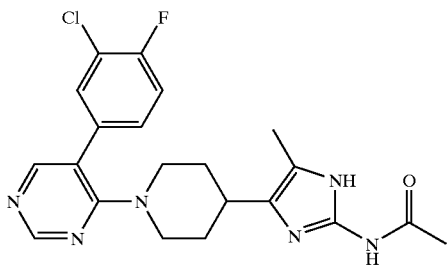

This compound was prepared in a manner similar to that described for the title compound of Example 165; MS: m/z 429 (M+H)$^+$.

EXAMPLE 262

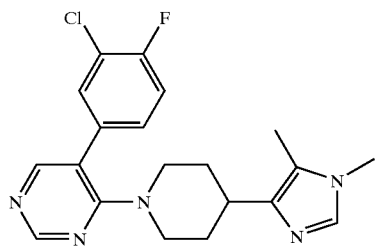

Excess MeI and potassium carbonate were added portionwise to a warm solution of 55 mg (0.092 mmol) of the title compound from example 234 in 3 mL of acetone. The reaction was stopped when only a trace of the starting imidazole could be detected by LC/MS analysis of the reaction mixture. The solution was filtered, concentrated, and purified by gradient flash chromatography on silica gel (20:1:0.1 to 10:1:0.1 CH$_2$Cl$_2$/MeOH/NH$_4$OH) to yield 10 mg of a 10:1 mixture of regioisomers with the major being the title compound; MS: m/z 386 (M+H)$^+$.

EXAMPLE 263

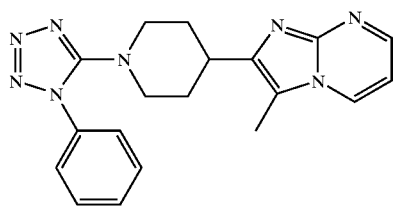

A.

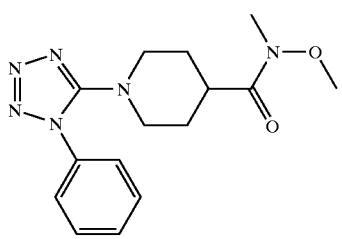

To a mixture of isonipecotic acid (3.0 g, 23.2 mmol) and 5-chloro-1-phenyl-1H-tetrazole (4.20 g, 23.2 mmol) in DMF (25 mL) was added N,N-diisopropylethylamine (8.1 mL, 46.5 mmol). The mixture was heated at 135° C. for 12 h, then cooled to ambient temperature. To the reaction mixture was added EDC (3.9 g, 204 mmol) and HOBT (2.8 g, 20.4 mmol) followed by N,N-diisopropylethylamine (6.5 mL, 37.2 mmol) and O,N-dimethylhydroxylamine hydrochloride (4.53 g, 37.2 mmol). The mixture was stirred at 25° C. for 16 h, then partitioned between ethyl acetate (200 mL) and water (200 mL). The organic layer was washed with saturated aqueous sodium bicarbonate (200 mL) and brine (200 mL) then dried (Na$_2$SO$_4$) and concentrated under reduced pressure. Flash column chromatography (silica, 70% ethyl acetate/hexanes to 100% ethyl acetate) provided the title compound (5.2 g, 72%).

B.

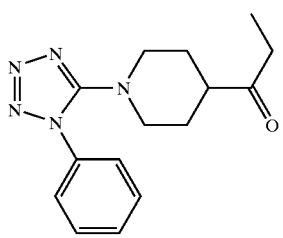

To a solution of the Weinreb amide from step A (1.89 g, 5.98 mmol) in THF (60 mL) at –78° C. was added a solution of ethyl magnesium bromide in THF (6.0 mL, 18.0 mmol) dropwise. The solution was allowed to warm to –25° C. over 1.5 h, then quenched by pouring into rapidly stirred 1N HCl. The solution was extracted with ethyl acetate (200 mL) and the organic layer washed with saturated aqueous sodium bicarbonate (200 mL) and brine (200 mL) then dried (Na$_2$SO$_4$). After concentration under reduced pressure, the residue was purified by flash column chromatography (silica, 40% ethyl acetate in hexanes to 60% ethyl acetate in hexanes) to give the title compound (1.43 g, 84%).

C.

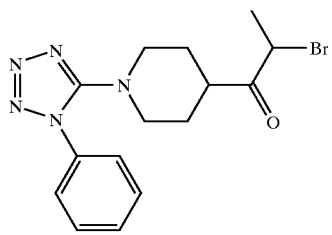

To a solution of the ketone from step B (1.35 g, 4.73 mmol) in THF (47 mL) at −78° C. was added LiHMDS in THF (4.8 mL, 4.73 mmol) dropwise. After 1.5 h at −78° C., a solution of N-bromosuccinimide (0.84 g, 4.73 mmol) in THF (5 mL) was added via canula. The reaction was quenched with the addition of saturated aqueous ammonium chloride (20 mL). The mixture was partitioned between ethyl acetate (150 mL) and water (150 mL). The organic layer was washed with saturated aqueous sodium bicarbonate (100 mL) and brine (100 mL), dried ($Na_2SO_4$) and concentrated under reduced pressure. Flash column chromatography (silica, 30% ethyl acetate in hexanes) provided the title compound (1.12 g, 65%).

D.

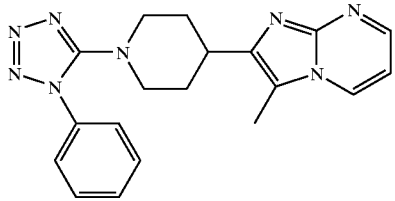

A solution of the bromide from step C (41 mg, 0.11 mmol) and 2-aminopyridine (11.0 mg, 0.11 mmol) in DMF (1 mL) was heated at 90° C. for 2 h. The solvent was removed under reduced pressure and the residue purified by reverse phase preparative HPLC as described for Example 1 to give the title compound (22 mg, 55% yield) as trifluoroacetic acid salt; MS: m/z 361 (M+H)$^+$.

The following Examples 264 to 266 compounds were prepared in a manner similar to that described above.

| Example # | Structure | Characterization MS: (M + H)$^+$ |
|---|---|---|
| 264 | 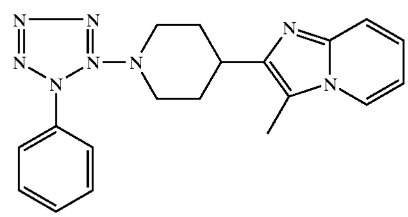 | 360 |
| 265 | 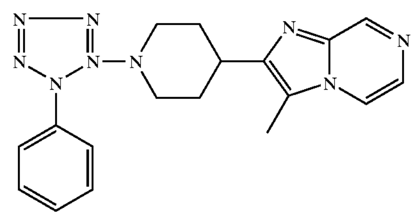 | 361 |
| 266 | 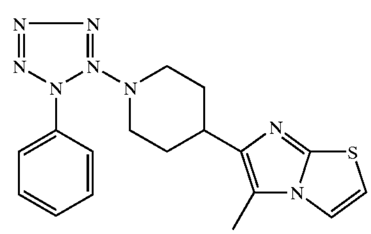 | 366 |

EXAMPLE 267

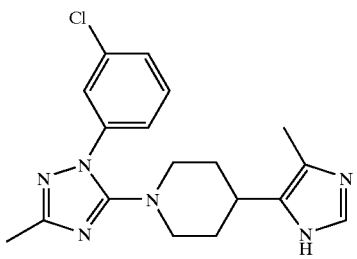

A.

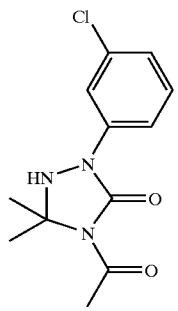

A solution of 3-chlorophenylhydrazine (0.5 g) in 5 mL acetone-water (1:1) was heated at reflux temperature for 2 h and concetrated to afford the corresponding acetone hydrazone as an orange gummy solid (quantitative crude yield). To a portion of this material (0.1 g, 0.55 mmol) in 1 mL toluene was added a solution of acetylisocyanate (102 mg, 1.2 mmol) in 0.25 mL toluene at RT and the mixture was heated at 105° C. for 5 h in a sealed tube. The mixture was concentrated and the gummy residue was extracted with ether. The ether extract was concentrated to afford the title compound as pale gummy solid (80 mg).

B.

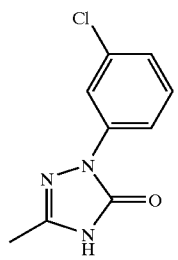

The crude product from part A was dissolved 3 mL of acetic acid-water-sulfuric acid (10:1:0.2) and heated at 95° C. for 15 minutes. The mixture was concentrated and the residue was triturated with water to afford the title compound as an off white solid (70 mg).

C.

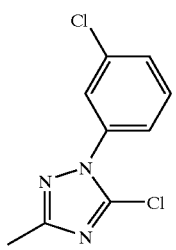

The compound from step B (50 mg) was heated in 1 mL neat POCl₃ at 100° C. for 3 h, concentrated and the resulting brown gummy product was used as such in the next step.

D.

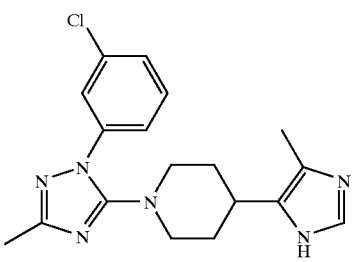

A mixture of the crude product from step C (50 mg), the imidazolyl piperidine from Example 127, step A (66 mg) and triethylamine (0.1 mL) in 0.5 mL N-methylprrolidinone was heated at 125° C. for 24 h, diluted with ethyl acetate, washed with saturated sodium bicarbonate and the organic layer was dried and concentrated to afford crude product. This was purified by preparative HPLC as described for Example 1 to afford the title compound as a yellow gummy solid (26 mg, TFA salt), MS m/z 357 (M+H)⁺.

EXAMPLE 268

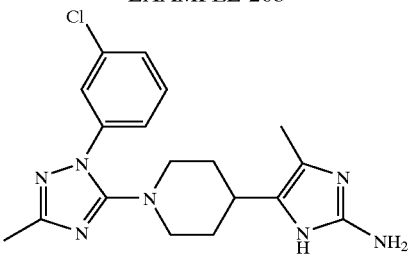

This compound was prepared according to the procedure described for the synthesis of the title compound of Example 174, brown gummy solid (TFA salt), MS m/z 372 (M+H)⁺.

The following Examples 269–270 compounds were prepared employing procedures described herein.

| Example # | Structure | Characterization MS: (M + H)⁺ |
|---|---|---|
| 269 | 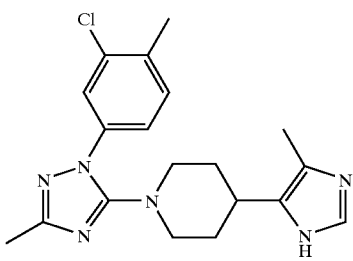 | 371 |

-continued

| Example # | Structure | Characterization MS: (M + H)+ |
|---|---|---|
| 270 | 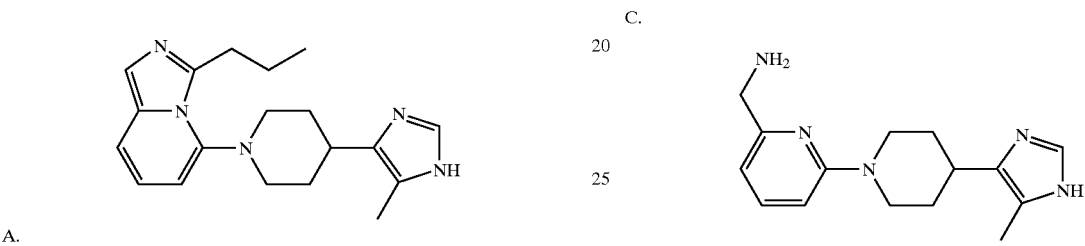 | 386 |

EXAMPLE 271

A.

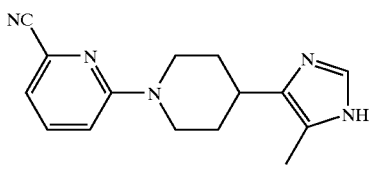

To a solution of the piperidine intermediate from step A, Example 127 (5.0 g, 21.1 mmol) in DMF (150 mL) was added DBU (9.46 mL, 63.3 mmol) followed by 2,6-dibromopyridine (6.5 g, 27.5 mmol). The reaction mixture was stirred at 100° C. for 9 hrs under nitrogen. Then the solvent was removed by rotary evaporation under high vacuum and the resulting residue was purified by silica gel chromatography using 10% methanol in dichloromethane as the eluent to give the title compound (6.6 g, 98% yield).

B.

A mixture of the compound from step A (1.0 g, 3.1 mmol) and CUCN (558 mg, 6.23 mmol) in DMF (31 mL) was heated at 150° C. under nitrogen for 16 hrs. The reaction mixture was then poured into water (100 mL) and the resulting precipitate was removed by filtration. The solid was collected, suspended in TFA (50 mL) and agitated with ultrasonication for 5 mins. After filtration, the filtrate was concentrated and passed through a reverse phase cartridge (C18 silica) using 30% methanol in water as the eluent. The solvent was removed to give the title compound as a solid (398 mg, 48% yield).

C.

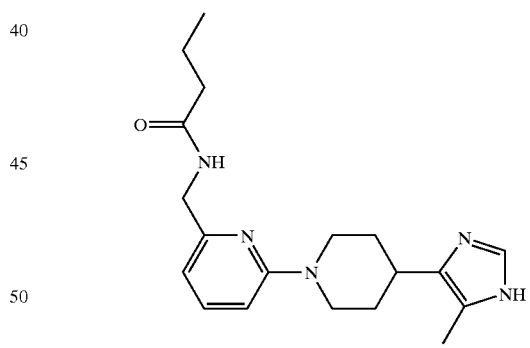

To a solution of the compound from step B (547 mg, 2.0 mmol) in methanol (50 mL) was added concentrated HCl (0.4 mL) and palladium on carbon (10%). The reaction mixture was stirred under 1 atm hydrogen for 14 hrs, then the flask was purged with nitrogen and the reaction mixture was filtered through a pad of celite. The solvent was removed to give the title compound as the hydrochloride salt.

D.

To a solution of the compound from step C (245 mg, 0.80 mmol) in dichloromethane (10 mL) at 0° C. was added N,N-diisopropylethylamine (0.94 mL, 5.42 mmol) followed by butyryl chloride (0.28 mL, 2.7 mmol). The ice bath was removed and the reaction mixture was stirred at 25° C. for 30 mins. The TLC (10% methanol in dichloromethane) analysis showed the presence of a diacylated intermediate (Rf=0.8). The reaction mixture was diluted with ethyl acetate (40 mL) and washed sequentially with water (20 mL), saturated aqueous sodium bicarbonate (20 mL) and brine (20 mL). The organic layer was dried over sodium sulfate. After the sodium sulfate was filtered, the solvent was removed. The resulting crude material was taken up in methanol (5 mL) and treated with 2 drops of 15% aqueous sodium hydroxide. After 5 mins, the solution was rendered acidic wish TFA and subjected to preparative HPLC to give the title compound (205 mg, 67% yield) as a pale red oil.

E.

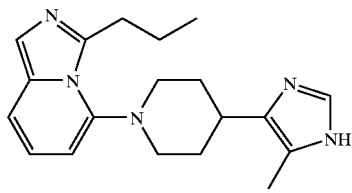

A solution of the compound from step D (72 mg, 0.21 mmol) in POCl3 (5 mL) was heated at 80° C. for 12 hrs. After cooling to room temperature, the reaction mixture was quenced by the dropwise addition of the solution to ice. After melting the remaining ice, the aqueous solution was rendered basic (pH 8–9) with concentrated ammonium hydroxide. The resulting suspension was then extracted with dichloromethane (100 mL) and the organic layer was dried over sodium sulfate. After the filtration, the solvent was removed and the resulting crude was taken up in a solution of 30% methanol in water and treated with 3 drops of TFA to give a precipitate. After filtration, the filtrate was concentrated to give the tilte compound (67 mg, 98% yield); MS m/z 324 (M+H)+.

The following Examples 272 to 278 compounds were prepared by the methods described above.

| Example # | Structure | Characterization MS: (M + H)+ |
|---|---|---|
| 272 | | 296 |
| 273 | | 358 |
| 274 | | 392 |
| 275 | 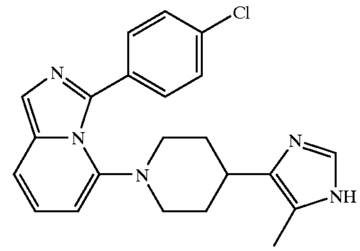 | 392 |
| 276 | 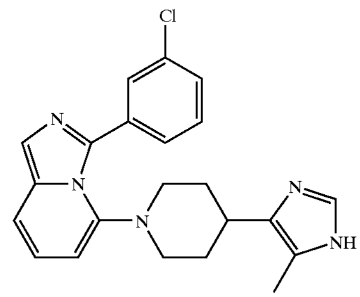 | 392 |
| 277 | 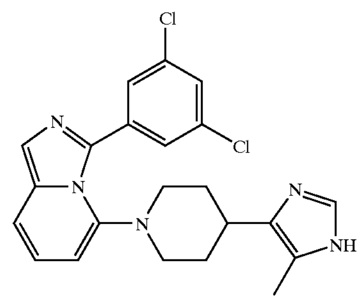 | 427 |
| 278 | 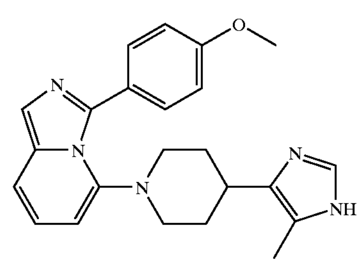 | 388 |

EXAMPLE 279

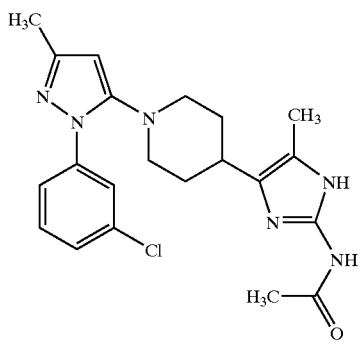

To a solution of 15 mg (0.04 mmol) of the title compound 174 in 5 mL dichloromethane at 0° C. was added 56 μL (0.8 mmol) of acetyl chloride followed by 11 μL of triethyl amine. The solution was stirred for 30 min and 5 mL of 2M NH₃ in methanol was added. The resulting solution was stirred for 4 hr and the solvent was removed. The residue mixture was purified by preparative HPLC to give 2 mg (10%) of the title compound as TFA salt; MS: m/z 413 (M+H)⁺.

EXAMPLE 280

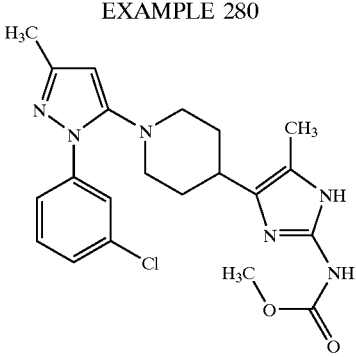

To a solution of 8 mg (0.02 mmols) of the title compound 174 in 5 mL DCM at 0° C. was added 23 μL (0.3 mmoL) of methyl chloroformate followed by 11 μL of triethyl amine. The reaction solution was stirred for 2 hr and 5 mL of 2M NH₃ in methanol was added. The resulting solution was stirred for 18 hr and concentrated. The residual mixture was purified by preparative HPLC to give 1.2 mg (15%) of the title compound as TFA salt; MS: m/z 429 (M+H)⁺.

The following Examples 281–283 compounds were prepared by using the procedures described for the synthesis of Examples 279 and 280 compounds.

| Example # | Structure | Characterization MS: (M + H)⁺ |
|---|---|---|
| 281 | 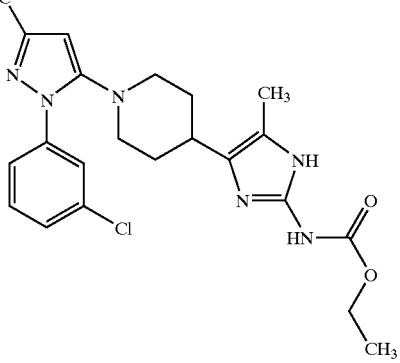 | 443 |
| 282 | 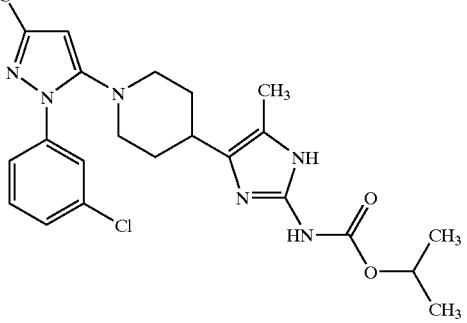 | 457 |

| Example # | Structure | Characterization MS: (M + H)+ |
|---|---|---|
| 283 | 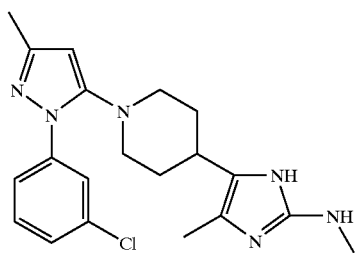 | 427 |

EXAMPLE 284

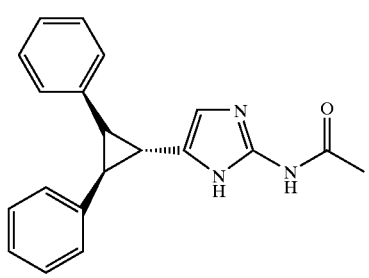

To a solution of 10 mg (0.027 mmol) of the title compound 174 in 5 mL of methanol was add 5 mg (0.04 mmol) of 1H-benzotrizole-1-methanol (A. R. Katritzky, R. P. Musgrave, B. Rachwal, C. Zaklika, Heterocycles, 41, 1995, 34). The solution was stirred for 15 hrs at ambient temperature and 2 mg(0.04 mmol) of sodium borohydride was added. The solution was stirred for 6 hrs at ambient temperature and acidified with TFA. The solution was purified with preparative HPLC to give 1 mg (10%) of the title compound as TFA salt; MS: m/z 385 (M+H)+.

EXAMPLE 285

A.

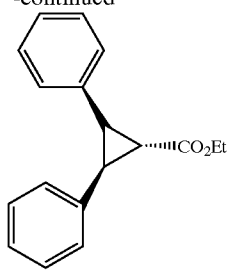

-continued

Ethyl 2,3-cis-diphenylcyclopropane carboxylate

A solution of tris(4-bromophenyl)aminium hexachloroantimonate (245 mg) in dichloromethane (10 mL) was cooled in an ice bath and purged with nitrogen for 1 h. To this was added a solution of cis-stilbene (180 mg) and ethyl diazoacetate (1.14 g) in dichloromethane (10 mL). The reaction mixture was stirred overnight and allowed to warm to ambient temperature. The reaction was quenched with saturated potassium carbonate solution in methanol (5 mL), diluted with water and extracted with ethyl acetate. The organic layer was separated, dried over magnesium sulfate and concentrated to give crude title compound (0.1 g) which was used without purification.

B.

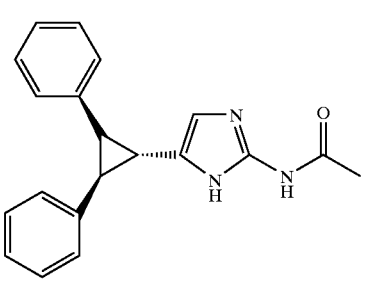

The ester from part A may be converted to the corresponding acid via saponification with KOH in a mixture of water and dioxane. The resulting acid may be converted to the title compound by using the procedure described in Example 13 parts B, C, D and E.

EXAMPLE 286

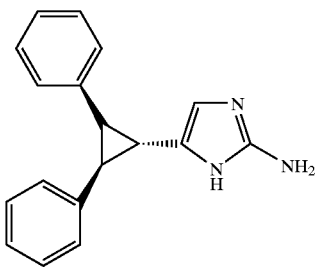

This compound may be prepared from the title compound Example 285 by using the procedure described in Example 14.

EXAMPLE 287

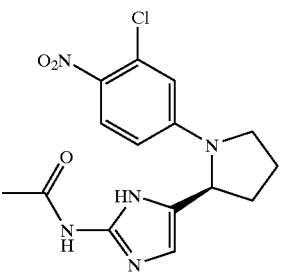

A.

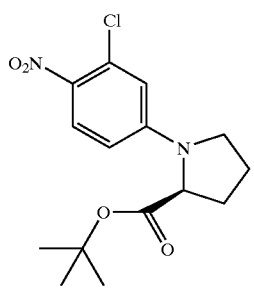

To a solution of L-proline tert-butyl ester

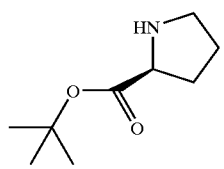

(1.06 g, 7.5 mmol) in dry DMSO (10 ml) were added 3-chloro-4-nitrofluorobenzene (1.48 g, 8.4 mmol) and diisopropylethylamine (2.60 mL, 15 mmol). The resulting solution was heated at 110° C. in a sealed tube for 48 hours. The reaction mixture was cooled to room temperature and partitioned between brine and ethyl acetate. The aqueous layer was extracted with ethyl acetate. The combined organic extracts were washed with water, dried over sodium sulfate, and concentrated in vacuo. Purification of the crude residue on silica gel (7:3/EtOAc-hexanes) provided 1.98 g (90%) of a pale yellow solid. $^1$H NMR (CD$_3$OD) δ 8.13 (1H, d, J=2.7 Hz), 8.02 (1H, dd, J=9.3 Hz, 2.7 Hz), 6.92 (1H, d, J=9.3 Hz), 5.01 (1H, dd, J=9.2 Hz, 3.9 Hz), 3.35 (1H, m), 3.30 (1H, m), 2.31 (1H, m), 2.07 (1H, m), 2.02 (2H, m), 1.38 (9H, s).

B.

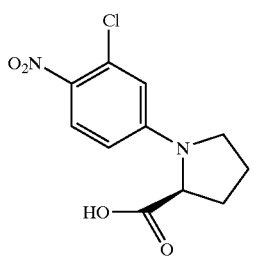

The Part A compound (0.44 g, 1.5 mmol) was dissolved in 1:1 CH$_2$Cl$_2$-trifluoroacetic acid (5 mL). The resulting solution was stirred at room temperature for 12 hours. The reaction mixture was concentrated in vacuo and azeotroped with toluene to afford 350 mg of the title compound as a brown solid. $^1$H NMR (CD$_3$OD) δ 8.26 (1H, d, J=2.7 Hz), 8.17 (1H, dd, J=9.3 Hz, 2.7 Hz), 7.19 (1H, d, J=9.3 Hz), 5.20 (1H, dd, J=9.2 Hz, 3.9 Hz), 3.94 (1H, m), 3.77 (1H, m), 2.64 (1H, m), 2.27 (1H, m), 2.19 (3H, m).

C.

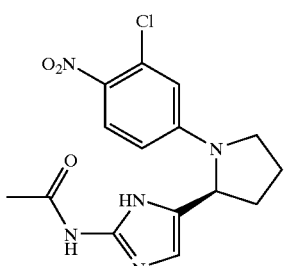

This compound may be prepared from the part B compound by using the procedure described in Example 13 parts B, C, D and E.

EXAMPLE 288

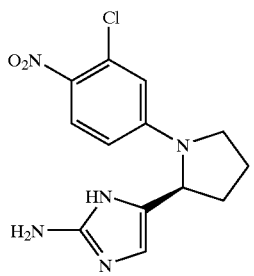

This compound may be prepared from the title compound Example 287 by using the procedure described in Example 14.

EXAMPLE 289

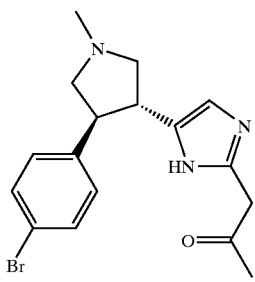

A.

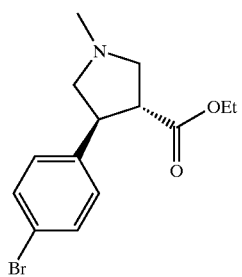

A mixture of ethyl 4-bromocinnamate (0.5 g, 2 mmol), sarcosine (0.19 g, 2.2 mmol), and paraformaldehyde (0.19 g, 6.4 mmol) in benzene (50 mL) was stirred for 10 hr at reflux with continuous removal of water. The mixture was cooled to ambient temperature and concentrated. The residue was chromatographed on silica gel (ethyl acetate) to give the desired product (0.21 g).

B.

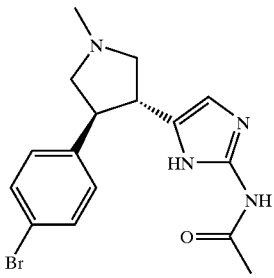

The ester from Part A may be converted to the corresponding acid via saponification with KOH in a mixture of water and dioxane. The resulting acid may be converted to the title compound by using the procedure described in Example 13 parts B, C, D and E.

EXAMPLE 290

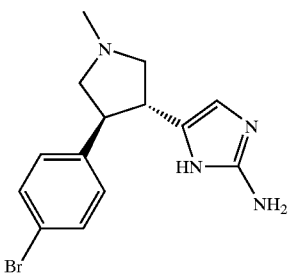

This compound may be prepared from the title compound Example 289 by using the procedure described for Example 14.

EXAMPLE 291

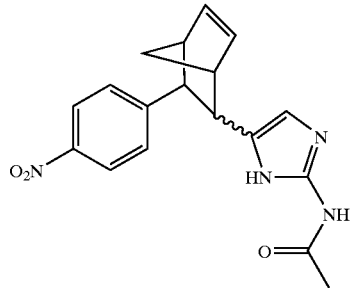

A.

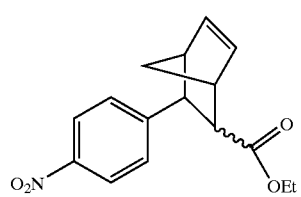

To a solution of ethyl 4-nitrocinnamate (0.5 g, 2.2 mmol) and cyclopentadiene (0.17 g, 2.7 mmol) in toluene (20 mL) was added 1M solution of diethylaluminum chloride (2.6 mL, 2.6 mmol) in hexane at −78° C. The resulting solution was stirred at −78° C. for 1.5 h and warmed to ambient temperature and stirred for 12 h. The solution was washed with 1N NaOH solution, dried ($MgSO_4$) and concentrated. The residue was chromatographed on silica gel (ethyl acetate:hexanes/1:4) to give the desired product (0.39 g) as a 4:1 mixture of 2 isomers.

B.

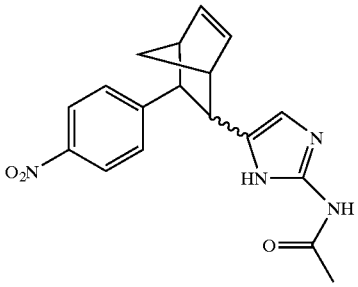

The ester from part A may be converted to the corresponding acid via saponification with KOH in a mixture of water and dioxane. The resulting acid may be converted to the title compound by using the procedure described in Example 13 parts B, C, D and E.

EXAMPLE 292

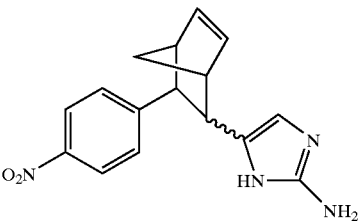

This compound may be prepared from the title compound of Example 291 by using the procedure described in Example 14.

The following Examples 293 to 304 compounds were prepared according to the procedure described above for Example 234.

| Example # | Structure | Characterization MS: (M + H)+ |
|---|---|---|
| 293 | 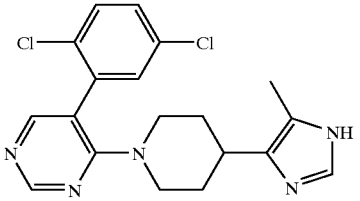 | 388 |
| 294 | 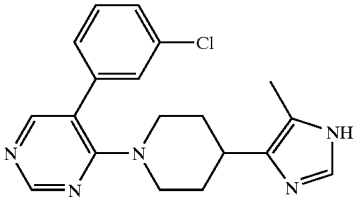 | 354 |
| 295 | 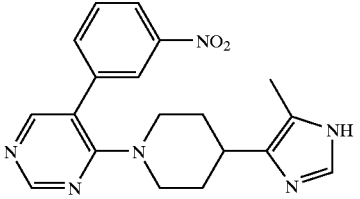 | 367 |
| 296 | 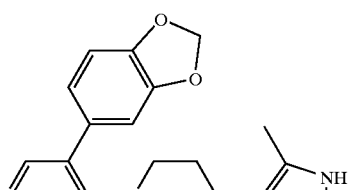 | 364 |
| 297 | 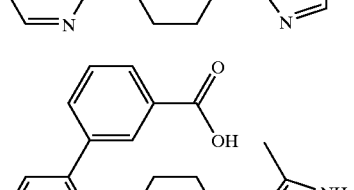 | 364 |
| 298 | 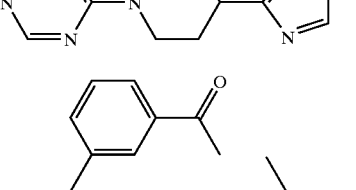 | 362 |
| 299 | 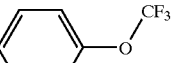 | 404 |
| 300 | 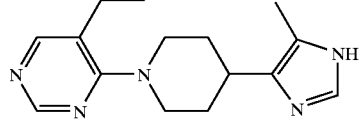 | 380 |
| 301 | 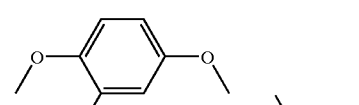 | 370 |
| 302 | 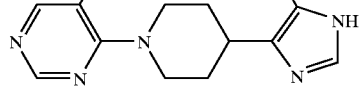 | 380 |
| 303 |  | 366 |
| 304 | 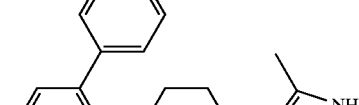 | 370 |

The following Examples 305 to 314 compounds were prepared according to the procedure described above for Example 252.

| Example # | Structure | Characterization MS: (M + H)+ |
|---|---|---|
| 305 | 2-Cl-phenyl variant | 384 |
| 306 | 3-Cl-phenyl variant | 384 |
| 307 | 4-Cl-phenyl variant | 384 |
| 308 | 3-CF₃-phenyl variant | 418 |
| 309 | 2,4-diCl-phenyl variant | 418 |
| 310 | 3,4-diCl-phenyl variant | 418 |
| 311 | 3-methyl-phenyl variant | 364 |
| 312 | 2,5-dimethyl-phenyl variant | 378 |
| 313 | 3-methyl-4-F-phenyl variant | 382 |
| 314 | 2-OMe-5-Cl-phenyl variant | 414 |

The following examples were prepared in a manner similar to that described for the preparation of Example 252.

| Example # | Structure | Characterization MS: (M + H)+ |
|---|---|---|
| 315 | 2-Cl-phenyl pyrimidine isopropoxy piperidine methylimidazole | 412 |
| 316 | 3-Cl-phenyl pyrimidine isopropoxy piperidine methylimidazole | 412 |
| 317 | 4-Cl-phenyl pyrimidine isopropoxy piperidine methylimidazole | 412 |
| 318 | 3-CF3-phenyl pyrimidine isopropoxy piperidine methylimidazole | 446 |
| 319 | 3-Cl-4-F-phenyl pyrimidine isopropoxy piperidine methylimidazole | 430 |
| 320 | 3,4-diCl-phenyl pyrimidine isopropoxy piperidine methylimidazole | 446 |
| 321 | 3-methylphenyl pyrimidine isopropoxy piperidine methylimidazole | 392 |
| 322 | 2,5-dimethylphenyl pyrimidine isopropoxy piperidine methylimidazole | 406 |
| 323 | 3-methyl-4-F-phenyl pyrimidine isopropoxy piperidine methylimidazole | 410 |

-continued
| Example # | Structure | Characterization MS: (M + H)+ |
|---|---|---|
| 324 | 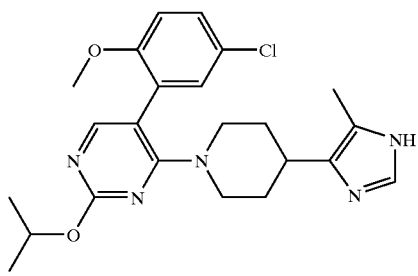 | 442 |
| 325 | 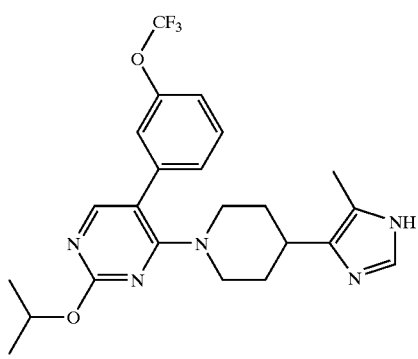 | 462 |
| 326 | 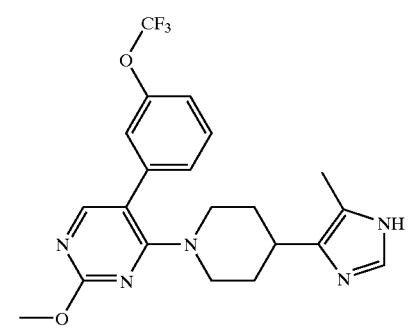 | 434 |
| 327 | 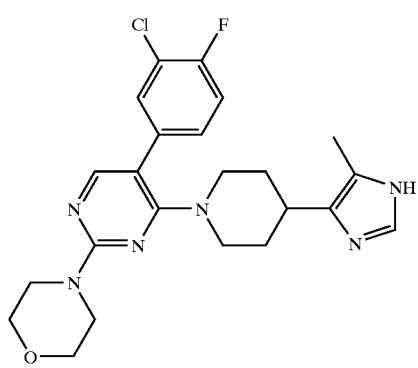 | 457 |
-continued
| Example # | Structure | Characterization MS: (M + H)+ |
|---|---|---|
| 328 | 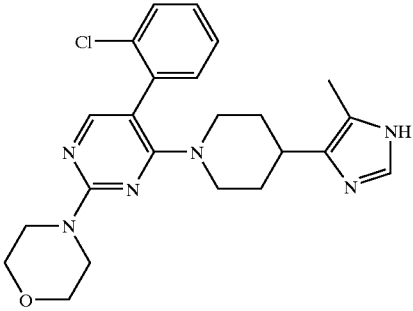 | 439 |
| 329 | 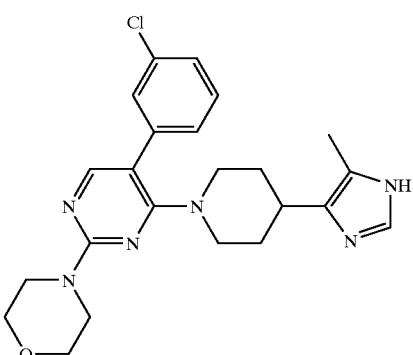 | 439 |
| 330 | 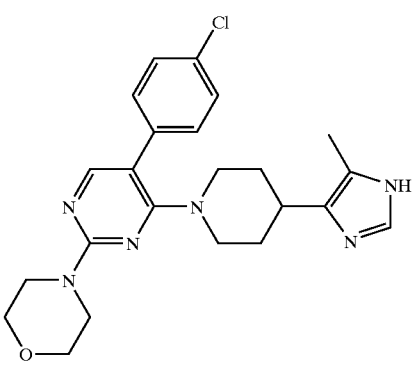 | 439 |
| 331 | 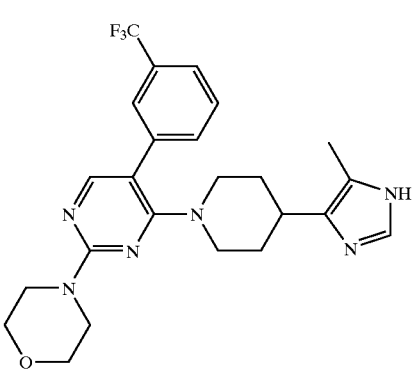 | 473 |

-continued

| Example # | Structure | Characterization MS: (M + H)+ |
|---|---|---|
| 332 | 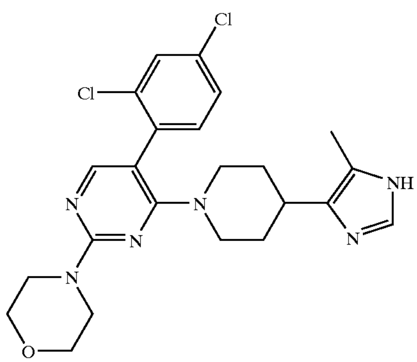 | 473 |
| 333 | 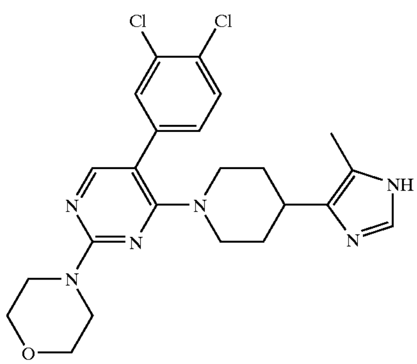 | 473 |
| 334 | 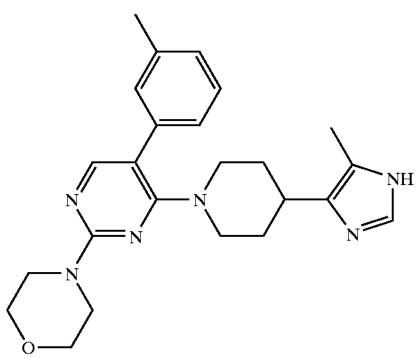 | 419 |
| 335 | 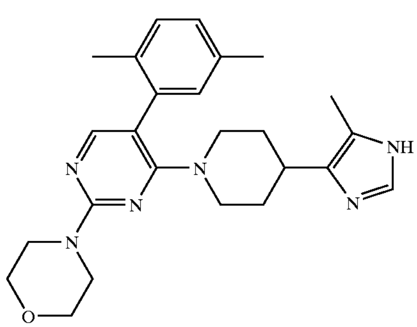 | 433 |

-continued

| Example # | Structure | Characterization MS: (M + H)+ |
|---|---|---|
| 336 | 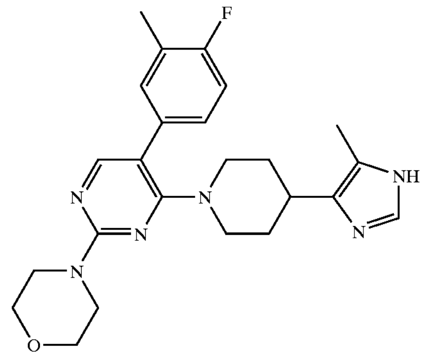 | 437 |
| 337 | 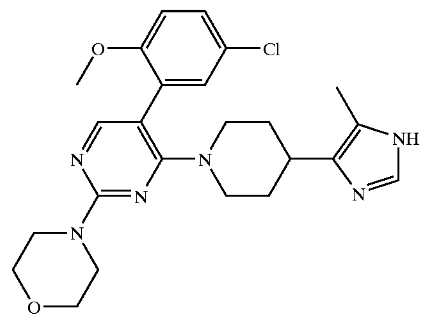 | 469 |
| 338 | 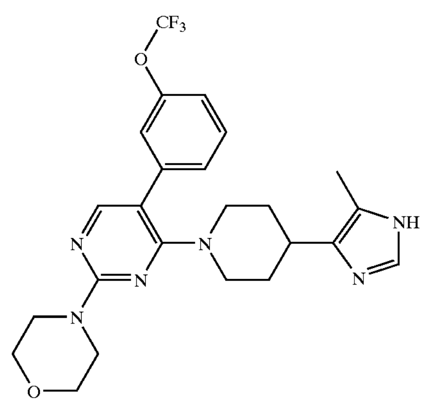 | 489 |

The following examples were prepared in a manner similar to that described for the preparation of Example 174.

| Example # | Structure | Characterization MS: (M + H)+ |
|---|---|---|
| 339 | 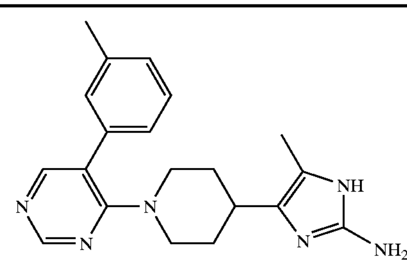 | 349 |

-continued

| | | | |
|---|---|---|---|
| 340 | (structure) | 363 | (structure) |
| 341 | (structure) | 367 | (structure) |
| 342 | (structure) | 403 | (structure) |
| 343 | (structure) | 399 | (structure) |
| 344 | (structure) | 417 | (structure) |

EXAMPLE 345

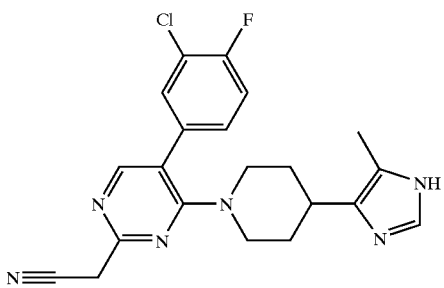

-continued

A.

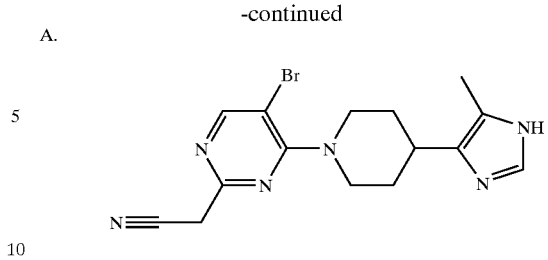

Sodium hydride (270 mg of 60%, 7 mmol) was added to a solution of tert-butyl cyanoacetate (850 mg, 6 mmol) in THF (20 mL). After stirring for 15 min., solid pyrimidine from example 252 part A (1.0 g, 2.8 mmol) was added and the solution was heated at 60° C. for 2 days. Additional tert-butyl cyanoacetate anion in THF (30 mL), prepared from 1.7 g (12 mmol) of tert-butyl cyanoacetate and 560 mg of 60% NaH (14 mmol), was added and the temperature was increased to 85° C. The solution was stirred at that temperature for an additional 24 h. The solution was neutralized to a pH of 7 and extracted with EtOAc. The combined EtOAc extracts were dried over $MgSO_4$ and concentrated. The crude residue obtained was dissolved in 30 mL of TFA and heated at 60° C. for 30 min. Concentration of the reaction mixture at reduced pressure followed by flash chromatography on silica gel (10/1/0.1 $CH_2Cl_2$/MeOH/$NH_4OH$) gave 200 mg of the title compound followed by 400 mg of the title compound of Example 346 part A.

B.

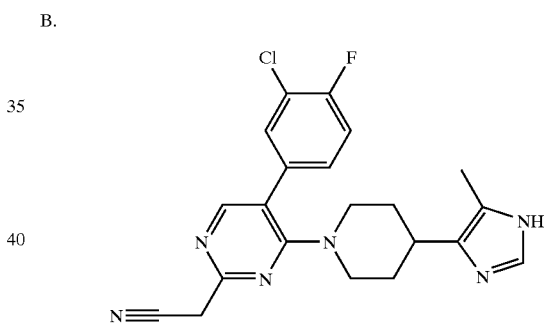

The title compound from part A above (180 mg) was coupled with 3-chloro-4-fluorophenyl boronic acid according to the procedure described for Example 234 to afford 66 mg of the title compound as a TFA salt after purification by preparative HPLC (conditions are as described for Example 1). MS: m/z 411 $(M+H)^+$.

EXAMPLE 346

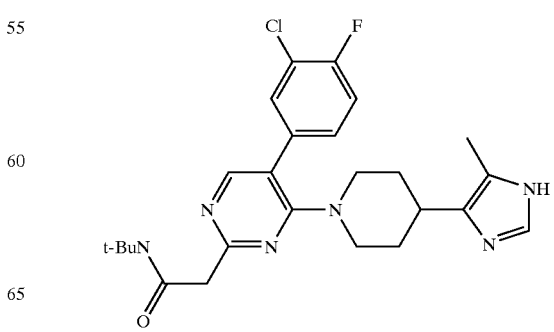

177

A.

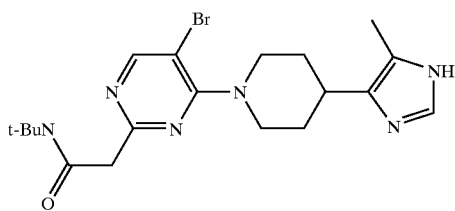

The title compound was obtained by the same procedure described above for Example 345 part A.

B.

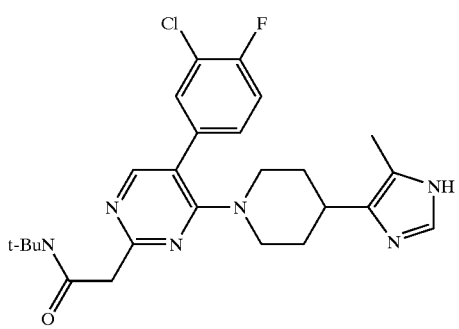

The title compound from part A above (400 mg) was coupled with 3-chloro-4-fluorophenyl boronic acid according to the procedure described for Example 234 to afford 287 mg of the title compound as a TFA salt after purification by preparative HPLC (conditions are as described for Example 1). MS: m/z 485 (M+H)$^+$.

EXAMPLE 347

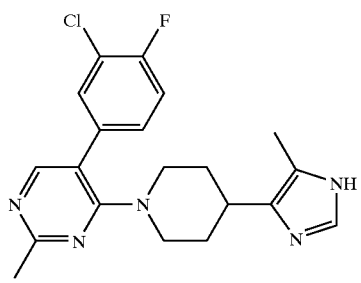

The title compound from Example 346 (35 mg) was treated with 5 ml of 6M HCl and the resulting solution was heated at reflux for 24 h. Concentration of the reaction mixture at reduced pressure followed by purification by preparative HPLC (conditions are as described for Example 1) afforded 25 mg of the title compound as a TFA salt. MS: m/z 386 (M+H)$^+$.

178

EXAMPLE 348

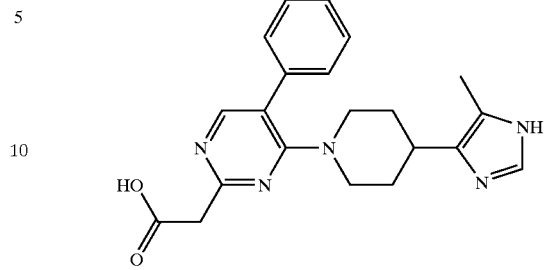

The title compound from Example 345 (15 mg) was treated with excess sodium hydroxide in aqueous MeOH. The resulting mixture was heated at reflux for 24 h. Purification of the reaction mixture by preparative HPLC, as described for Example 1, gave 7 mg of the title compound as a TFA salt. $^1$H NMR (400 MHz, CD$_3$OD) 8.72 (s, 1), 8.26 (s, 1), 8.21 (s, 1), 7.74 (d, 1, J=6.7), 7.48 (m, 2), 4.46 (br d, 2, J=13), 3.37 (s, 2), 3.16 (m, 3), 2.34 (s, 3), 1.85 (m, 4).

The following examples were prepared according to the procedure described above for Example 234.

| Example # | Structure | Characterization MS: (M + H)$^+$ |
|---|---|---|
| 349 | MeO-phenyl-pyridine-piperidine-methylimidazole | 349 |
| 350 | Cl-phenyl-pyridine-piperidine-methylimidazole | 353 |
| 351 | M-phenyl-pyridine-piperidine-methylimidazole | 333 |

-continued

| Example # | Structure | Characterization MS: (M + H)+ |
|---|---|---|
| 352 | 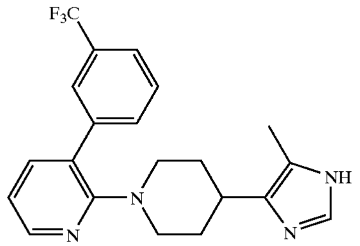 | 387 |
| 353 | 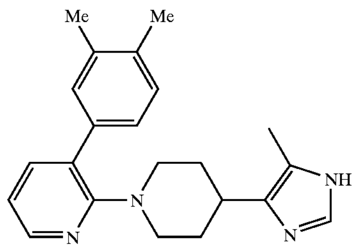 | 347 |
| 354 | 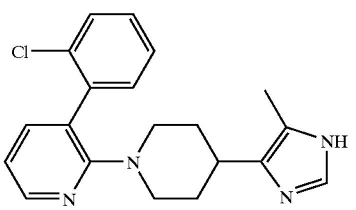 | 353 |
| 355 | 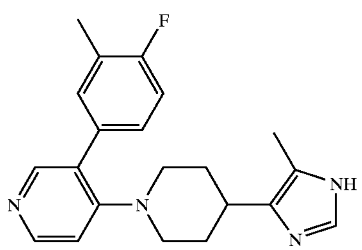 | 351 |
| 356 | 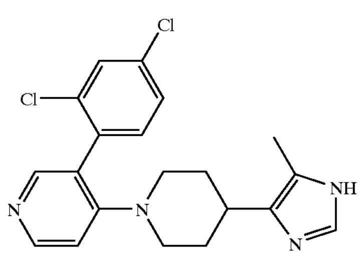 | 387 |

What is claimed is:
1. A compound having the structure

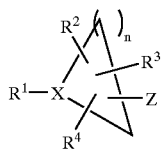

wherein
n is 4;
X is N;

Z is a 5- or 6-membered nitrogen-containing monocyclic heteroaryl group which is selected from the group consisting of imidazole attached at its 4- or 5-position to the ring, aminoimidazole, alkylimidazole, alkylthioimidazole, alkylthio(amino)imidazole, amino-(alkyl)imidazole, (alkanoylamino)imidazole, aminothiazole, aminooxazole, aminooxadiazole, dialkylimidazole, alkyl(alkanoylamino)imidazole, alkyl(amino)imidazole, arylaminocarbonylamino(alkyl)imidazole, alkoxycarbonylamino(alkyl)imidazole, alkylcarbonylamino(alkyl)imidazole, aminotriazole or diaminopyrimidine;

$R^1$ is heteroaryl;

and $R^1$ may be unsubstituted or substituted with from one to five substituents;

and wherein the $R^1$ heteroaryl group is selected from

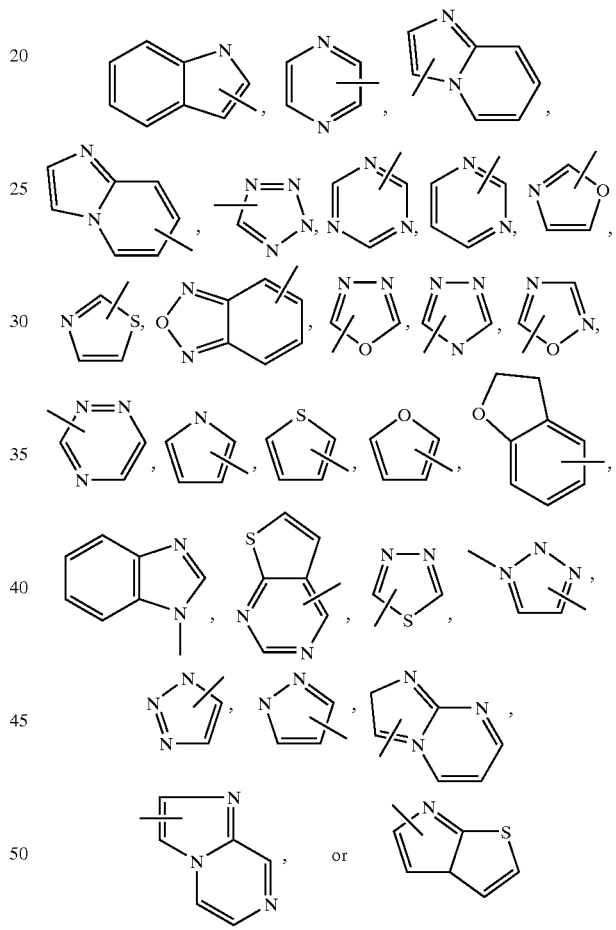

$R^2$, $R^3$ and $R^4$ are the same or different and are independently H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, amino, alkylamino, dialkylamino, alkenylamino, alkynylamino, arylalkylamino, aryl, arylalkyl, arylamino, aryloxy, cycloheteroalkyl, cycloheteroalkylalkyl, heteroaryl, heteroarylamino, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl, polyhaloalkoxy, aminothio, aminosulfinyl, aminosulfonyl, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, acyl, carboxy, aminocarbonyl, alkylcarbonyl, alkoxycarbonyl, alkylcarbonyloxy, alkylcarbonylamino, arylcarbonyl, arylcarbonyloxy, arylcarbonylamino, heteroarylcarbonyl, heteroarylcarbonyloxy, heteroarylcarbonylamino, cyano, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, alkoxycarbonylamino, 1,1-(alkoxyl or aryloxy)$_2$alkyl (where the two aryl or alkyl substituents can be independently defined, or linked to one another to form a ring), S(O)$_2$R$^6$R$^7$, —NR$^6$(C=NR$^7$)alkyl, —NR$^6$(C=NR$^7$)alkenyl, —NR$^6$(C=NR$^7$)alkynyl, —NR$^6$(C=NR$^7$)heteroaryl, —NR$^8$(C=NCN)-amino,

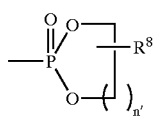

pyridine-N-oxide,

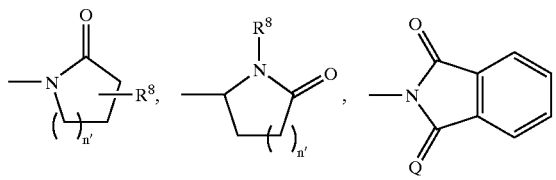

(where Q is O or H$_2$ and n' is 0, 1, 2 or 3) or

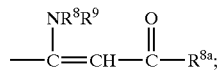

tetrazolyl, pyrazolyl, pyridyl, thiazolyl, pyrimidinyl, imidazole, oxazole, or triazole, —PO(R$^{13}$)(R$^{14}$), (where R$^{13}$ and R$^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); and may be optionally independently substituted with from one to five substituents, which may be the same or different;

R$^6$, R$^7$, R$^8$, R$^{8a}$ and R$^9$ are the same or different and are independently hydrogen, alkyl, haloalkyl, aryl, heteroaryl, arylalkyl, cycloalkyl, (cycloalkyl)alkyl, or cycloheteroalkyl;

or a pharmaceutically acceptable salt thereof, or a prodrug thereof, and all stereoisomers thereof.

2. The compound as defined in claim 1 wherein the R$^1$ group may be substituted within from one to five of the following groups:

alkyl, alkenyl, alkynyl, alkoxy, alkenyloxy, alkynyloxy, (alkyl or aryl)$_3$Si (where each alkyl or aryl group is independent), cycloalkyl, cycloalkenyl, amino, alkylamino, dialkylamino, alkenylamino, alkynylamino, arylalkylamino, aryl, arylalkyl, arylamino, aryloxy, cycloheteroalkyl, cycloheteroalkylalkyl, heteroaryl, heteroarylamino, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl, CF$_3$ and CF$_3$CH$_2$, polyhaloalkyloxy, CF$_3$O and CF$_3$CH$_2$O, aminothio, aminosulfinyl, aminosulfonyl, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, acyl, carboxy, aminocarbonyl, alkylcarbonyl, alkoxycarbonyl, alkylcarbonyloxy, alkylcarbonylamino, arylcarbonyl, arylcarbonyloxy, arylcarbonylamino, heteroarylcarbonyl, heteroarylcarbonyloxy, heteroarylcarbonylamino, cyano, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, 1,1-(alkoxyl or aryloxy)$_2$alkyl (where the two aryl or alkyl substituents can be independently defined, or linked to one another to form a ring, 1,3-dioxane or 1,3-dioxolane), S(O)$_2$R$^6$R$^7$, —NR$^6$(C=NR$^7$)alkyl, NR$^6$(C=NR$^7$)alkenyl, —NR$^6$(C=NR$^7$)alkynyl,

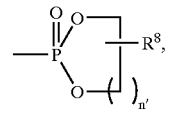

NR$^6$(C=NR$^7$)heteroaryl, —NR$^8$(C=NCN)-amino, pyridine-N-oxide,

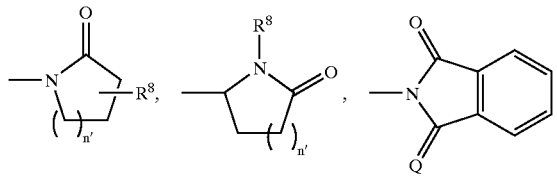

(where Q is O or H$_2$ and n' is 0,1, 2 or 3) or

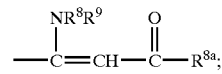

tetrazolyl, pyrazolyl, pyrydyl, thiazolyl, pyrimidinyl, imidazole, oxazole or triazole; —PO(R$^{13}$)(R$^{14}$), (where R$^{13}$ and R$^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy);

R$^6$, R$^7$, R$^8$, R$^{8a}$ and R$^9$ are independently hydrogen, alkyl, haloalkyl, aryl, heteroaryl, arylalkyl, cycloalkyl, (cycloalkyl)alkyl or cycloheteroalkyl, which substituents may be the same or different from each other and may be the same or different from the base $R^1$ group.

3. The compound as defined in claim 1 wherein $R^1$ is substituted with one to five of the following substituents: alkyl, alkylaminocarbonyl, arylaminocarbonyl, heteroarylaminocarbonyl, alkylcarbonylamino, heteroaryl, halo, aryl, cycloalkylcarbonylamino, arylcarbonylamino, heteroarylcarbonylamino, alkoxycarbonylamino, guanidinyl, nitro, cycloheteroalkyl, aryloxycarbonylamino, heteroaryloxyl carbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

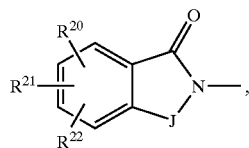

Where

J is: $CHR^{23}$,

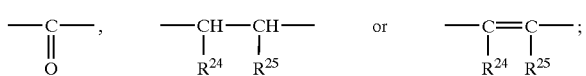

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to $R^1$, or attached via an alkylene chain at an open position, which substituents may be the same or different from each other and may be the same or different from the base $R^1$ group.

4. The compound as defined in claim 1 wherein Z is imidazole attached at its 4- or 5-position to the ring, aminoimidazole, alkylimidazole, alkylthioimidazole, alkylthio(amino)imidazole, amino(alkyl)imidazole or (acetylamino)imidazole.

5. The compound as defined in claim 1 wherein the moiety

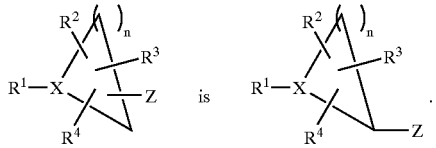

6. The compound as defined in claim 1 wherein $R^2$ and $R^3$ are independently H, lower alkyl, lower alkoxy or aryl, and $R^4$ and $R^5$ are each hydrogen.

7. The compound as defined in claim 1 wherein n is 4, $R^2$ and $R^3$ are independently H or lower alkyl, and $R^4$ and $R^5$ are each H, and $R^1$ is aryl or heteroaryl.

8. The compound as defined in claim 1 wherein $R^1$ is

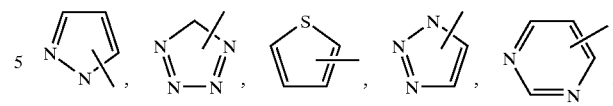

9. The compound as defined in claim 1 wherein $R^1$, $R^2$, $R^3$ and/or $R^4$ may be joined together with the N atom and/or carbons to which they are attached to form a non-aromatic ring.

10. The compound as defined in claim 1 having the structure

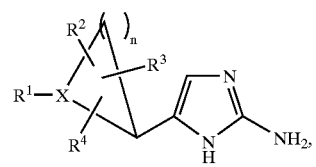

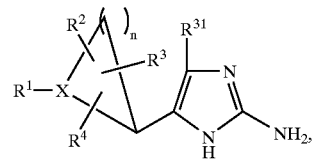

($R^{31}$ = alkyl, haloalkyl, aryl, heteroaryl)

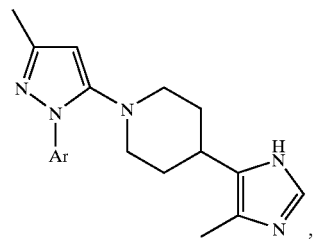

(Ar = aryl or heteroaryl)

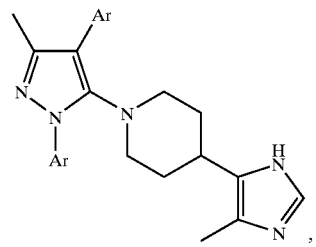

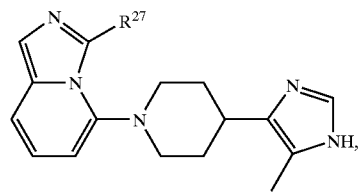

($R^{27}$ = alkyl or aryl)

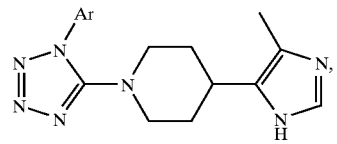

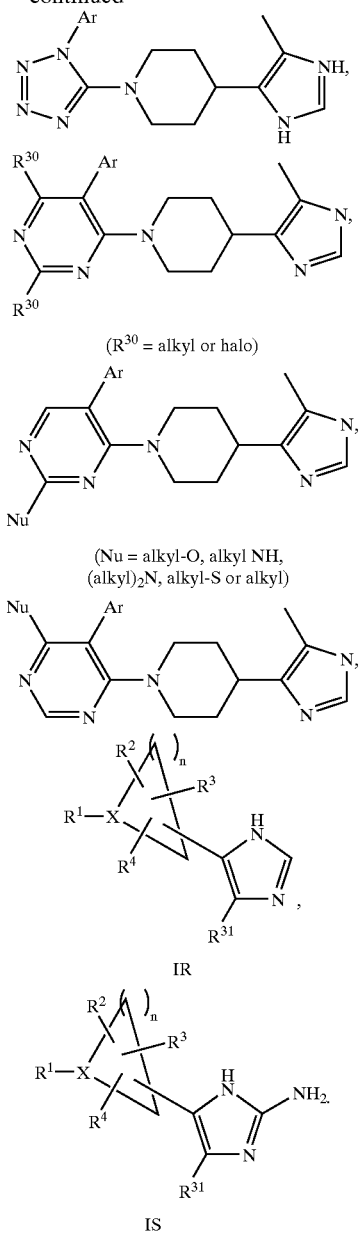

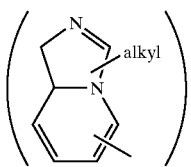

dialkylphenyl(alkoxy)pyrimidine, alkyl(halo)phenyl (alkoxy)pyrimidine, alkoxy(halo)phenyl(alkoxy) pyrimidine, dihalophenyl(dialkylamino)pyrimidine, heteroaryl(dihalophenyl)pyrimidine, halophenylpyrimidine, alkoxy(phenyl)pyrimidine, haloalkoxyphenylpyrimidine, phenoxy(phenyl)pyrimidine, heteroaryl(phenyl)pyrimidine, dialkoxyphenylpyrimidine, dialkylphenylpyrimidine, cycloheteroalkyl(phenyl)pyrimidine, alkoxy(halo)phenylpyrimidine, cycloheteroalkyl(dihalophenyl)pyrimidine, halophenyl(alkoxy)pyrimidine, alkyl(halo)phenylpyrimidine, nitrophenylpyrimidine, dihalophenyl(alkoxy)pyrimidine, carboxyphenylpyrimidine, alkylcarbonylphenylpyrimidine, naphthylpyrimidine, alkylthiophenylpyrimidine, alkyl(halophenyl)triazole, alkyl(halo)phenyl-(alkyl)-triazole, alkylimidazopyridine phenylimidazopyridine, halophenylimidazopyridine, dihalophenylimidazopyridine, alkoxyphenylimidazopyridine.

12. The compound as defined in claim 1 wherein
$R^2$ is $CH_3$ or H;
$R^3$ is $CH_3$ or H;
$R^4$ is H;
$R^1$ is 2,3-dihydrobenzofuran-4-yl, 1-phenyltetrazol-5-yl, 1-(2,4-dichloro-5-methoxyphenyl)tetrazol-5-yl, 1-(3-chlorophenyl)tetrazol-5-yl, 1-(3-chloro-4-methyl)tetrazol-5-yl, 1-(3-methylphenyl)tetrazol-5-yl, 1-(2-chlorophenyl)tetrazol-5-yl, 1-(2-methoxy-5-chloro)tetrazol-5-yl, 1-(3-methyl-4-chlorophenyl)tetrazol-5-yl, 1-(2-methoxy-5-chlorophenyl)tetrazol-5-yl, 1-(3-methoxyphenyl)tetrazol-5-yl, 1-(2-methoxy-5-chlorophenyl)tetrazol-5-yl, 1-(3-chlorophenyl)-3-methylpyrazol-5-yl, 1-(3-fluorophenyl)-3-methylpyrazol-5-yl, 1-(3-methoxyphenyl)-3-methylpyrazol-5-yl, 1-(3,5-dichlorophenyl)-3-methylpyrazol-5-yl, 1-(3-chlorophenyl)-3-ethylpyrazol-5-yl, 1-(3-chloro-4-methylphenyl)-3-methylpyrazol-5-yl, 1-(2,4-dimethylphenyl)-3-methylpyrazol-5-yl, 1-(3-chloro-4-fluorophenyl)-3-methylpyrazol-5-yl, 1-(3-trifluoromethylphenyl)-3-methylpyrazol-5-yl, 1-(3-chlorophenyl)-3-trifluoromethylpyrazol-5-yl, 1-(3-methylphenyl)3-methylpyrazol-5-yl, 1-(3-chlorophenyl)-3-ethylpyrazol-5-yl, 5-(3-chloro-4-fluorophenyl)pyrimidin-4-yl, 5-(2-chlorophenyl)pyrimidin-4-yl, 5-(3-methylphenyl)pyrimidin-4-yl, 5-(3-trifluoromethylphenyl)pyrimidin-4-yl, 5-(2,4-dichlorophenyl)pyrimidin-4-yl, 5-(2,5-dimethylphenyl)pyrimidin-4-yl, 5-(3,4-dichlorophenyl)pyrimidin-4-yl, 5-(2,3-dimethylphenyl)pyrimidin-4-yl, 5-(2-methoxy-5-chlorophenyl)pyrimidin-4-yl, 5-(2-methoxy-5-fluorophenyl)pyrimidin-4-yl, 5-(3-methyl-4-fluorophenyl)pyrimidin-4-yl, 5-(3-chloro-4-fluorophenyl)-2-methoxy-pyrimidin-4-yl, 5-(3-chloro-4-fluorophenyl)-2-dimethylamino-pyrimidin-4-yl, 5-(3-chloro-4-fluorophenyl)-2-morpholinyl-pyrimidin-4-yl, 1-(3-chlorophenyl)-3-methyltriazol-5-yl, 1-(3-chloro-4-methylphenyl)-3-methyltriazol-5-yl, 5-(2,5-

11. The compound as defined in claim 1 wherein $R^1$ is phenyltetrazole, 1-(2,4-dihalo-5-alkoxyphenyltetrazol-5-yl, alkylphenyltetrazole, halophenyltetrazol, 1-(2-alkoxy-5-halophenyl)tetrazol-5-yl, 1-(3-alkyl-4-halophenyl)tetrazol-5-yl, alkoxyphenyltetrazole, alkyl(halo)phenyltetrazole, alkoxy(halo)phenyltetrazole, alkoxy(alkyl)(halo)phenyltetrazole, phenyl-alkyl-pyrazole, alkoxyphenyl-alkyl-pyrazole, halophenyl-alkyl-pyrazole, alkyl(halo)phenyl-alkyl-pyrazole, alkylphenyl-alkyl-pyrazole, alkoxy(halo)phenyl-alkyl-pyrazole, alkoxy(alkyl)phenyl-alkyl-pyrazole, dihalophenyl-alkyl-pyrazole, dialkylphenyl-alkyl-pyrazole, alkoxyphenyl-alkyl-pyrazole, halophenyl-haloalkyl-pyrazole, alkoxyphenyl(alkyl)(halo)pyrazole, phenylpyrimidine, phenyl(halo)pyrimidine, diphenylpyrimidine, halophenyl(halo)pyrimidine, dihalopyrimidine, diphenyl(halo)pyrimidine, halo(phenyl)pyrimidine, dialkyl(halo)pyrimidine, dihalophenylpyrimidine, alkylphenylpyrimidine, alkoxyphenylpyrimidine, alkylphenyl(alkoxy)pyrimidie, dichlorophenyl)pyrimidin-4-yl, 5-(3-chlorophenyl)pyrimidin-4-yl, 5-(3-trifluoromethoxyphenyl)pyrimidin-4-yl, 5-(2-chlorophenyl)-2-methoxypyrimidin-4-yl, 5-(3-chlorophenyl)-2-methoxypyrimidin-4-yl, 5-(3-trifluoromethylphenyl)-2-methoxypyrimidin-4-yl, 5-(2,4-dichlorophenyl)-2-methoxypyrimidin-4-yl, 5-(3-methylphenyl)-2-methoxypyrimidin-4-yl, 5-(2,5-dimethylphenyl)-2-methoxypyrimidin-4-yl, or 5(3-methyl-4-fluorophenyl)-2-methoxypyrimidin-4-yl;

Z is 2-amino-5-methyl-imidazol-4-yl, 2,5-dimethylimidazol-4-yl, 2-amino-5-ethyl-imidazol-4-yl, 2-amino-5-isopropyl-imidazol-4-yl, 2-aminocarbonylamino-5-methyl-imidazol-4-yl, 5-methyl-imidazol-4-yl, imidazol-4-yl, or 4-methylimidazol-5-yl.

13. A compound having the structure

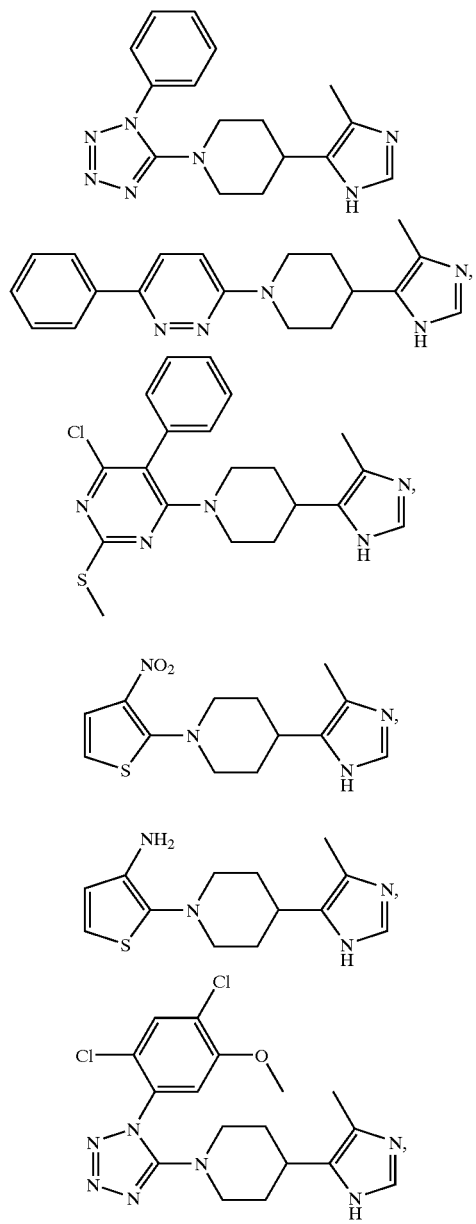
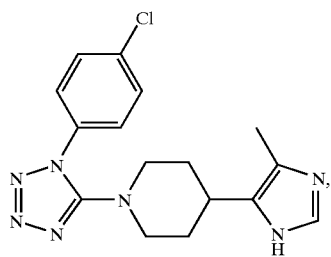
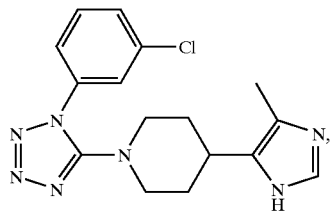
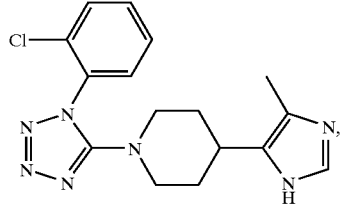
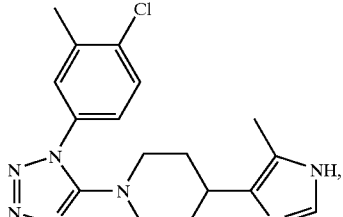
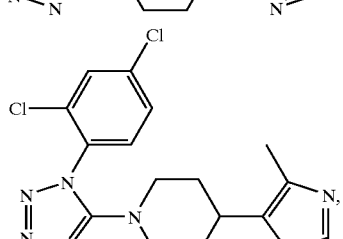
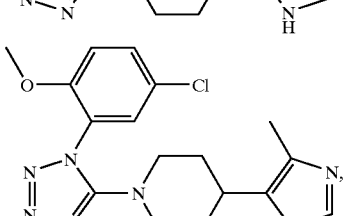
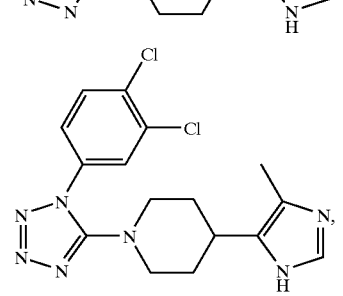

-continued
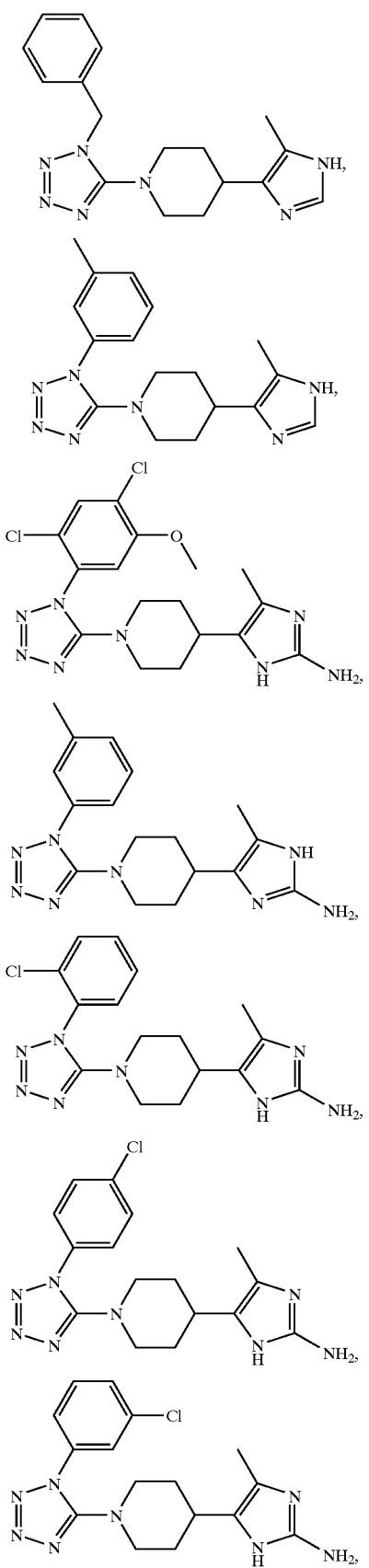
-continued
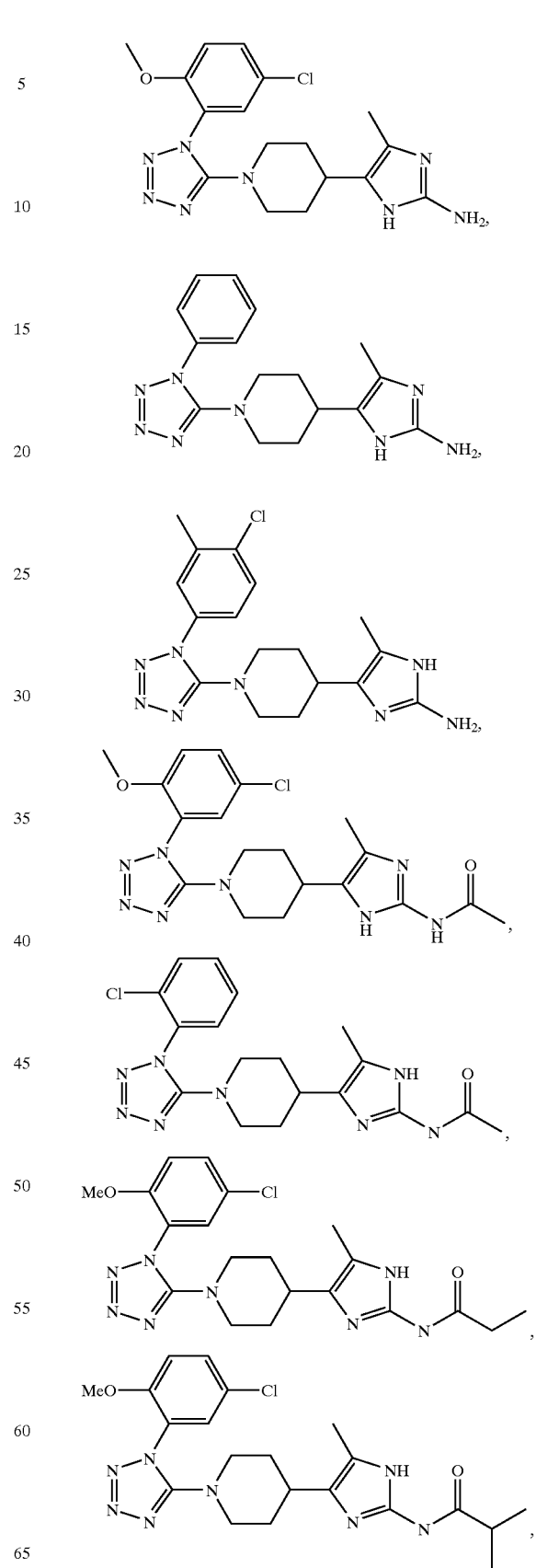

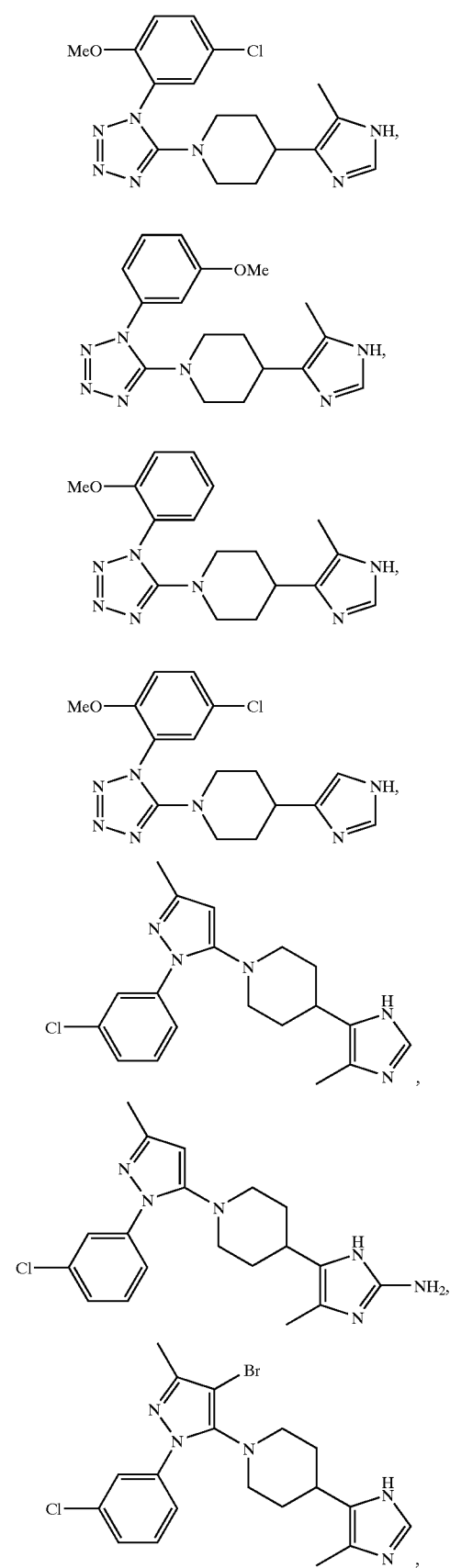
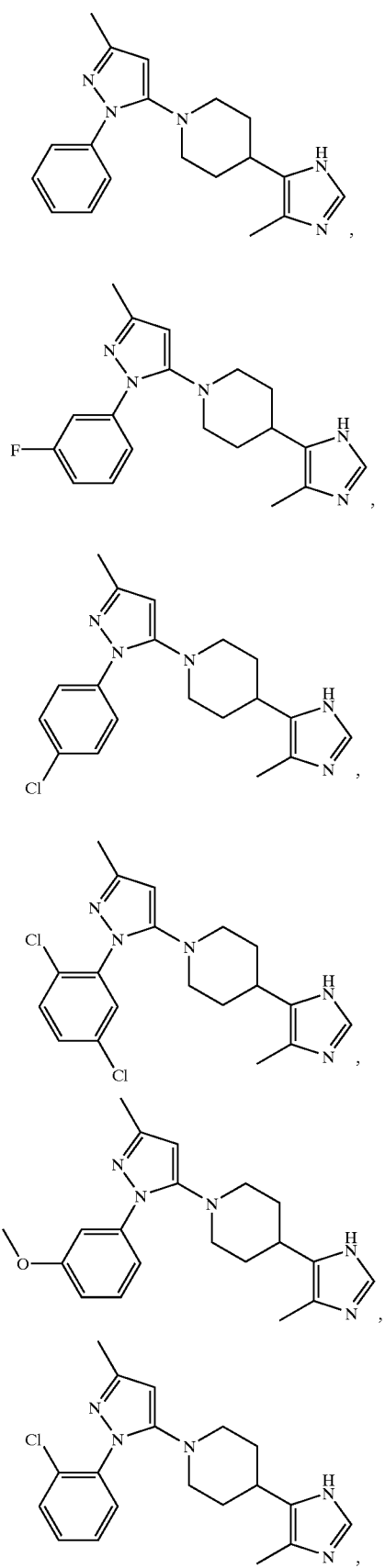

-continued
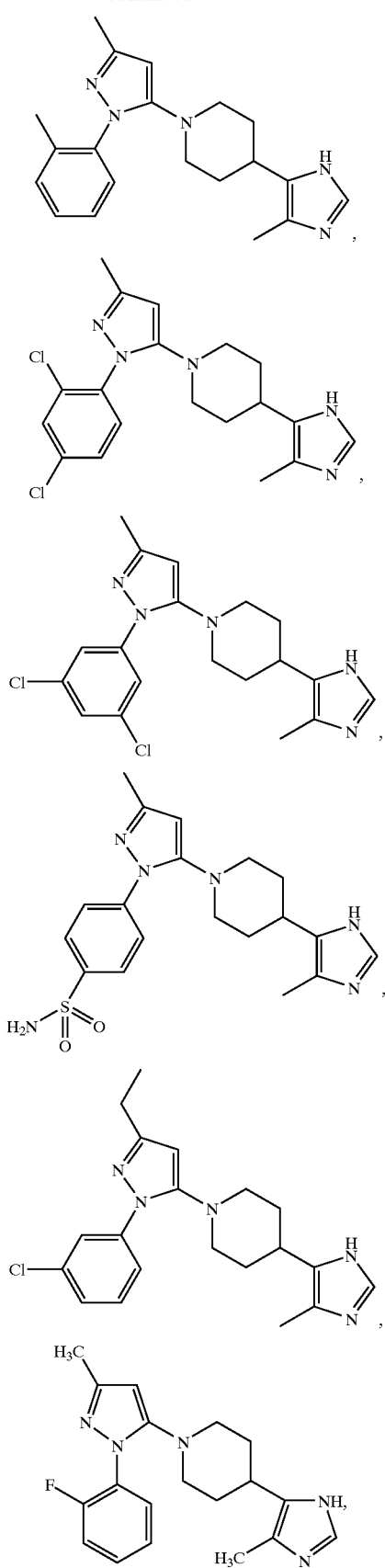
-continued
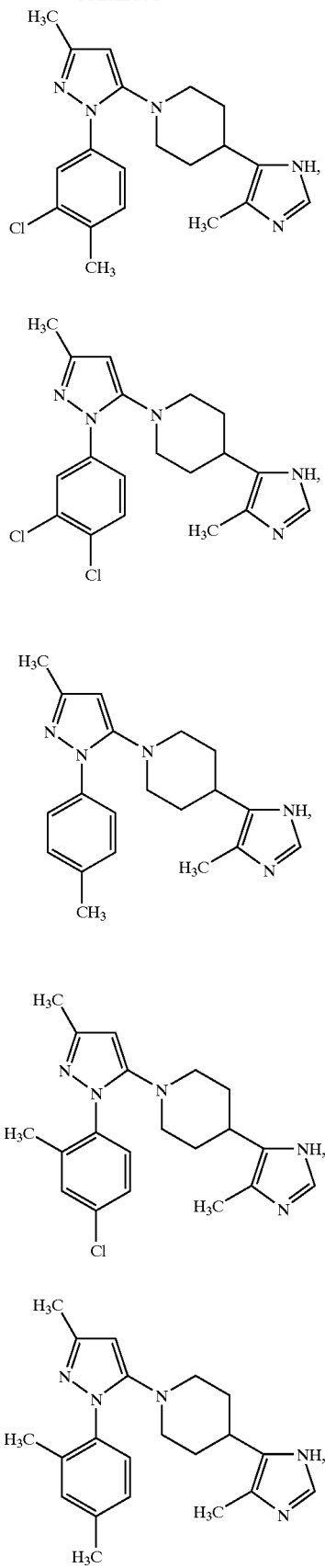

-continued
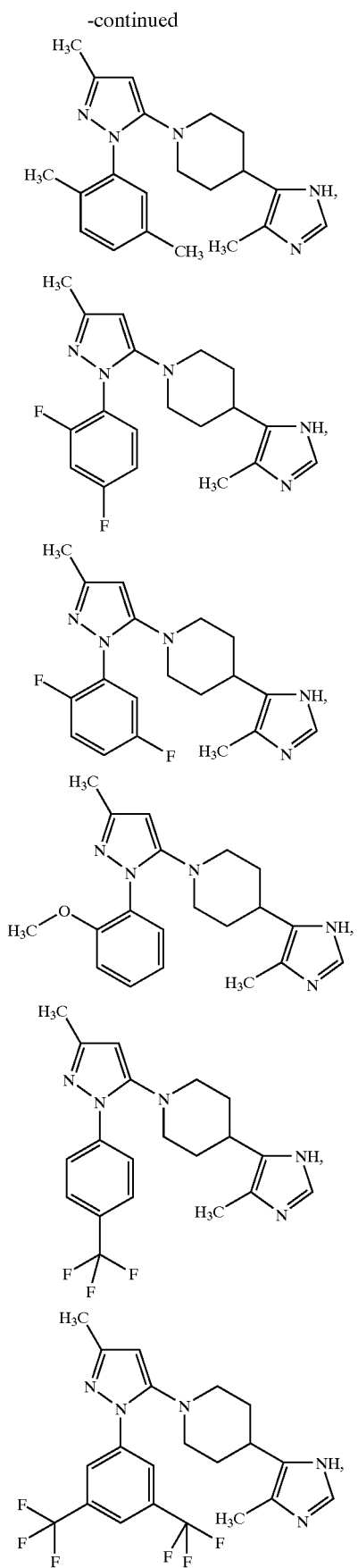
-continued
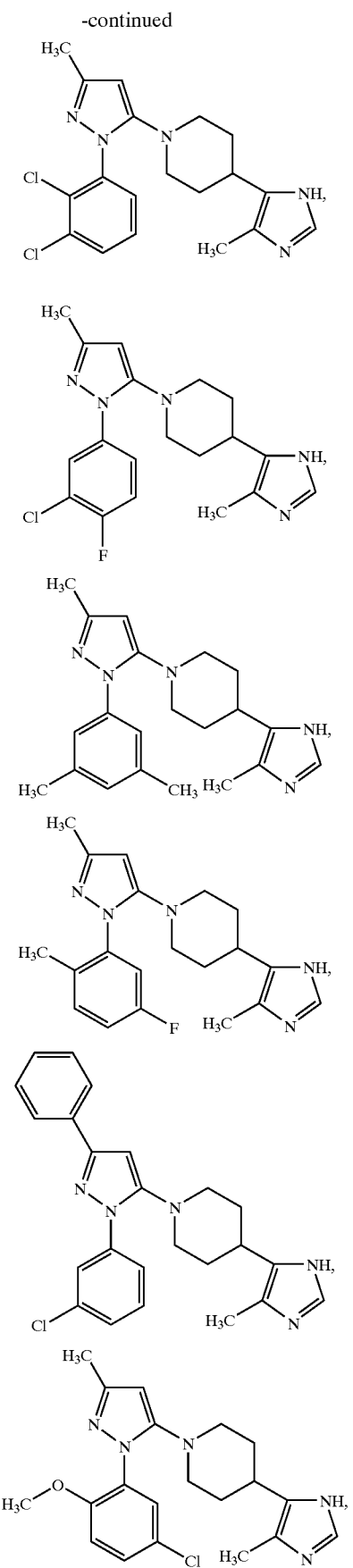

-continued
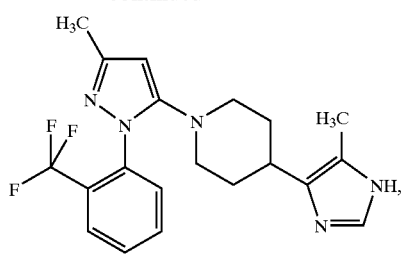
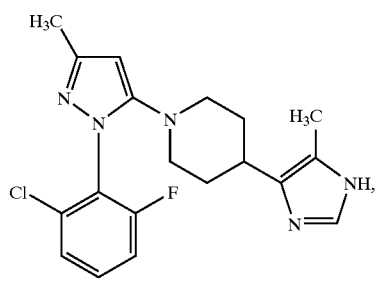
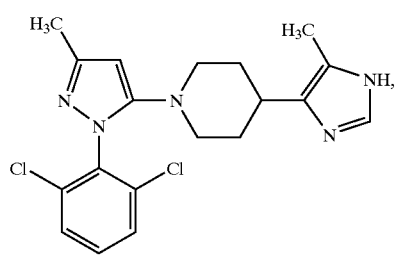
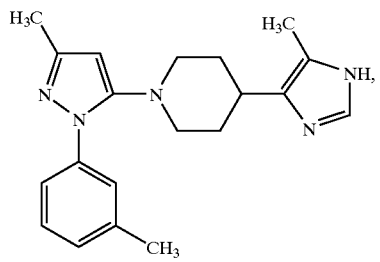
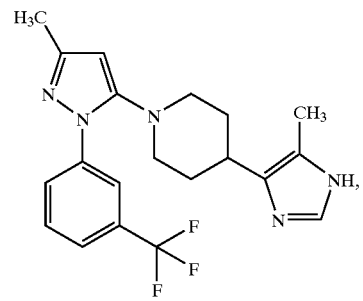
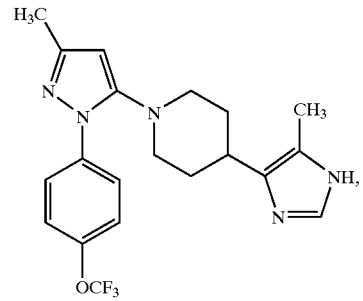
-continued
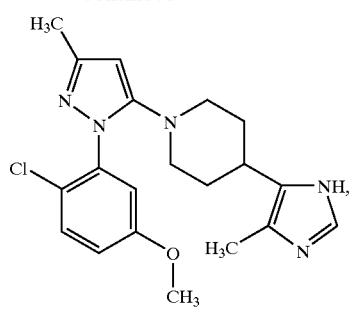
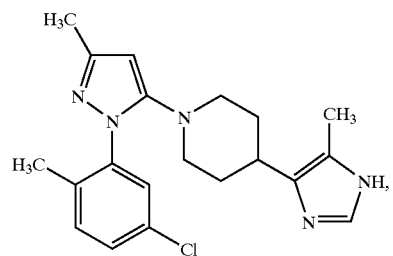
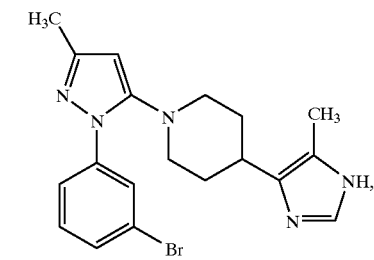
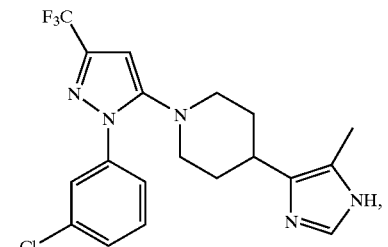
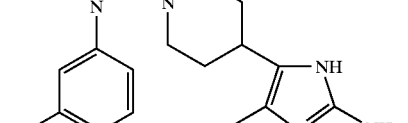
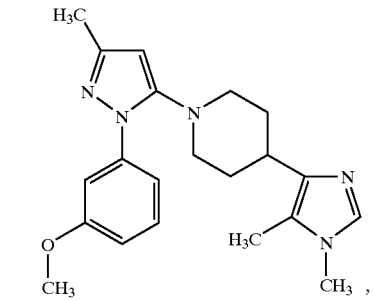

199
-continued
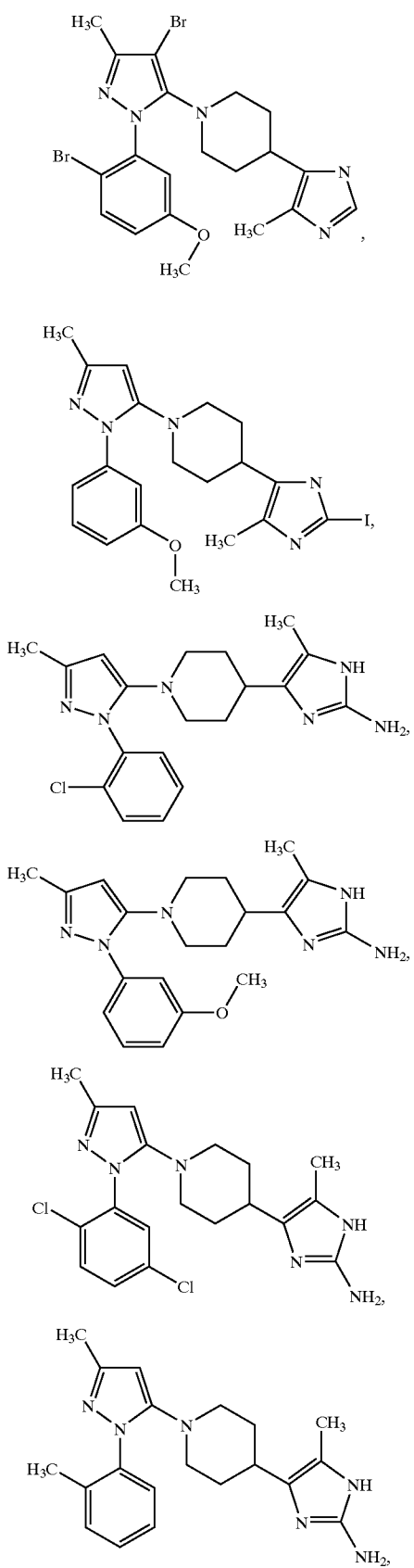
200
-continued
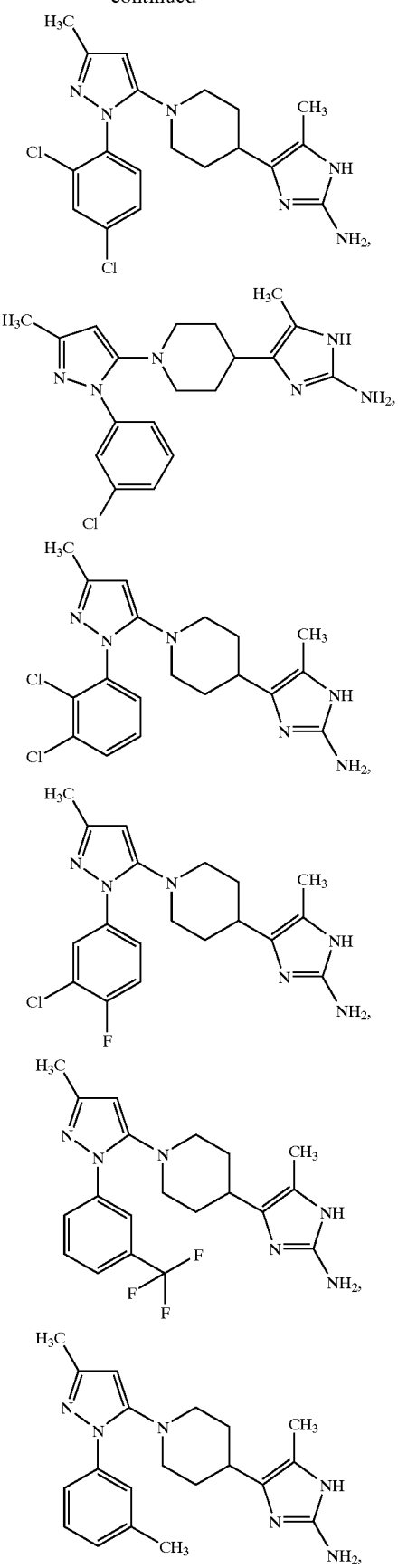

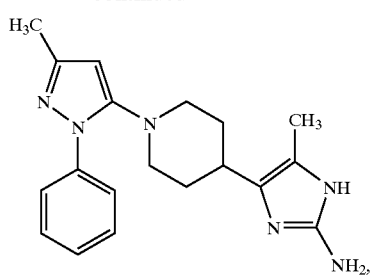
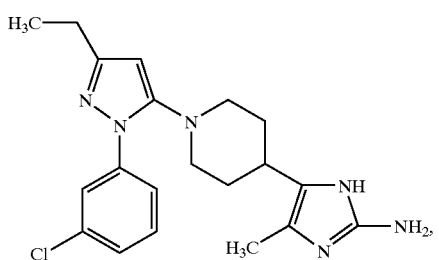
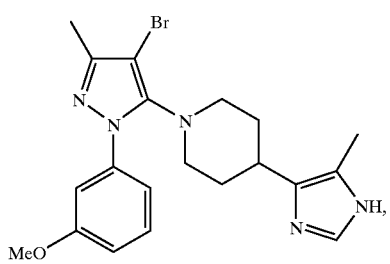
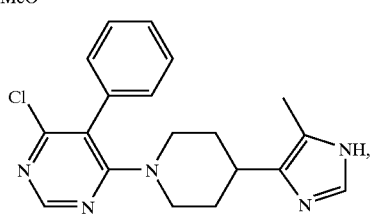
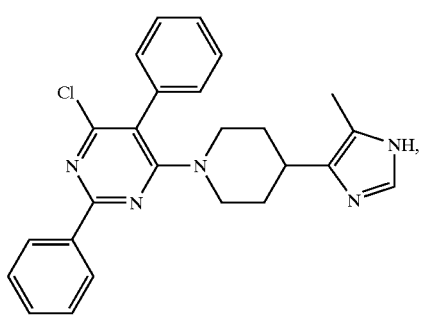
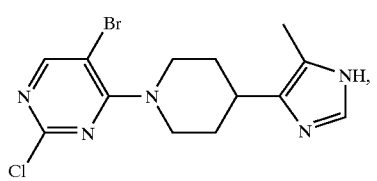
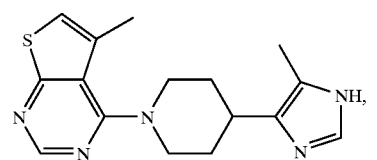
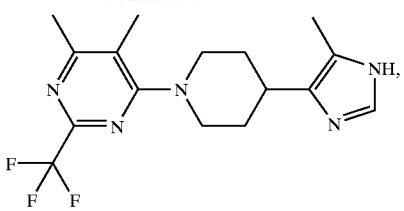
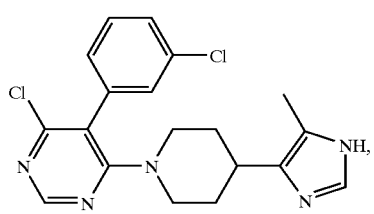
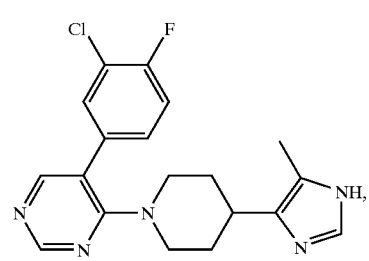
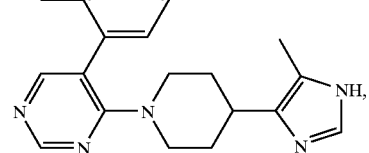
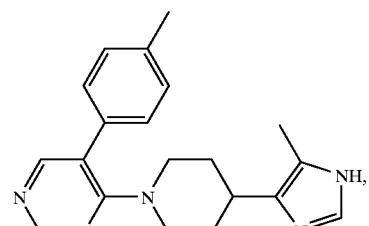
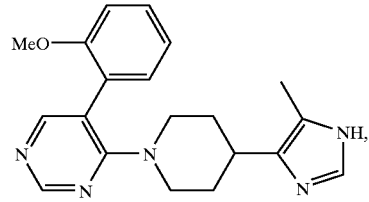
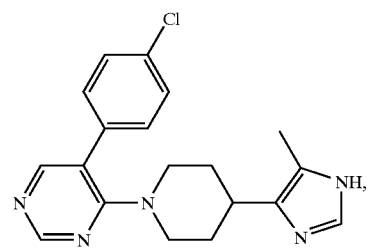

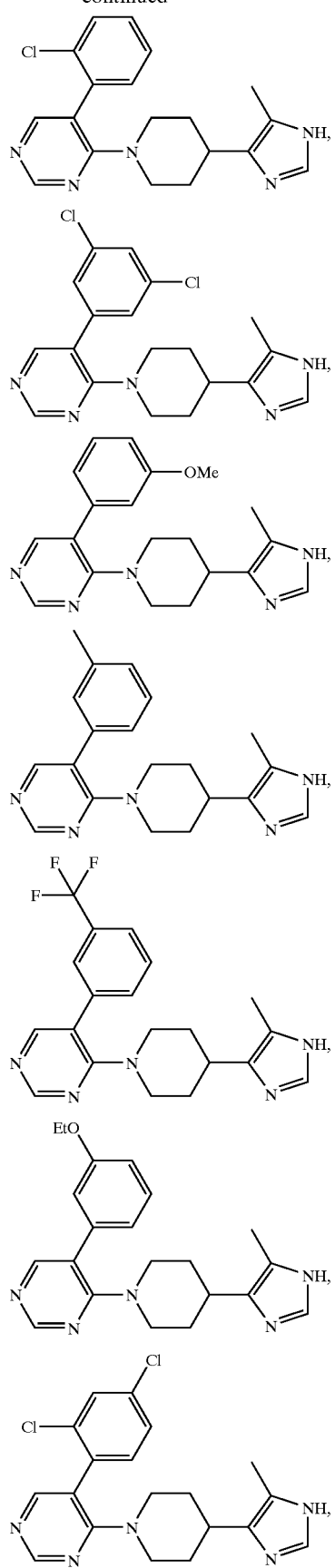
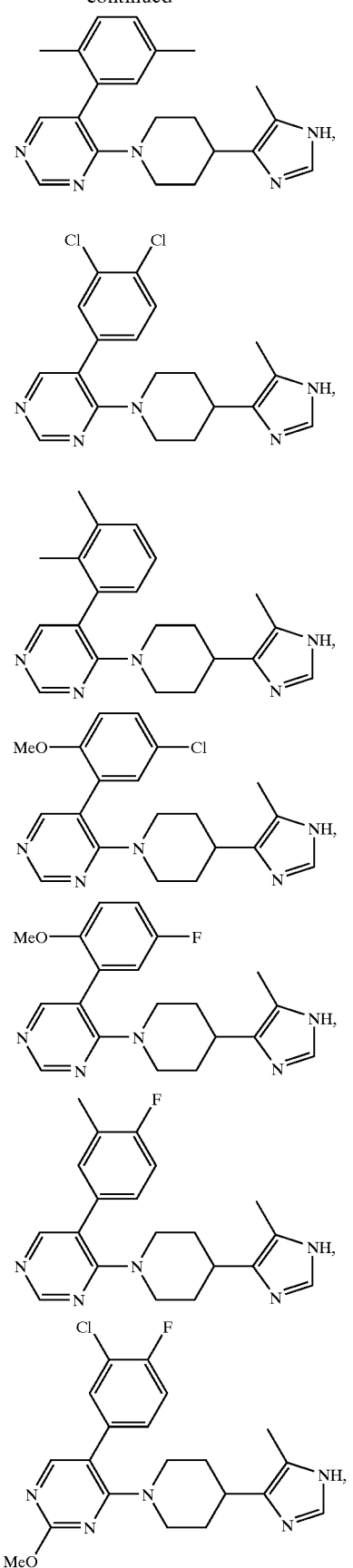

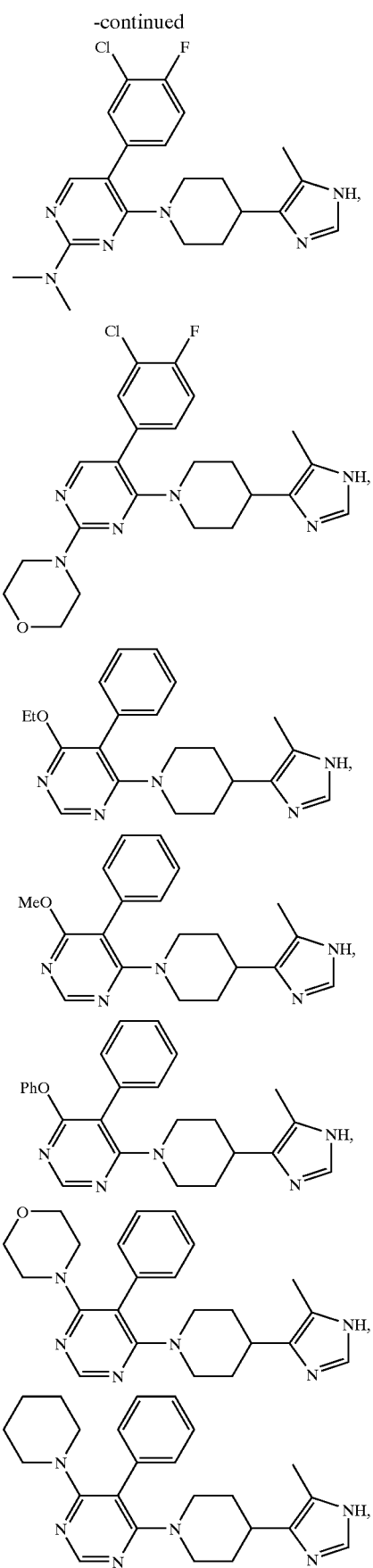
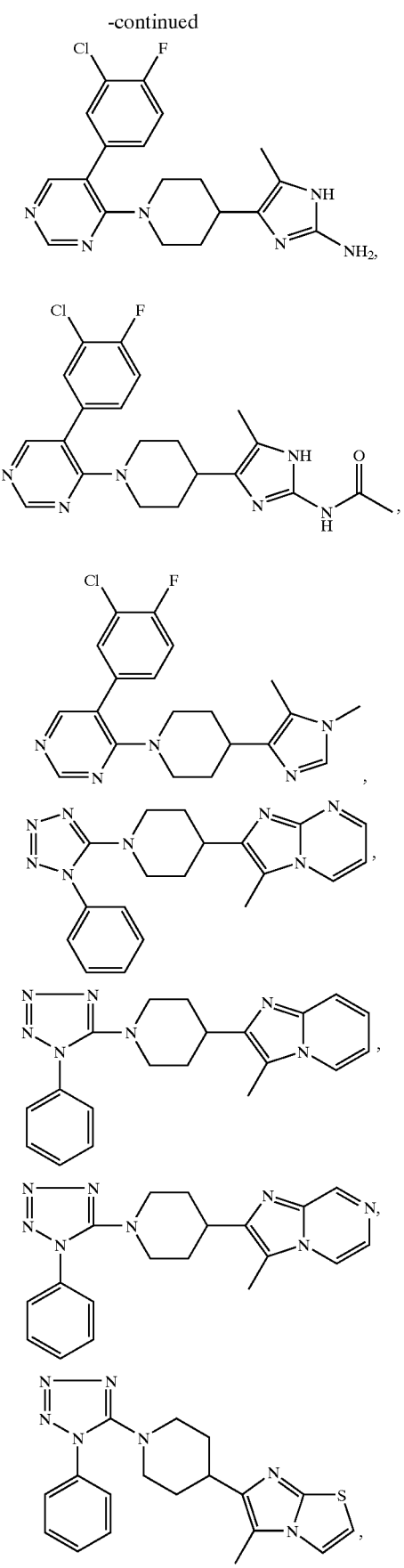

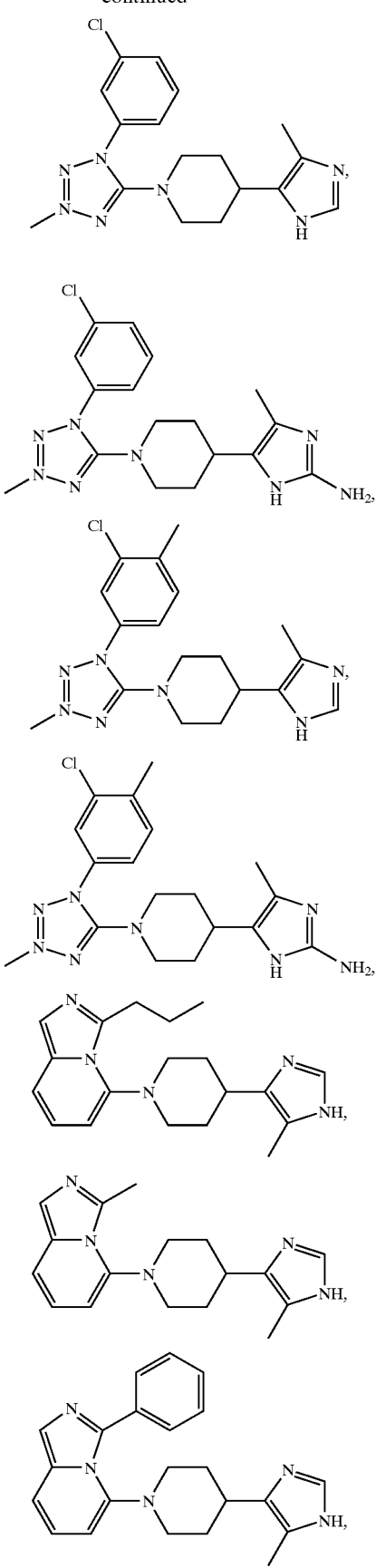
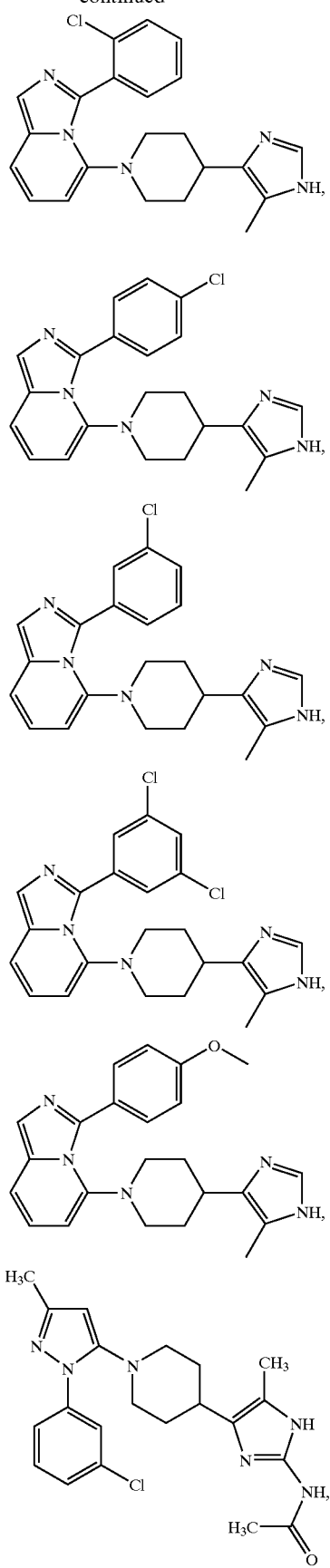

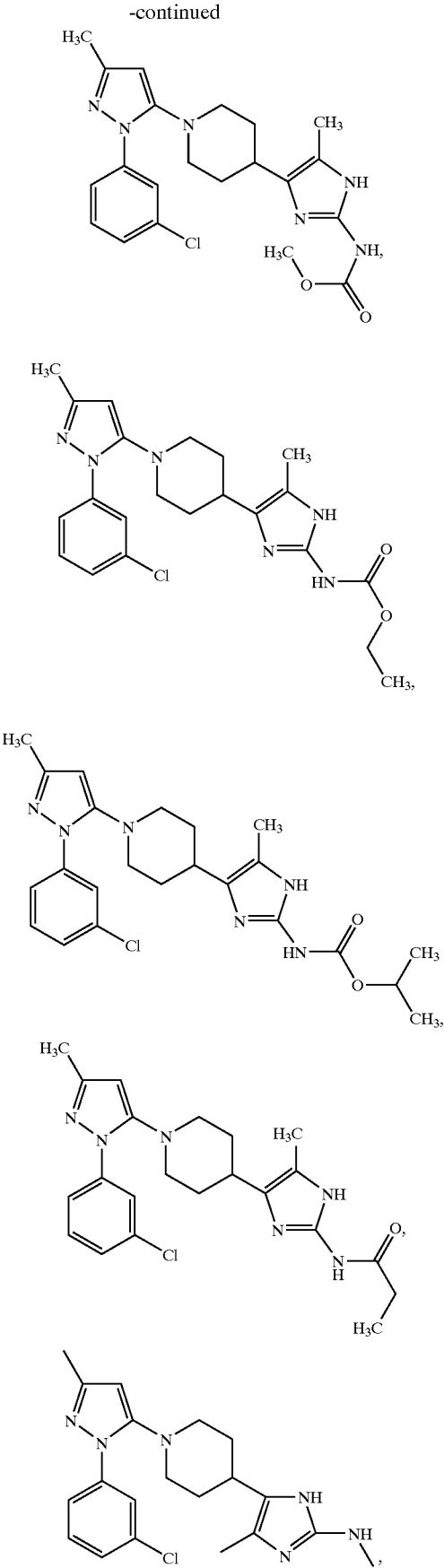
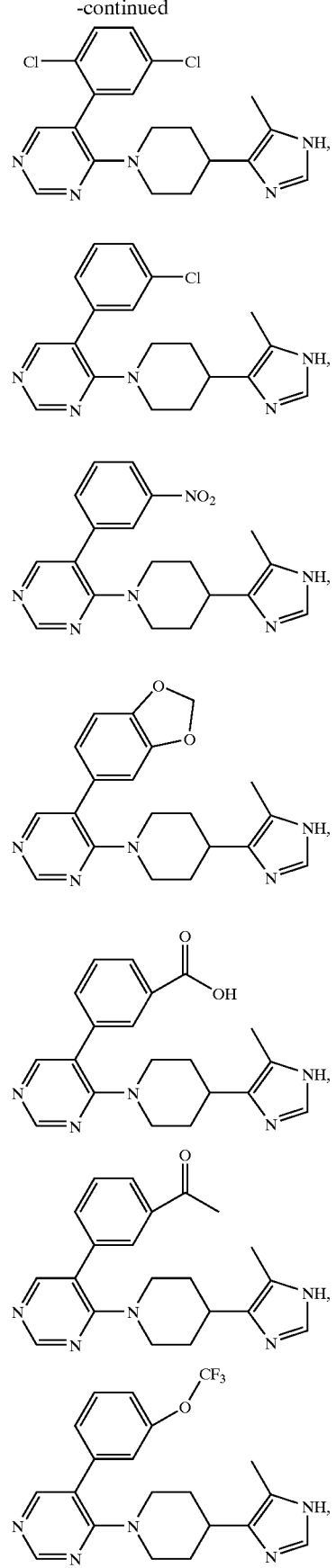

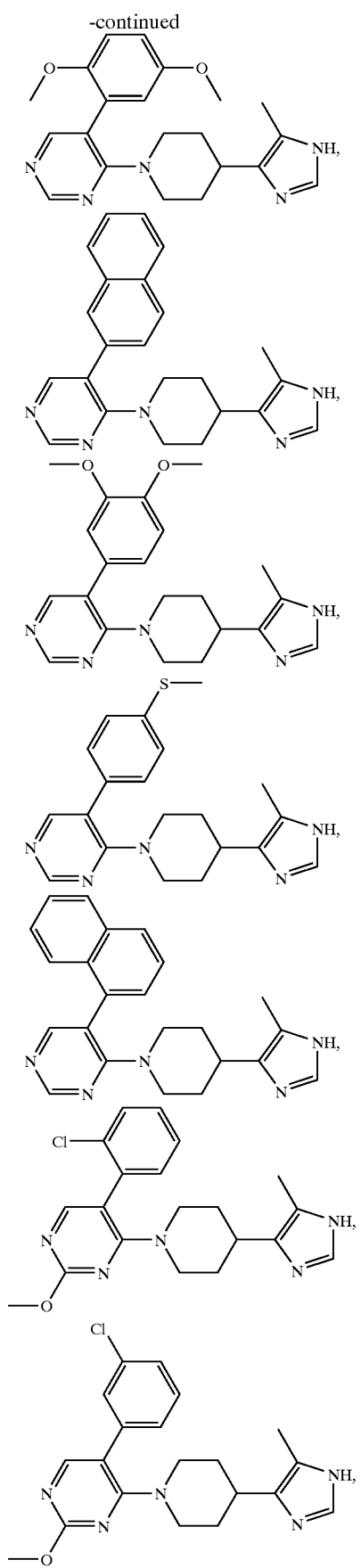
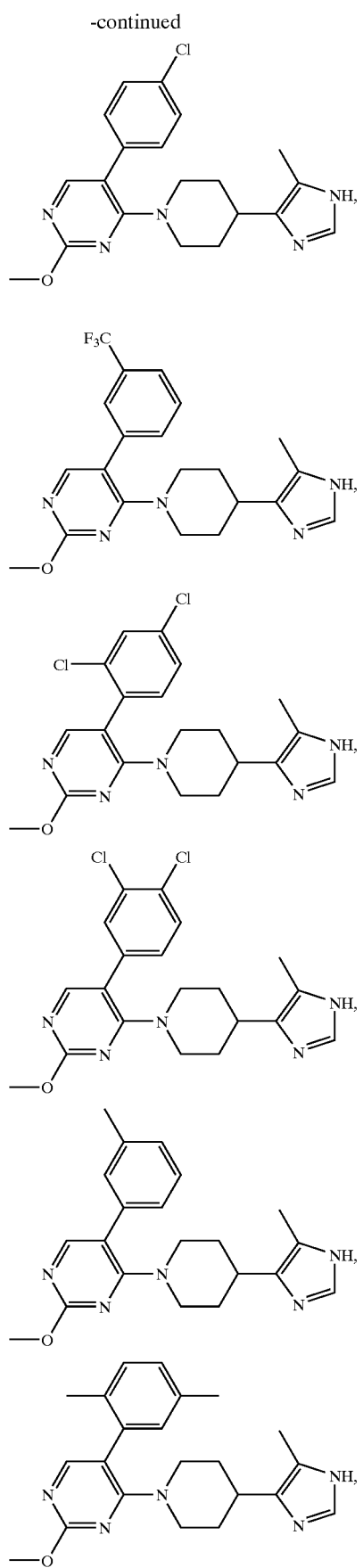

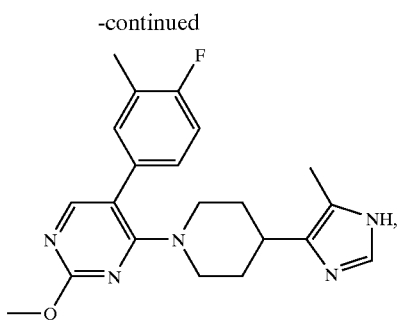
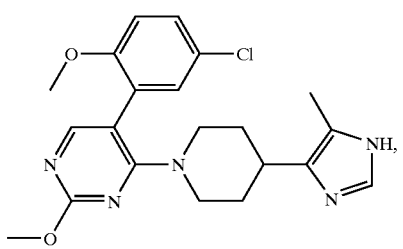
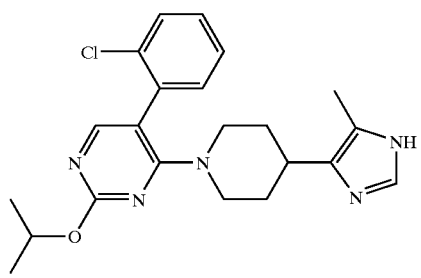
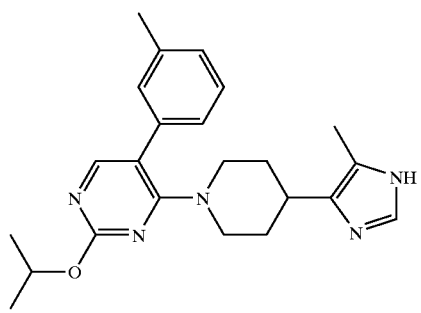
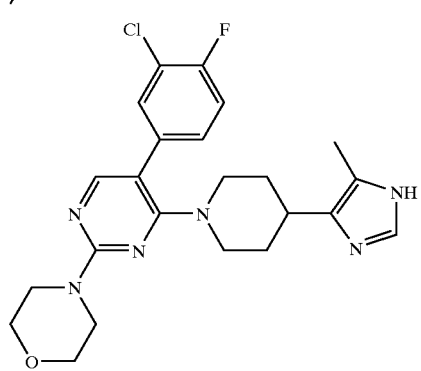
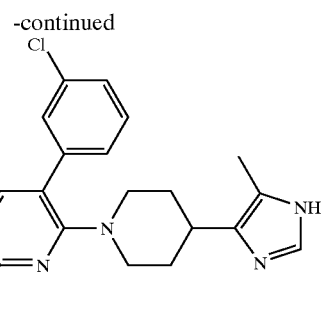
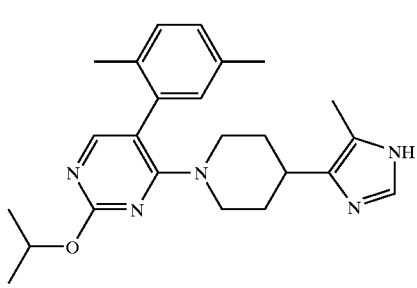
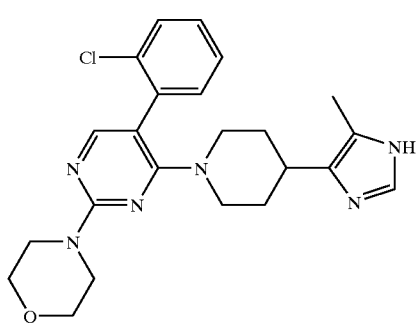
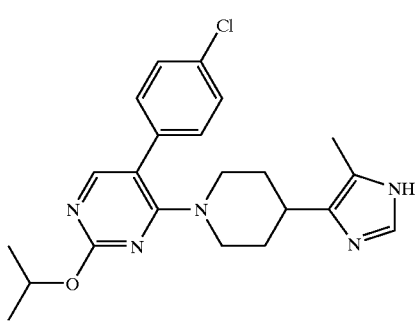
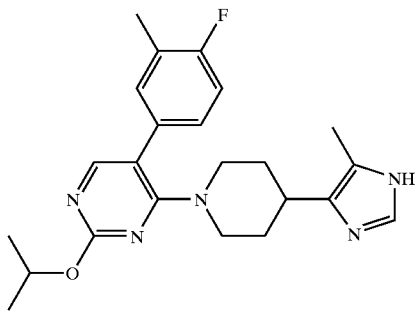

215
-continued
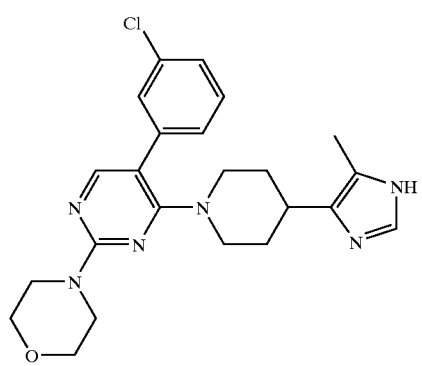
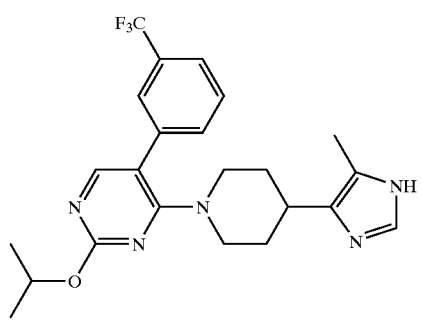
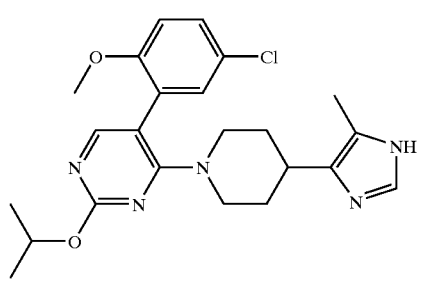
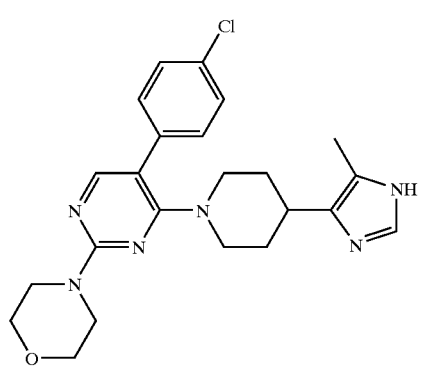
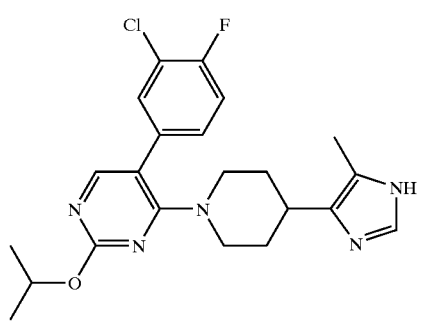
216
-continued
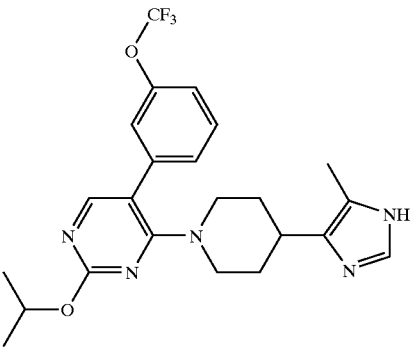
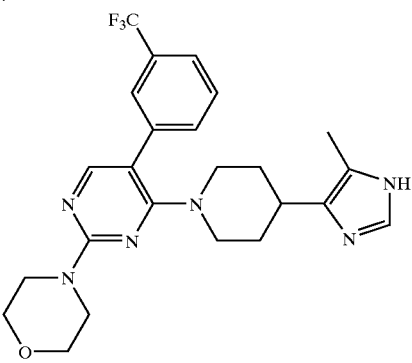
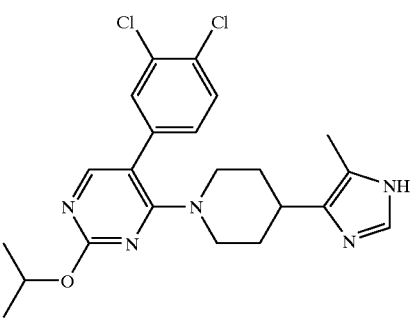
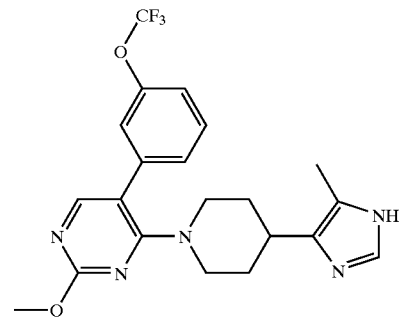
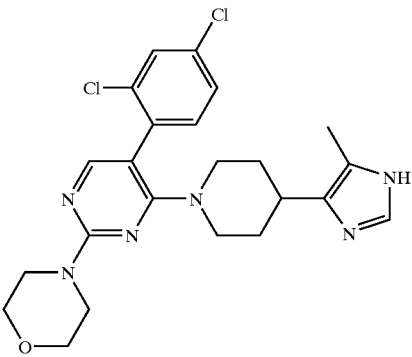

217
-continued
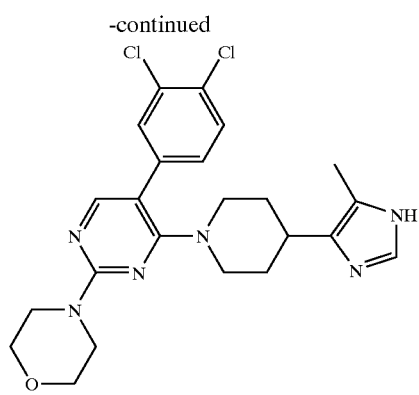
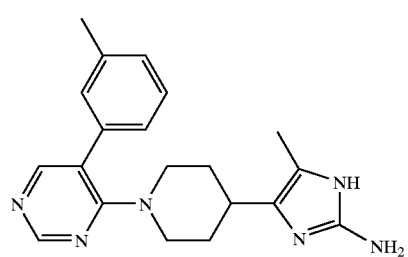
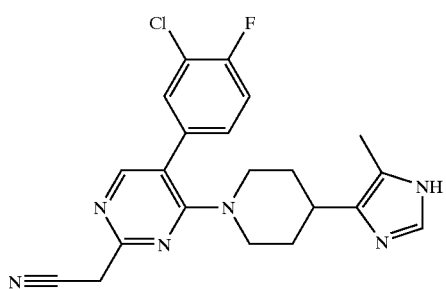
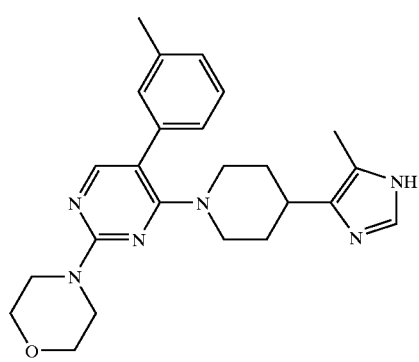
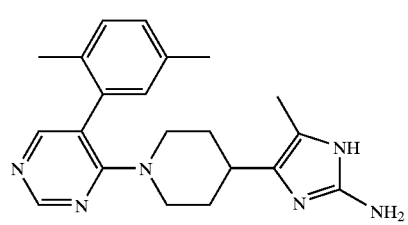
218
-continued
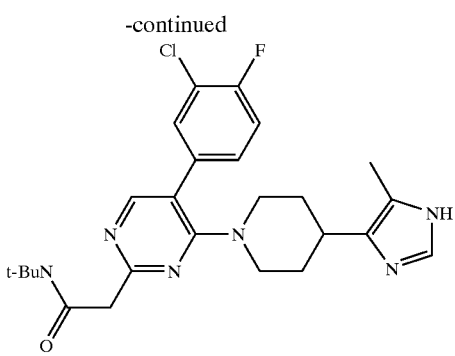
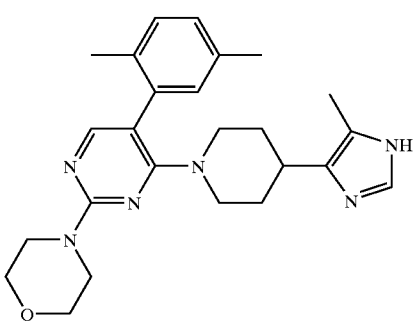
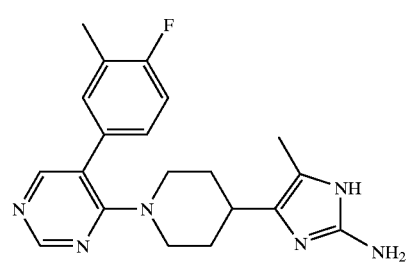
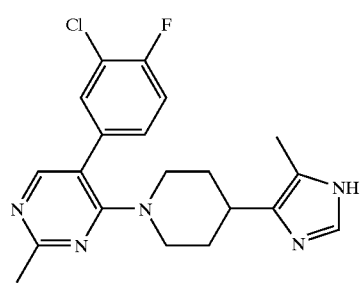
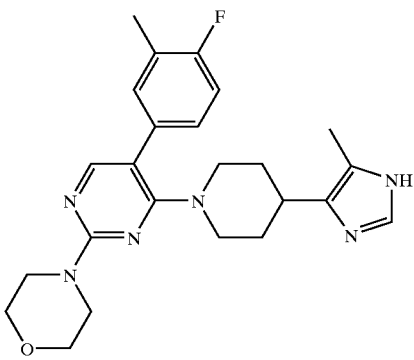

-continued
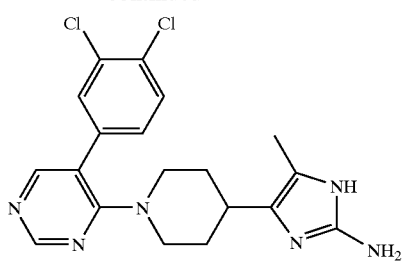
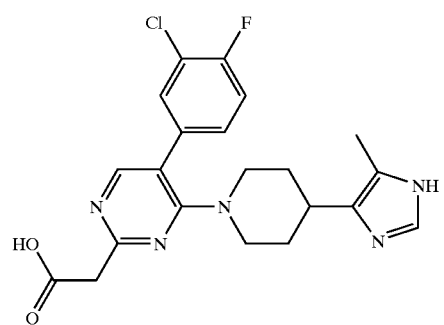
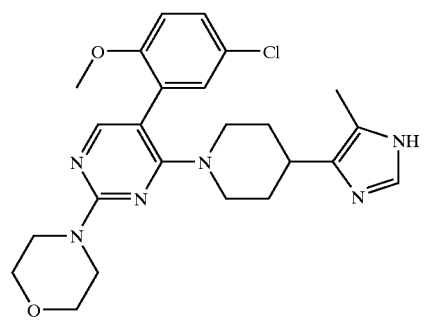
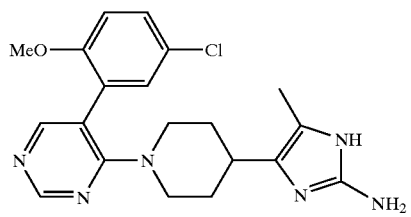
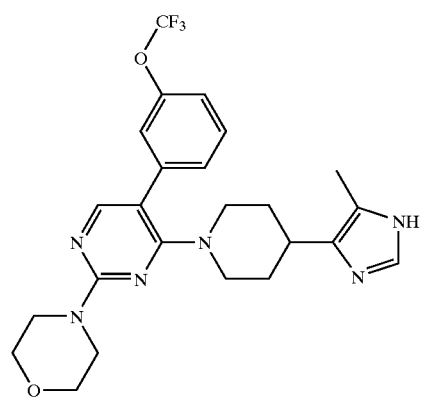
-continued
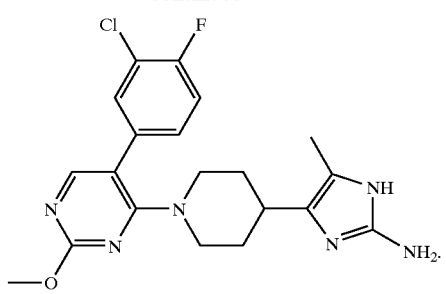
14. A compound having the structure
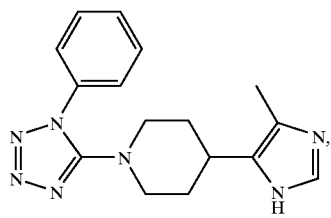
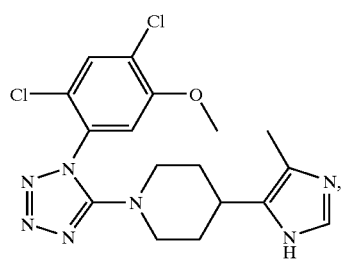
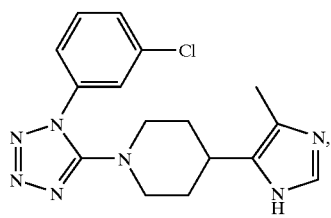
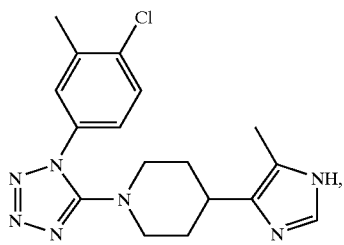
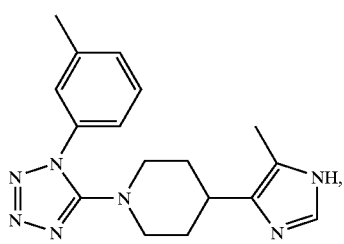

-continued
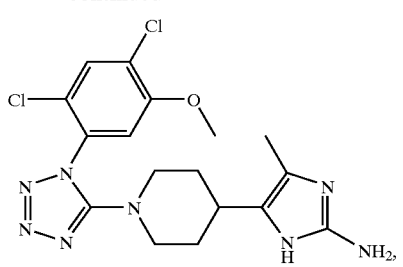
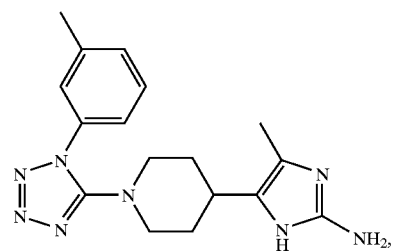
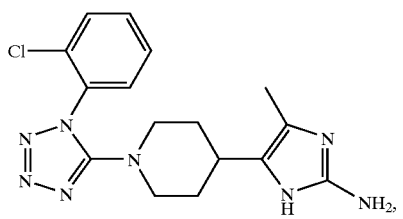
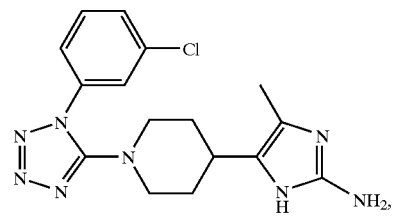
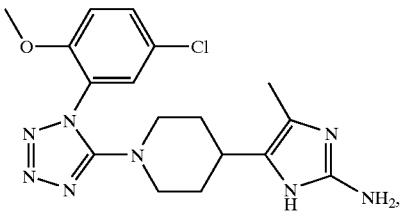
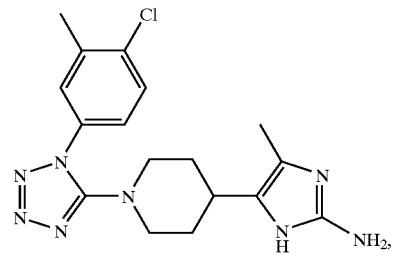
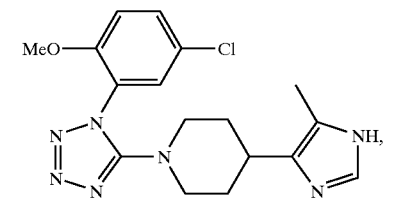
-continued
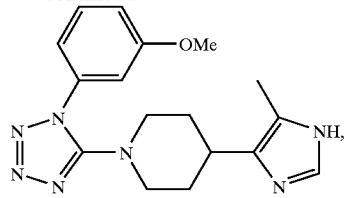
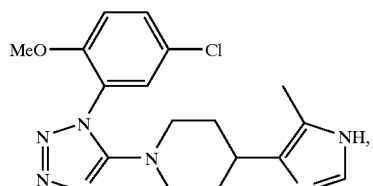
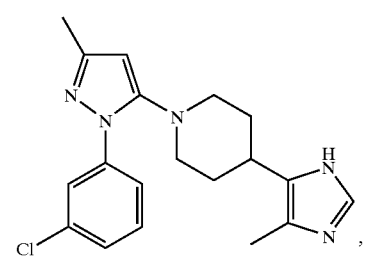
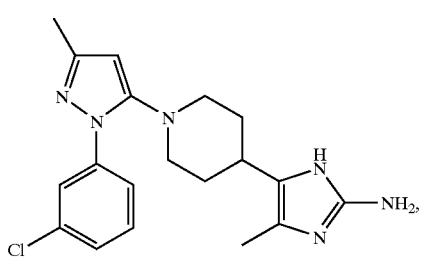
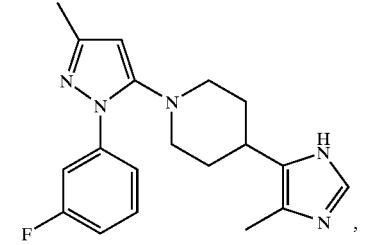
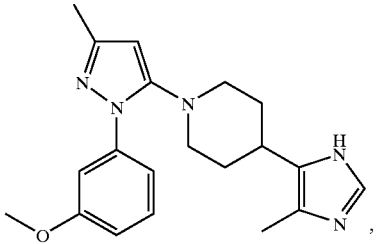
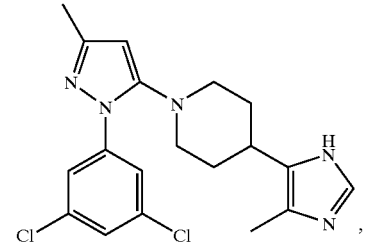

-continued
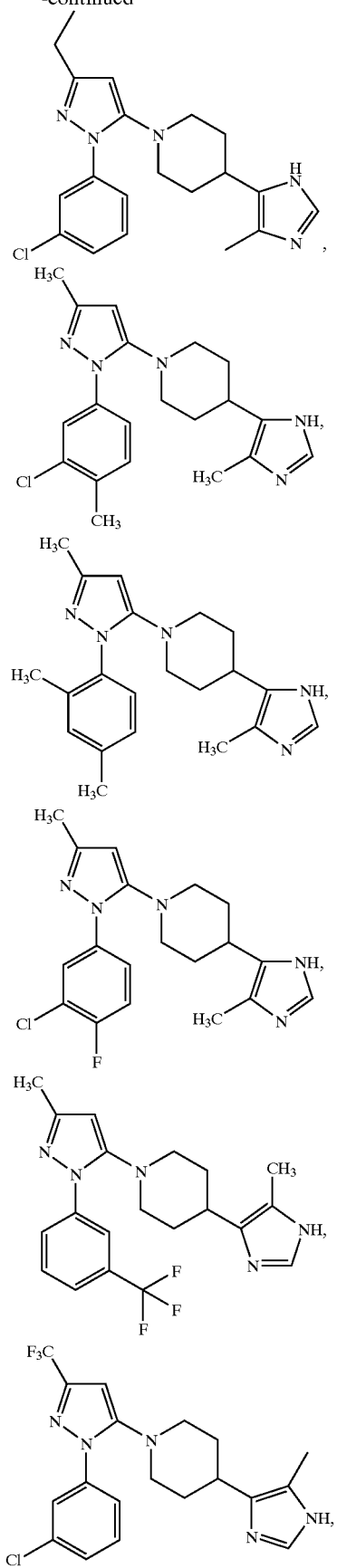
-continued
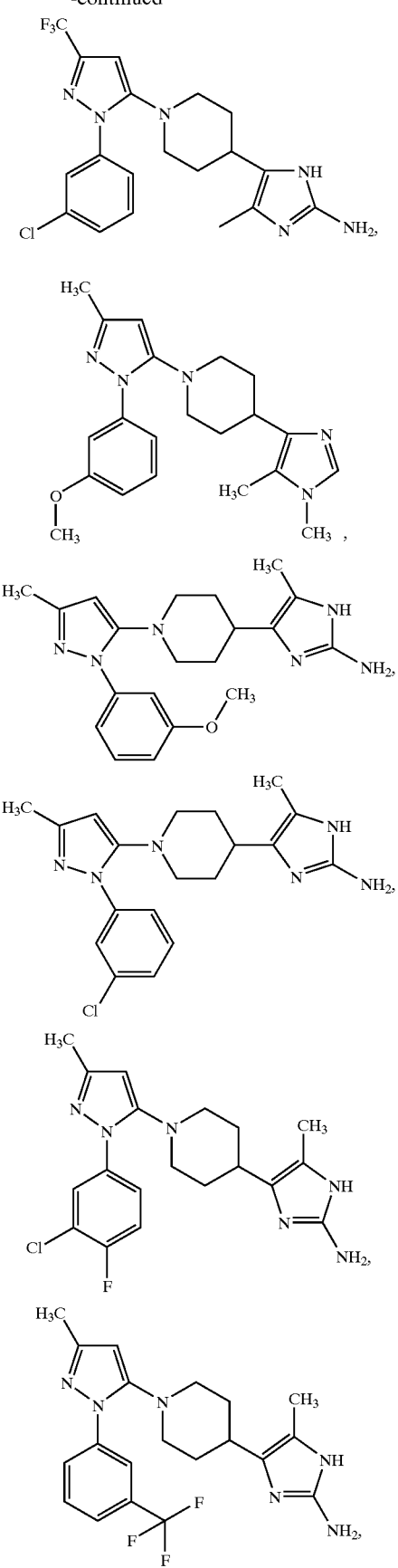

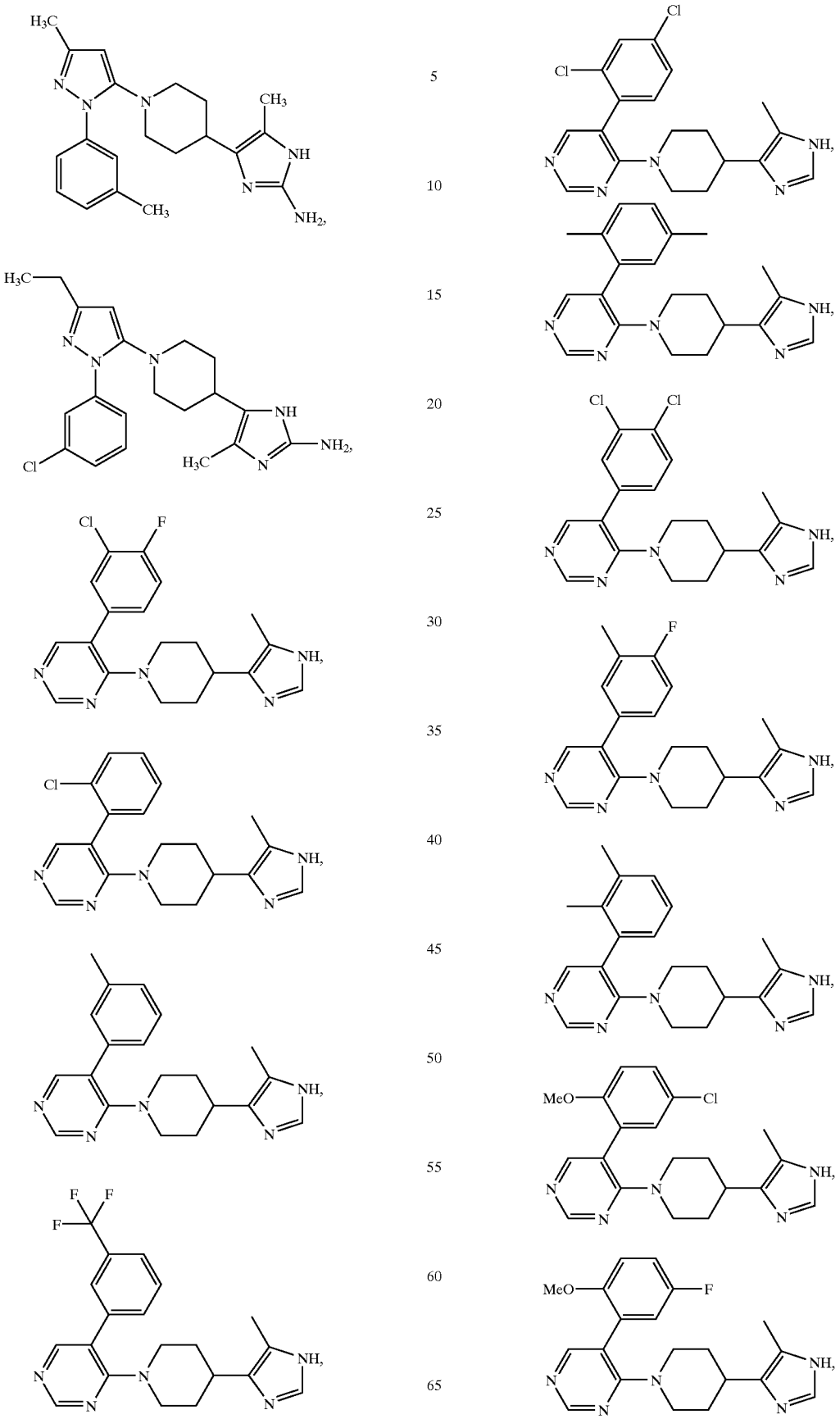

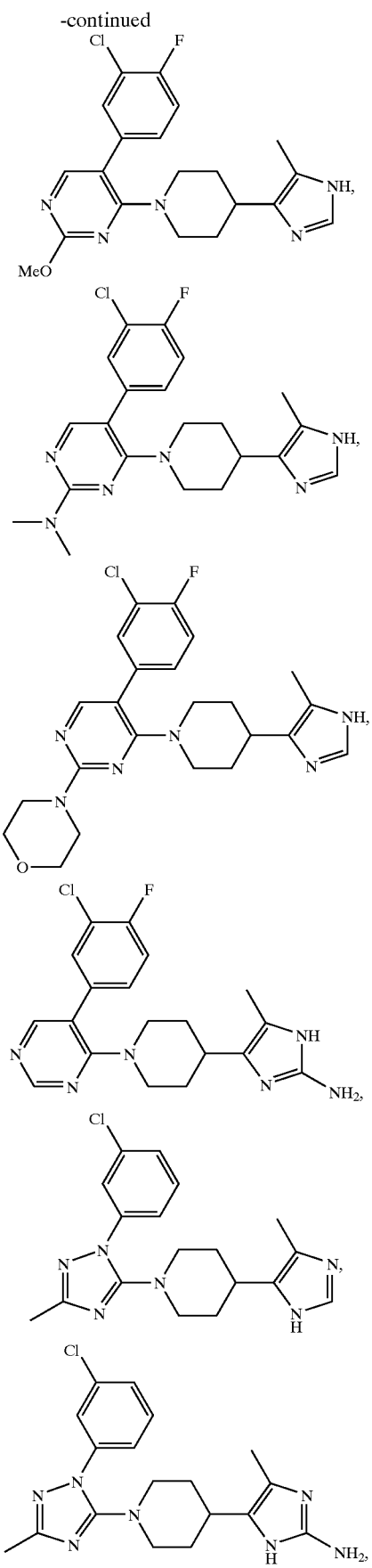
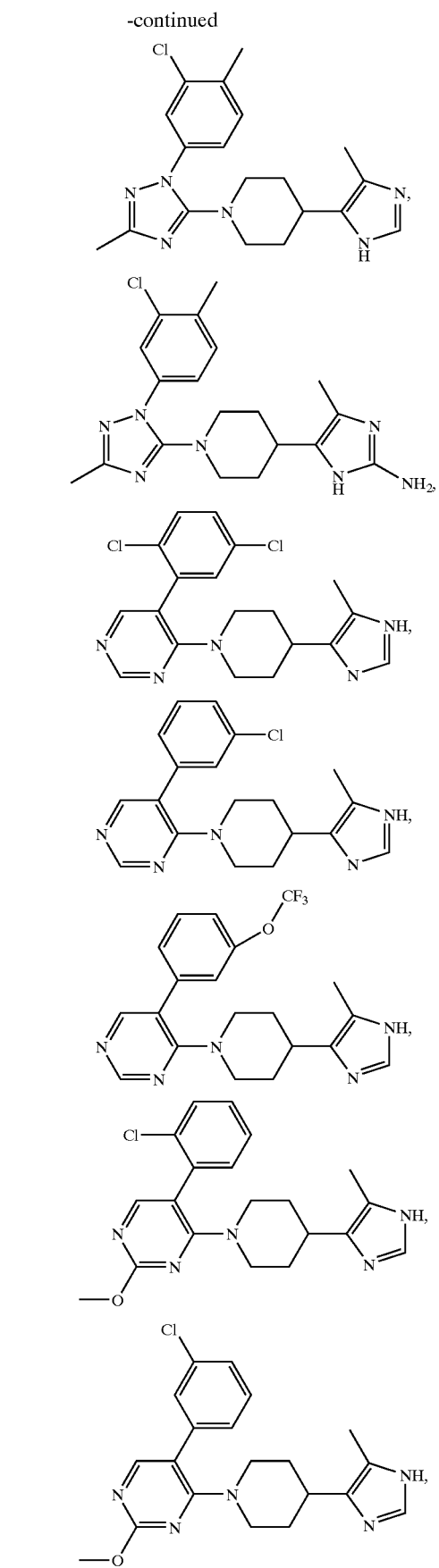

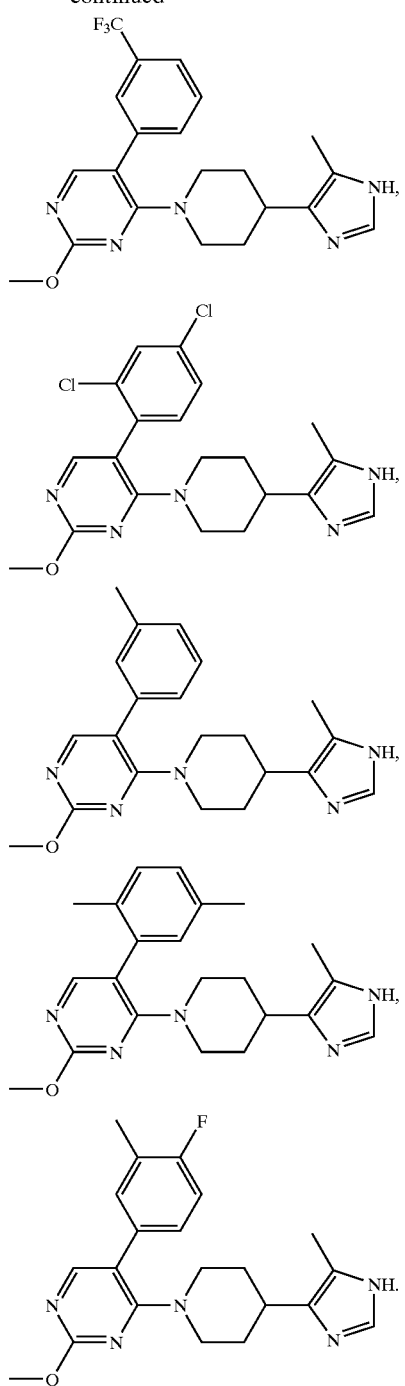
15. A compound having the structure
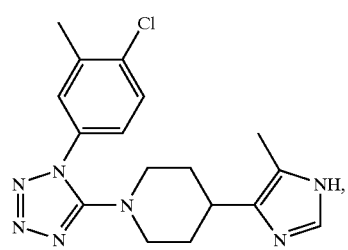
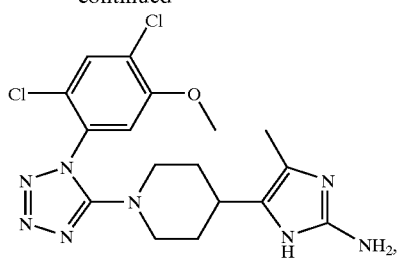
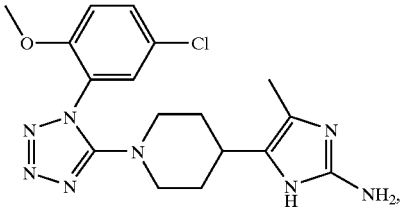
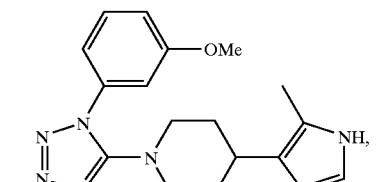
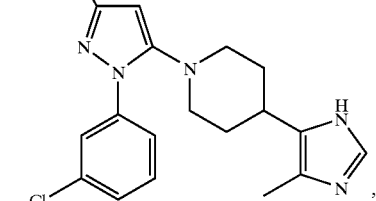
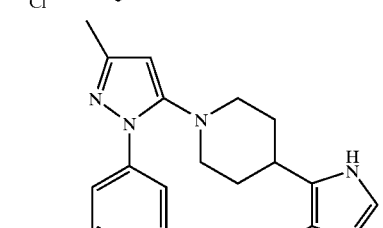
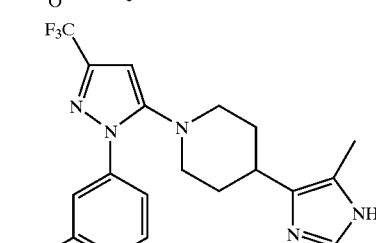
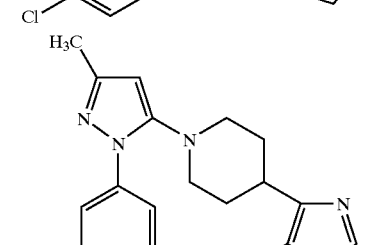

-continued

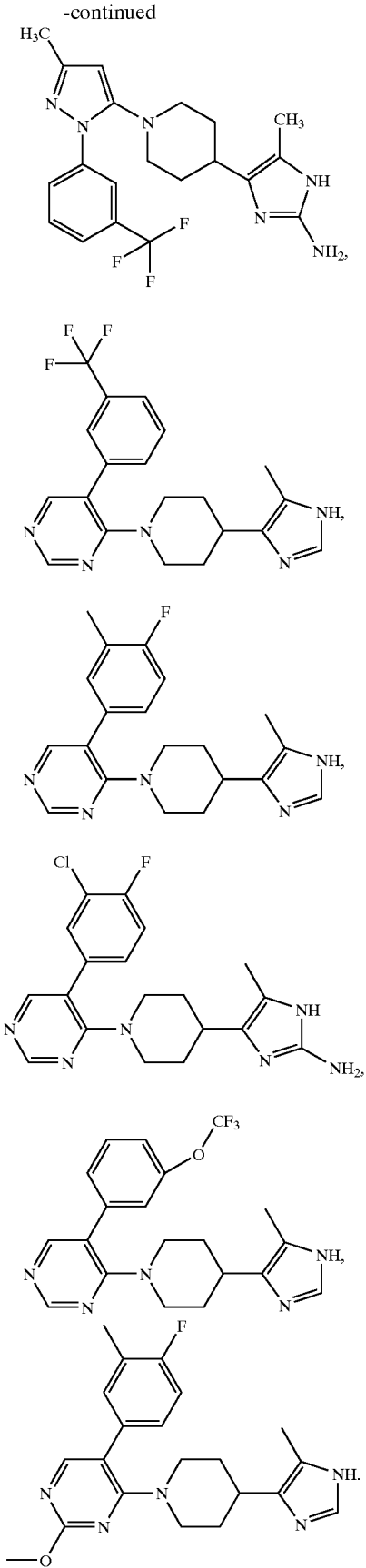

16. A compound having the following structure

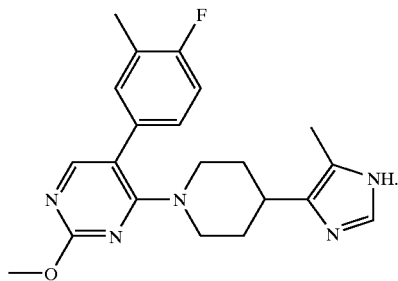

17. A compound having the structure

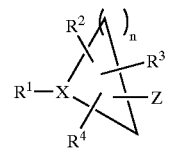

wherein n is 4;

X is N;

Z is a 5- or 6-membered nitrogen-containing monocycle heteroaryl group which is selected from the group consisting of imidazole attached at its 4- or 5-position to the ring, aminoimidazole, alkylimidazole, alkylthioimidazole, alkylthio(amino)imidazole, amino(alkyl)imidazole, (alkanoylamino)imidazole, aminothiazole, aminooxazole, aminooxadiazole, dialkylimidazole, alkyl(alkanoylamino)imidazole, alkyl(amino)imidazole, arylaminocarbonylamino(alkyl)imidazole, alkoxycarbonylamino(alkyl)imidazole, alkylcarbonylamino(alkyl)imidazole, aminotriazole or diaminopyrimidine;

$R^1$ is tetrazolyl, pyrazolyl, thiazolyl,

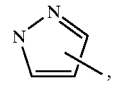

oxazole, triazole or

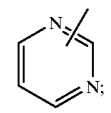

and $R^1$ may be unsubstituted or substituted with from one to five substituents;

$R^2$, $R^3$ and $R^4$ are the same or different and are independently H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, amino, alkylamino, dialkylamino, alkenylamino, alkynylamino, arylalkylamino, aryl, arylalkyl, arylamino, aryloxy, cycloheteroalkyl, cycloheteroalkylalkyl, heteroaryl, heteroarylamino, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl, polyhaloalkoxy, aminothio, aminosulfinyl, aminosulfonyl, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, acyl, carboxy, aminocarbonyl, alkylcarbonyl, alkoxycarbonyl, alkylcarbonyloxy, alkylcarbonylamino, arylcarbonyl, arylcarbonyloxy, arylcarbonylamino, heteroarylcarbonyl, heteroarylcarbonyloxy, heteroarylcarbonylamino, cyano, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, alkoxycarbonylamino, 1,1-(alkoxyl or aryloxy)$_2$alkyl (where the two aryl or alkyl substituents can be independently defined, or linked to one another to form a ring), S(O)$_2$R$^6$R$^7$, —NR$^6$(C=NR$^7$)alkyl, —NR$^6$(C=NR$^7$)alkenyl, —NR$^6$(C=NR$^7$)alkynyl, —NR$^6$(C=NR$^7$)heteroaryl, —NR$^8$(C=NCN)-amino,

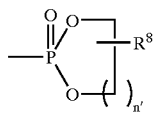

pyridine-N-oxide,

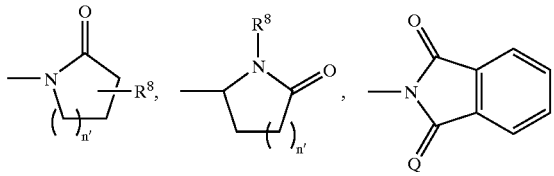

(where Q is O or H$_2$ and n' is 0, 1, 2 or 3) or

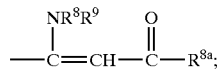

tetrazolyl, pyrazolyl, pyridyl, thiazolyl, pyrimidinyl, imidazole, oxazole, or triazole, —PO(R$^{13}$)(R$^{14}$), (where R$^{13}$ and R$^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); and may be optionally independently substituted with from one to five substituents, which may be the same or different;

R$^6$, R$^7$, R$^8$, R$^{8a}$ and R$^9$ are the same or different and are independently hydrogen, alkyl, haloalkyl, aryl, heteroaryl, arylalkyl, cycloalkyl, (cycloalkyl)alkyl, or cycloheteroalkyl;

or a pharmaceutically acceptable salt thereof, or a prodrug thereof, and all stereoisomers thereof.

18. The compound as defined in claim 17 wherein Z is imidazole attached to its 4- or 5-position to the ring, aminoimidazole, alkylimidazole, alkylthioimidazole, alkylthio(amino)imidazole, amino-(alkyl)imidazole, (alkanoylamino)imidazole, aminothiazole, aminooxazole, aminooxadiazole, dialkylimidazole, alkyl(alkanoylamino)imidazole, alkyl(amino)imidazole, arylaminocarbonylamino(alkyl)imidazole, alkoxycarbonylamino(alkyl)imidazole, alkylcarbonylamino(alkyl)imidazole, aminotriazole or diaminopyrimidine.

19. The compound as defined in claim 1 wherein the R$^1$ group may be substituted within from one to five of the following groups:

alkyl, alkenyl, alkynyl, alkoxy, alkenyloxy, alkynyloxy, (alkyl or aryl)$_3$Si (where each alkyl or aryl group is independent), cycloalkyl, cycloalkenyl, amino, alkylamino, dialkylamino, alkenylamino, alkynylamino, arylalkylamino; aryl, arylalkyl, arylamino, aryloxy, cycloheteroalkyl, cycloheteroalkylalkyl, heteroaryl, heteroarylamino, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl such as CF$_3$ and CF$_3$CH$_2$, polyhaloalkyloxy such as CF$_3$O and CF$_3$CH$_2$O, aminothio, aminosulfinyl, aminosulfonyl, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, acyl, carboxy, aminocarbonyl, alkylcarbonyl, alkoxycarbonyl, alkylcarbonyloxy, alkylcarbonylamino, arylcarbonyl, arylcarbonyloxy, arylcarbonylamino, heteroarylcarbonyl, heteroarylcarbonyloxy, heteroarylcarbonylamino, cyano, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, 1,1-(alkoxyl or aryloxy)$_2$alkyl (where the two aryl or alkyl substituents can be independently defined, or linked to one another to form a ring, such as 1,3-dioxane or 1,3-dioxolane), S(O)$_2$R$^6$R$^7$, —NR$^6$(C=NR$^7$)alkyl,

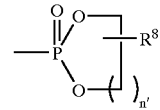

NR$^6$(C=NR$^7$)alkenyl, —NR$^6$(C=NR$^7$)alkynyl, NR$^6$(C=NR$^7$)heteroaryl, —NR((C=NCN)-amino, pyridine-N-oxide,

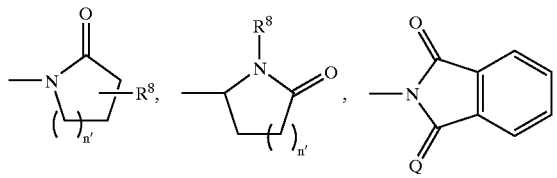

(where Q is O or H$_2$ and n' is 0, 1, 2 or 3) or

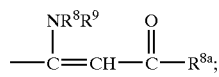

tetrazolyl, pyrazolyl, pyridyl, thiazolyl, pyrimidinyl, oxazole or triazole; —PO($R^{13}$)($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy);

$R^6$, $R^7$, $R^8$, $R^{8a}$ and $R^9$ are independently hydrogen, alkyl, haloalkyl, aryl, heteroaryl, arylalkyl, cycloalkyl, (cycloalkyl)alkyl or cycloheteroalkyl, which substituents may be the same or different from each other and may be the same or different from the base $R^1$ group.

20. The compound as defined in claim 17 wherein $R^1$ is substituted with one to five of the following substituents: alkyl, alkylaminocarbonyl, arylaminocarbonyl, heteroarylaminocarbonyl, alkylcarbonylamino, heteroaryl, halo, aryl, cycloalkylcarbonylamino, arylcarbonylamino, heteroarylcarbonylamino, alkoxycarbonylamino, guanidinyl, nitro, cycloheteroalkyl, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

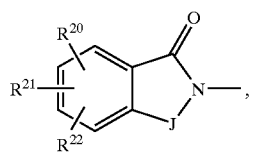

Where

J is: $CHR^{23}$,

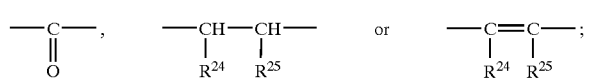

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to $R^1$, or attached via an alkylene chain at an open position, which substituents may be the same or different from each other, and may be the same or different from the base $R^1$ group.

21. The compound as defined in claim 17 wherein Z is imidazole attached at its 4- or 5-position to the ring, aminoimidazole, alkylimidazole, alkylthioimidazole, alkylthio(amino)imidazole, amino(alkyl)imidazole or (acetylamino)imidazole.

22. The compound as defined in claim 17 wherein the moiety

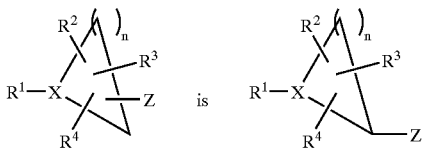

23. The compound as defined in claim 17 wherein $R^2$ and $R^3$ are independently H, lower alkoxy or aryl, and $R^4$ and $R^5$ are each hydrogen.

24. The compound as defined in claim 17 wherein $R^1$ is

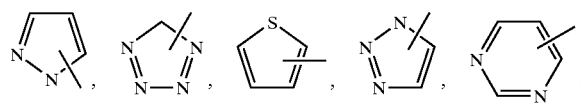

25. The compound as defined in claim 17 wherein $R^1$, $R^2$, $R^3$ and/or $R^4$ may be joined together with the N atom and/or carbons to which they are attached to form a non-aromatic ring.

26. The compound as defined in claim 17 wherein

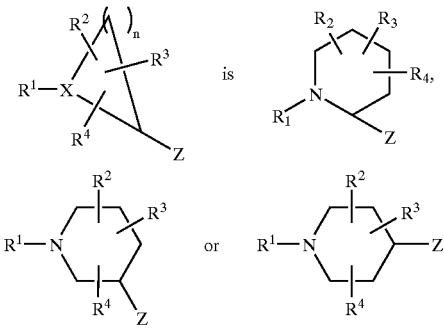

27. The compound as defined in claim 17 having the structure

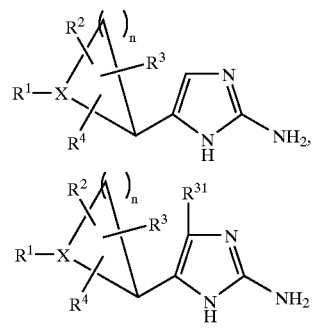

($R^{31}$ = alkyl, haloalkyl, aryl, heteroaryl),

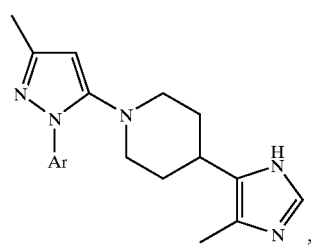

(Ar = aryl or heteroaryl)

-continued
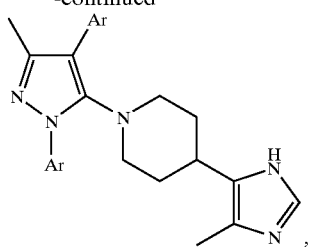
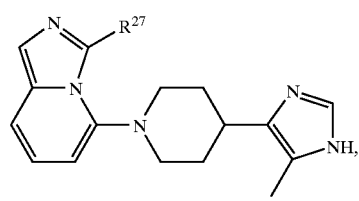
($R^{27}$ = alkyl or aryl)
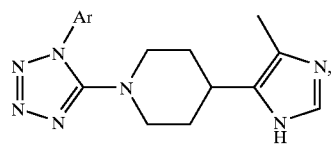
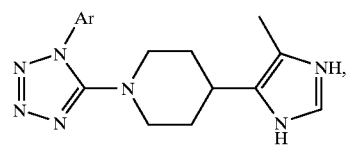
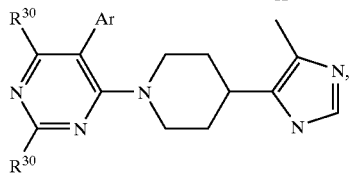
($R^{30}$ = alkyl or halo)
-continued
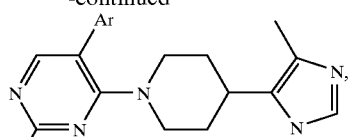
(Nu = alkyl-O, alkyl NH, (alkyl)$_2$N, alkyl-S or alkyl)
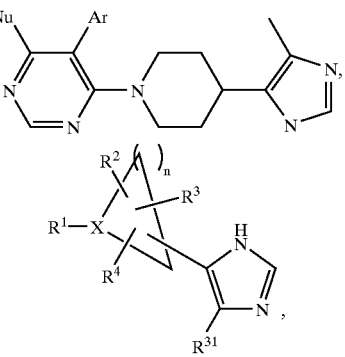
IR
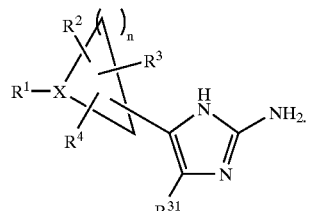
IS
28. A pharmaceutical composition comprising a compound as defined in claim 1 and a pharmaceutically acceptable carrier therefor.
* * * * *